United States Patent
Katsuhira et al.

(10) Patent No.: US 6,747,041 B1
(45) Date of Patent: Jun. 8, 2004

(54) HETEROCYCLIC DICARBOXYLIC ACID DIAMIDE DERIVATIVES, AGRICULTURAL/ HORTICULTURAL INSECTICIDES AND METHOD OF USING THE SAME

(75) Inventors: Takeshi Katsuhira, Kawachinagano (JP); Takashi Furuya, Izumisano (JP); Makoto Gotoh, Sakai (JP); Masanori Tohnishi, Sakai (JP); Hideo Takaishi, Nishinomiya (JP); Kazuyuki Sakata, Kawachinagano (JP); Masayuki Morimoto, Kawachinagano (JP); Akira Seo, Hashimoto (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 10 days.

(21) Appl. No.: 10/018,463

(22) PCT Filed: Jun. 23, 2000

(86) PCT No.: PCT/JP00/04136

§ 371 (c)(1),
(2), (4) Date: Apr. 10, 2002

(87) PCT Pub. No.: WO01/00575

PCT Pub. Date: Jan. 4, 2001

(30) Foreign Application Priority Data

Jun. 24, 1999 (JP) ............................................. 11-179035

(51) Int. Cl.[7] ..................... C07D 211/94; C07D 401/12; C07D 401/14; A61K 31/4427; A61K 31/4355

(52) U.S. Cl. ..................... 514/307; 514/309; 514/311; 514/312; 514/354; 514/355; 546/316; 546/323; 546/141; 546/146; 546/156; 546/169; 546/313

(58) Field of Search .................. 514/307, 309, 514/311, 312, 355, 354; 546/316, 323, 141, 146, 156, 169, 313

(56) References Cited

U.S. PATENT DOCUMENTS 5,843,868 A 12/1998 Tonishi et al.

FOREIGN PATENT DOCUMENTS

| EP | 0 919 542 | 6/1999 |
| EP | 1 006 107 | 6/2000 |
| HU | P920089 | 5/1993 |
| HU | 207853 | 6/1993 |
| JP | 06-025190 | 2/1994 |
| JP | 2000-007661 | 1/2000 |
| WO | WO 99/44992 | 9/1999 |
| WO | WO 00/06549 | 2/2000 |

OTHER PUBLICATIONS

Tsuda et al. "Synthesis of esters, amides, N–alkylamides and N, N–dialkylamides of 2,3–dimethyl–5–(2,5–disubstituted phenylaminocarbonyl)–6–prazinecarboxylic acid and their phytotoxicity", J. Pestic. Sci. (Int. Ed.), (1992), vol. 17, No. 4, pp261–265.

Ivanov et al. "New derivatives of imidazole–4,5–dicarboxylic acid", Ukr. Khim. Zh. (Russ. Ed.) (1983), vol. 49, No. 12, pp1301–1306.

Augustin et al. "Synthesis of quinoxaline– and indole–2, 3–dicarboxylic acid imides", Tetrahedron, (1980), vol. 36, No. 12, pp1801–1805.

Mohamed et al. "A facile synthesis and reactions of 6,7–dimenthylquinoxaline–2,3–dicarboximides", Afinidad, (1993), vol. 50, No. 444, pp123–126.

Primary Examiner—Mark L. Berch
Assistant Examiner—Kahsay Habte
(74) Attorney, Agent, or Firm—Paul E. White, Jr.; Manelli Denison & Selter PLLC

(57) ABSTRACT

Heterocyclic dicarboxylic acid diamide derivative represented by the general formula (I):

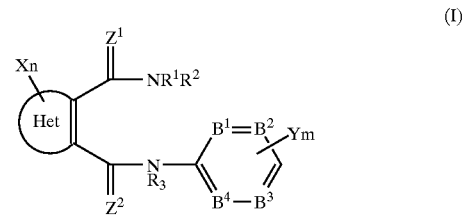

wherein $R^1$, $R^2$ and $R^3$ represent each H, optionally halogenated $C_{3-6}$ cycloalkyl, etc.; Het represents a 5- or 6-membered heterocycle; X and Y represent each halocyano, nitro, optionally halogenated $C_{3-6}$, cycloalkyl, optionally substituted phenyl, an optionally substituted heterocycle, etc; n is from 0 to 3; m is from 1 to 5; $Z^1$ and $Z^2$ represent each O or S; and $B^1$ to $B^4$ represent each C or N. Agricultural/horticultural insecticides having an excellent controlling effect on pest insects such as diamond-back moth (*Pluntella xylostella*) and tobacco cutworm (*Spodoptera litura*).

7 Claims, No Drawings

HETEROCYCLIC DICARBOXYLIC ACID DIAMIDE DERIVATIVES, AGRICULTURAL/ HORTICULTURAL INSECTICIDES AND METHOD OF USING THE SAME

This application is the national phase of international application PCT/JP00/04136 filed Jun. 23, 2000 which designated the U.S.

TECHNICAL FIELD

The present invention relates to heterocyclic dicarboxylic acid diamide derivatives, agricultural and horticultural insecticides containing any of said compounds as an active ingredient, and their usage.

BACKGROUND ART

JP-A-6-25190, JP-A-9-323974, WO9944992, JP-A-12-7661, JP-A-12-103708 and the like disclose compounds constituting a portion of the heterocyclic dicarboxylic acid diamide derivative of the present invention but do not describe or suggest the usefulness of the disclosed compounds as agricultural and horticultural insecticides at all.

The present inventors earnestly investigated in order to develop a novel agricultural and horticultural insecticide, and consequently found that heterocyclic dicarboxylic acid diamide derivatives represented by the general formula (I) of the present invention are novel compounds not known in any literature and that not only these compounds but also the compounds disclosed in the prior arts can be put to a novel use, whereby the present invention has been accomplished.

DISCLOSURE OF THE INVENTION

The present invention relates to heterocyclic dicarboxylic acid diamide derivatives represented by the general formula (I):

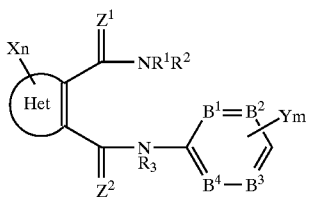

{wherein $R^1$, $R^2$ and $R^3$, which may be the same or different, are hydrogen atoms, $(C_3-C_6)$cycloalkyl groups, halo$(C_3-C_6)$cycloalkyl groups or $-A^1-(R^4)r$ (wherein $A^1$ is a $(C_1-C_8)$alkylene group, a $(C_3-C_6)$alkenylene group or a $(C_3-C_6)$alkynylene group, $R^4$, which may be the same or different, are hydrogen atoms; halogen atoms; cyano groups; nitro groups; halo$(C_1-C_6)$alkyl groups; $(C_3-C_6)$cycloalkyl groups; halo$(C_3-C_6)$cycloalkyl groups; $(C_1-C_6)$alkoxycarbonyl groups; di$(C_1-C_6)$alkoxyphosphoryl groups whose $(C_1-C_6)$alkoxy groups may be the same or different; di$(C_1-C_6)$alkoxythiophosphoryl groups whose $(C_1-C_6)$alkoxy groups may be the same or different; diphenylphosphino groups; diphenylphosphono groups; phenyl groups; substituted phenyl groups having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; heterocyclic groups; substituted heterocyclic groups having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or $-A^2-R^5$ (wherein $A^2$ is $-O-$, $-S-$, $-SO-$, $-SO_2-$, $-N(R^6)-$ (wherein $R^6$ is a hydrogen atom; a $(C_1-C_6)$alkylcarbonyl group; a halo$(C_1-C_6)$alkylcarbonyl group; a $(C_1-C_6)$alkoxycarbonyl group; a phenylcarbonyl group; a substituted phenylcarbonyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a phenyl$(C_1-C_4)$alkoxycarbonyl group; a substituted phenyl$(C_1-C_4)$alkoxycarbonyl group having on the ring one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a $(C_1-C_6)$alkylsulfonyl group; or a halo$(C_1-C_6)$alkylsulfonyl group), $-C(=O)-$ or $-C(=NOR^7)-$ (wherein $R^7$ is a hydrogen atom; a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a cyclo$(C_3-C_6)$alkyl group; a phenyl$(C_1-C_4)$alkyl group; or a substituted phenyl$(C_1-C_4)$alkyl group having on the ring one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups), and $R^5$ is a hydrogen atom; a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a halo$(C_3-C_6)$alkynyl group; a $(C_3-C_6)$cycloalkyl group; a halo$(C_3-C_6)$cycloalkyl group; a $(C_1-C_6)$alkoxy$(C_1-C_6)$alkyl group; a $(C_1-C_6)$alkylthio$(C_1-C_6)$alkyl group; a formyl group; a $(C_1-C_6)$alkylcarbonyl group; a halo$(C_1-C_6)$alkylcarbonyl group; a $(C_1-C_6)$alkoxycarbonyl group; a mono$(C_1-C_6)$alkylaminocarbonyl group; a di$(C_1-C_6)$alkylaminocarbonyl group whose $(C_1-C_6)$alkyl groups may be the same or different; a mono$(C_1-C_6)$alkylaminothio-carbonyl group; a di$(C_1-C_6)$alkylaminothiocarbonyl group whose $(C_1-C_6)$alkyl groups may be the same or different; a di$(C_1-C_6)$alkoxyphosphoryl group whose $(C_1-C_6)$alkoxy groups may be the same or different; a di$(C_1-C_6)$alkoxythiophosphoryl group whose $(C_1-C_6)$alkoxy groups may be the same or different; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a phenyl$(C_1-C_4)$alkyl group; a substituted phenyl$(C_1-C_4)$alkyl group having on the ring one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a heterocyclic group; or a substituted heterocyclic group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups), and r is an integer of 1 to 4), provided that $R^1$ and $R^2$ are not hydrogen atoms at the same time, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom, Het is a heterocyclic group represented by any of the following formulas Q1 to Q22:

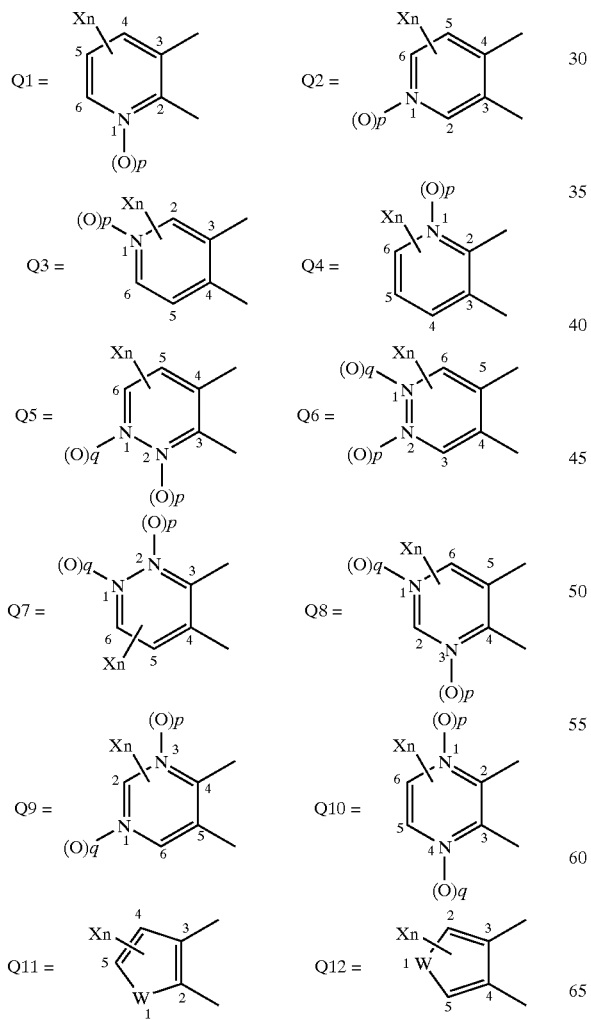

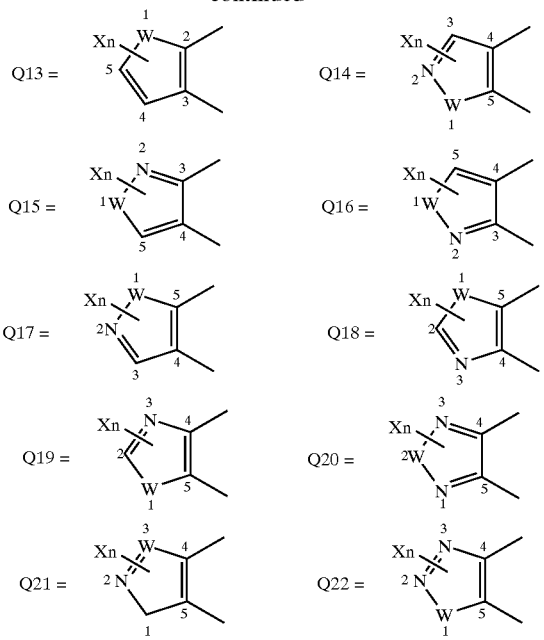

(wherein X, which may be the same or different, are halogen atoms; cyano groups; nitro groups; $(C_3-C_6)$cycloalkyl groups; halo$(C_3-C_6)$cycloalkyl groups; tri $(C_1-C_6)$alkylsilyl groups whose $(C_1-C_6)$alkyl groups may be the same or different; phenyl groups; substituted phenyl groups having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; heterocyclic groups; substituted heterocyclic groups having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or —$A^3$—$R^8$ [wherein $A^3$ is —O—, —S—, —SO—, —SO$_2$—, —N($R^6$)— (wherein $R^6$ is as defined above), —C(=O)—, —C(=NOR$^7$)— (wherein $R^7$ is as defined above), a $(C_1-C_6)$alkylene group, a halo$(C_1-C_6)$alkylene group, a $(C_2-C_6)$alkenylene group, a halo$(C_2-C_6)$alkenylene group, a $(C_2-C_6)$alkynylene group or a halo$(C_3-C_6)$alkynylene group, and $R^8$ is as follows:

(1) when $A^3$ is —O—, —S—, —SO—, —SO$_2$— or —N($R^6$)— (wherein $R^6$ is as defined above), then $R^8$ is a halo $(C_3-C_6)$cycloalkyl group; a halo$(C_3-C_6)$cycloalkenyl group; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a heterocyclic group; a substituted heterocyclic group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or $-A^4-R^9$ (wherein $A^4$ is a $(C_1-C_6)$alkylene group, a halo$(C_1-C_6)$alkylene group, a $(C_1-C_6)$alkenylene group, a halo$(C_3-C_6)$alkenylene group, a $(C_1-C_6)$alkynylene group or a halo$(C_3-C_6)$alkynylene group, and $R^9$ is a hydrogen atom; a halogen atom; a $(C_3-C_6)$cycloalkyl group; a halo$(C_3-C_6)$cycloalkyl group; a $(C_1-C_6)$alkoxycarbonyl group; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or $-A^5-R^{10}$ (wherein $A^5$ is $-O-$, $-S-$, $-SO-$, $-SO_2-$ or $-C(=O)$, and $R^{10}$ is a $(C_1-C_6)$alkyl group; a halo$(C_3-C_6)$alkyl group; a $(C_3-C_6)$alkenyl group; a halo$(C_3-C_6)$alkenyl group; a $(C_3-C_6)$cycloalkyl group; a halo$(C_3-C_6)$cycloalkyl group; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a heterocyclic group; or a substituted heterocyclic group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups)), (2) when $A^3$ is $-C(=O)-$ or $-C(=NOR^7)-$ (wherein $R^7$ is as defined above), then $R^8$ is a hydrogen atom; a $(C_1-C_6)$alkyl group; a halo$(C_1-C_6)$alkyl group; a $(C_2-C_6)$alkenyl group; a halo$(C_2-C_6)$alkenyl group; a $(C_3-C_6)$cycloalkyl group; a halo$(C_3-C_6)$cycloalkyl group; a $(C_1-C_6)$alkoxy group; a $(C_1-C_6)$alkylthio group; a mono$(C_1-C_6)$alkylamino group; a di$(C_1-C_6)$alkylamino group whose $(C_1-C_6)$alkyl groups may be the same or different; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a phenylamino group; a substituted phenylamino group having on the ring one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a heterocyclic group; or a substituted heterocyclic group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups, and (3) when $A^3$ is a $(C_1-C_6)$alkylene group, a halo$(C_1-C_6)$alkylene group, a $(C_2-C_6)$alkenylene group, a halo$(C_1-C_6)$alkenylene group, a $(C_2-C_6)$alkynylene group or a halo$(C_3-C_6)$alkynylene group, then $R^8$ is a hydrogen atom; a halogen atom; a $(C_3-C_6)$cycloalkyl group; a halo$(C_3-C_6)$cycloalkyl group; a $(C_1-C_6)$alkoxycarbonyl group; a tri$(C_1-C_6)$alkylsilyl group whose $(C_1-C_6)$alkyl groups may be the same or different; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a heterocyclic group; a substituted heterocyclic group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or $-A^6-R^{11}$ (wherein $A^6$ is $-O-$, $-S-$, $-SO-$ or $-SO_2-$, and $R^{11}$ is a $(C_3-C_6)$cycloalkyl group; a halo$(C_3-C_6)$cycloalkyl group; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a heterocyclic group; a substituted heterocyclic group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or $-A^7-R^2$ (wherein $A^7$ is a $(C_1-C_6)$alkylene group, a halo$(C_1-C_6)$alkylene group, a $(C_2-C_6)$alkenylene group, a halo$(C_2-C_6)$alkenylene group, a $(C_2-C_6)$alkynylene group or a halo$(C_3-C_6)$alkynylene group, and $R^{12}$ is a hydrogen atom; a halogen atom; a $(C_3-C_6)$cycloalkyl group; a halo$(C_3-C_6)$cycloalkyl group; a $(C_1-C_6)$alkoxy group; a halo$(C_1-C_6)$alkoxy group; a $(C_1-C_6)$alkylthio group; a halo$(C_1-C_6)$alkylthio group; a $(C_1-C_6)$alkylsulfinyl group; a halo$(C_1-C_6)$alkylsulfinyl group; a $(C_1-C_6)$alkylsulfonyl group; a halo$(C_1-C_6)$alkylsulfonyl group; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a phenoxy group; a substituted phenoxy group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a phenylthio group; a substituted phenylthio group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a heterocyclic group; or a substituted heterocyclic group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups))], and n is an integer of 0 to 3, X may form a condensed ring by combining together with the adjacent atoms in the heterocyclic ring, and said condensed ring may have one or more substituents, which may be the same or different, and are selected from halogen atoms; $(C_1-C_6)$alkyl groups; halo$(C_1-C_6)$alkyl groups; $(C_1-C_6)$alkoxy groups; halo$(C_1-C_6)$alkoxy groups; $(C_1-C_6)$alkylthio groups; halo$(C_1-C_6)$alkylthio groups; $(C_1-C_6)$alkylsulfinyl groups; halo$(C_1-C_6)$alkylsulfinyl groups; $(C_1-C_6)$alkylsulfonyl groups; halo$(C_1-C_6)$alkylsulfonyl groups; phenyl group; substituted phenyl groups having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; heterocyclic groups; and substituted heterocyclic groups having one or more substituents which may be the same or different and are selected from halogen atoms, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups, W is O, S or N-$R^{13}$ (wherein $R^{13}$ is a $(C_1-C_6)$alkyl group; a halo$(C_1-C_6)$alkyl group; a $(C_3-C_6)$alkenyl group; a halo$(C_3-C_6)$alkenyl group; a $(C_3-C_6)$alkynyl group; a halo$(C_3-C_6)$alkynyl group; a $(C_1-C_6)$alkoxy group; a phenyl group; a substituted phenyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; a phenyl$(C_1-C_6)$alkyl group; or a substituted phenyl$(C_1-C_6)$alkyl group having on the ring one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups), and p and q, which may be the same or different, are integers of 0 to 1), $B^1$, $B^2$, $B^3$ and $B^4$, which may be the same or different, are carbon atoms or nitrogen atoms, Y, which may be the same or different, are halogen atoms; cyano groups; nitro groups; halo$(C_3-C_6)$cycloalkyl groups; phenyl groups; substituted phenyl groups having one or more substituents which may be the same or different and are selected from halogen atoms, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; heterocyclic groups; substituted heterocyclic groups having one or more substituents which may be the same or different and are selected from halogen atoms, $(C_1-C_6)$alkyl groups, halo$(C_1-C_6)$ alkyl groups, $(C_1-C_6)$alkoxy groups, halo$(C_1-C_6)$ alkoxy groups, $(C_1-C_6)$alkylthio groups, halo$(C_1-C_6)$ alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or —$A^3$—$R^8$ (wherein $A^3$ and $R^8$ are as defined above), and m is an integer of 1 to 5, Y may form a condensed ring by combining together with the adjacent carbon atoms in the aromatic ring, and said condensed ring may have one or more substituents, which may be the same or different, and are selected from halogen atoms; $(C_1-C_6)$alkyl groups; halo $(C_1-C_6)$alkyl groups; $(C_1-C_6)$alkoxy groups; halo $(C_1-C_6)$alkoxy groups; $(C_1-C_6)$alkylthio groups; halo $(C_1-C_6)$alkylthio groups; $(C_1-C_6)$alkylsulfinyl groups; halo$(C_1-C_6)$alkylsulfinyl groups; $(C_1-C_6)$alkylsulfonyl groups; halo$(C_1-C_6)$alkylsulfonyl groups; phenyl group; substituted phenyl groups having one or more substituents which may be the same or different and are selected from halogen atoms, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; heterocyclic groups; and substituted heterocyclic groups having one or more substituents which may be the same or different and are selected from halogen atoms, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups and halo$(C_1-C_6)$ alkylsulfonyl groups, and each of $Z^1$ and $Z^2$ is an oxygen atom or a sulfur atom, provided that:
(1) when Het is Q2, Q6, Q7 or Q9 and $B^1$, $B^2$, $B^3$ and $B^4$ are carbon atoms at the same time, then Ym is other than 3-chloro-2-methyl group, 3-chloro-2,6-diethyl group, 5-chloro-2-methyl group, 2,6-diethyl group, 4-chloro-2-fluoro group and 2-ethyl-6-methyl group,
(2) when Het is Q4 and $B^1$, $B^2$, $B^3$ and $B^4$ are carbon atoms at the same time, then Ym is other than 2,5-dichloro group, 2,4-difluoro group, 2,6-difluoro group, 3-chloro-2-methyl group, 5-chloro-2-methyl group, 5-fluoro-2-methyl group, 2,6-dimethyl group, 2,6-diethyl group, 2-ethyl-6-methyl group, 2-methoxy-5-nitro group, 2-methoxy-5-methyl group, 2,6-diethoxy group, 3-bromo-2-methyl group, 3-fluoro-2-methyl group, 3-iodo-2-methyl group, 3-cyano-2-methyl group, 3-difluoromethoxy-2-methyl group, 5-chloro-2-ethyl group, 2,5-dimethyl group, 2,3-dichloro group, 3-chloro-2,6-diethyl group, 4-trifluoromethyl group, 3-methoxycarbonyl-2-methyl group, 3-trifluoromethyl-2-methyl group, 3,5-dichloro-2,6-diethyl group, 3,4-dichloro group, 3-(methoxycarbonylmethyloxy)-2-methyl group, 2-methyl-3-nitro group and 4-trifluoromethoxy group,
(3) when Het is Q9, $R^2$ and $R^3$ are hydrogen atoms at the same time, Xn is a 2-phenyl group, $R^1$ is a n-propyl group or an i-propyl group and $B^1$, $B^2$, $B^3$ and $B^4$ are carbon atoms at the same time, then Ym is other than 4-pentafluoroethyl-2-methyl group, and
(4) when Het is Q10 and $B^1$, $B^2$, $B^3$ and $B^4$ are carbon atoms at the same time, then Ym is other than 5-chloro-2-methyl group, 5-fluoro-2-methyl group and 2,5-dimethyl group), agricultural and horticultural insecticides and their usage.

MODE FOR CARRYING OUT THE INVENTION

In the definition of the general formula (I) for the heterocyclic dicarboxylic acid diamide derivative of the present invention, the term "halogen atom" means a chlorine atom, a bromine atom, an iodine atom or a fluorine atom. The term "$(C_1-C_6)$alkyl" means a linear or branched alkyl group of 1 to 6 carbon atoms, such as methyl, ethyl, n-propyl, i-propyl, n-butyl, i-butyl, s-butyl, t-butyl, n-pentyl, n-hexyl or the like. The term "halo$(C_1-C_6)$alkyl" means a substituted linear or branched alkyl group of 1 to 6 carbon atoms having as the substituent(s) one or more halogen atoms which may be the same or different. The term "halo $(C_3-C_6)$cycloalkyl" means a substituted alicyclic hydrocarbon group of 3 to 6 carbon atoms having as the substituent(s) one or more halogen atoms which may be the same or different. The term $(C_1-C_8)$alkylene means a linear or branched alkylene group of 1 to 8 carbon atoms, such as methylene, ethylene, propylene, trimethylene, dimethylmethylene, tetramethylene, isobutylene, dimethylethylene, octamethylene or the like. The term "heterocyclic group" means a heterocyclic group such as pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group, pyrazolyl group or the like. As to the passage "$R^1$ and $R^2$ may form a 4 to 7 membered ring by combining to each other, in which the ring may contain the same or different 1 to 3 hetero atoms selected from the group consisting of oxygen atom, sulfur atom and nitrogen atom", the 4 to 7 membered ring includes, for example, azetidine ring, pyrrolidine ring, pyrroline ring, piperidine ring, imidazolidine ring, imidazoline ring, oxazolidine ring, thiazolidine ring, isoxazolidine ring, isothiazolidine ring, tetrahydropyridine ring, piperazine ring, morpholine ring, thiomorpholine ring, dioxazine ring, dithiazine ring, indole ring, benzo[b]furan ring, benzo[b]thiophene ring, quinoline ring, isoquinoline ring, naphthyridine ring and quinoxaline ring.

As to the passage "X may form a condensed ring by combining together with the adjacent atoms in the heterocyclic ring", the condensed ring refers to, for example, indole ring, benzo[b]furan ring, benzo[b]thiophene ring, quinoline ring, isoquinoline ring, naphthyridine ring, quinoxaline ring or cinnoline ring.

As to the passage "Y may form a condensed ring by combining together with the adjacent carbon atoms in the aromatic ring", the condensed ring refers to a condensed ring such as naphthalene, tetrahydronaphthalene, indene, indan, quinoline, quinazoline, chroman, isochroman, indole, indoline, benzodioxane, benzodioxole, benzofuran, dihydrobenzofuran, benzothiophene, dihydrobenzothiophene, benzooxazole, benzothiazole, benzoimidazole, indazole or the like.

The heterocyclic dicarboxylic acid diamide derivative of the general formula (I) of the present invention contains an asymmetric carbon atom or an asymmetric center in the structural formula in some cases, and has optical isomers and diastereomers in some cases. The present invention includes all of the individual optical isomers and mixtures containing the optical isomers in any proportions. The heterocyclic dicarboxylic acid diamide derivative of the general formula (I) of the present invention has geometrical isomers due to a carbon-carbon double bond or a carbon-nitrogen double bond in the structural formula in some cases. The present invention includes all of the individual geometrical isomers and mixtures containing the geometrical isomers in any proportions.

Preferable compounds as the heterocyclic dicarboxylic acid diamide derivative of the general formula (I) of the present invention are a group of compounds in which $R^1$ is a $(C_1-C_8)$alkyl group, a $(C_1-C_6)$alkylthio$(C_1-C_8)$alkyl group, a $(C_1-C_6)$alkylsulfinyl$(C_1-C_8)$alkyl group or a $(C_1-C_6)$alkyl-sulfonyl$(C_1-C_8)$alkyl group; $R^2$ and $R^3$, which may be the same or different, are hydrogen atoms or methyl groups; Het is a pyridine ring represented by Q1, Q2, Q3 or Q4; X, which may be the same or different, are halogen atoms, nitro groups, halo$(C_1-C_6)$alkyl groups, halo $(C_1-C_6)$alkoxy groups or halo$(C_1-C_6)$alkylthio groups; n is an integer of 0 to 2; p is an integer of 0 or 1; all of $B^1$, $B^2$, $B^3$ and $B^4$ are carbon atoms, or all of $B^1$, $B^2$ and $B^4$ are carbon atoms and $B^3$ is a nitrogen atom; Y, which may be the same or different, are halogen atoms, $(C_1-C_6)$alkyl groups, halo$(C_1-C_6)$alkyl groups, halo$(C_1-C_6)$alkoxy groups, halo $(C_1-C_6)$alkylthio groups or halo$(C_1-C_6)$alkoxyhalo$(C_1-C_6)$ alkoxy groups; as to the substitution position of Y and the number m of substituents Y, the substitution is di-substitution at the 2- and 3-positions or the 2- and 4-positions in relation to the binding position of the amide group, or tri-substitution at the 2-, 3- and 4-positions or the 2-, 4- and 5-positions in relation to the binding position of the amide group; and each of $Z^1$ and $Z^2$ is an oxygen atom.

A group of more preferable compounds are compounds in which $R^1$ is an i-propyl group, a t-butyl group, a methylthio $(C_3-C_4)$alkyl group, a methylsulfinyl $(C_3-C_4)$alkyl group or a methylsulfonyl ($C_3$–$C_6$)alkyl group; each of $R^2$ and $R^3$ is a hydrogen atom; Het is a pyridine ring represented by Q1, Q2, Q3 or Q4; X is halogen atom; n is an integer of 0 to 1; p is an integer of 0 or 1; all of $B^1$, $B^2$, $B^3$ and $B^4$ are carbon atoms; Y, which may be the same or different, are chlorine atoms, methyl groups, trifluoromethyl groups, pentafluoroethyl groups, heptafluoropropyl groups, heptafluoroisopropyl groups, trifluoromethoxy groups or 1-trifluoromethyl-2,2,2-trifluoroethoxy groups; as to the substitution position of Y and the number m of substituents Y, the substitution is di-substitution at the 2- and 4-positions in relation to the binding position of the amide group; and each of $Z^1$ and $Z^2$ is an oxygen atom.

The heterocyclic dicarboxylic acid diamide derivative of the general formula (I) of the present invention can be produced, for example, by any of the production processes schematically shown below.

Production Process 1

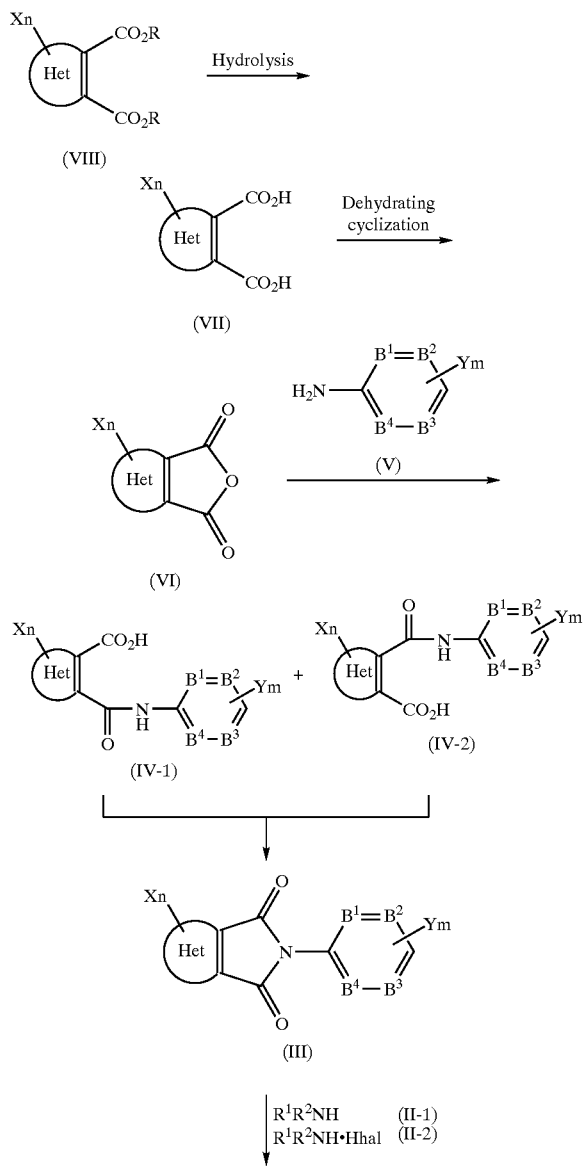

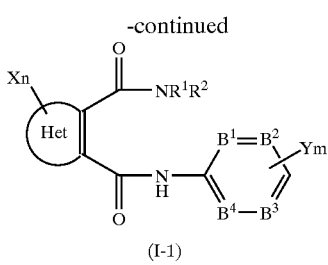

(I-1)

wherein $R^1$, $R^2$, Het, $B^1$, $B^2$, $B^3$, $B^4$, X, Y, m and n are as defined above, hal is a halogen atom, and R is a ($C_1$–$C_3$) alkyl group.

A heterocyclic dicarboxylic acid diamide derivative of the general formula (I-1) can be produced by hydrolyzing a diester of the general formula (VIII) in the presence of an acid or an alkali to obtain a dicarboxylic acid of the general formula (VII), converting said dicarboxylic acid to an acid anhydride (VI) in the presence of a dehydrating agent, reacting the acid anhydride (VI) with a substituted aromatic amine of the general formula (V) in the presence or absence of an inert solvent to obtain amides of the general formulas (IV-1) and (IV-2), reacting said amides with a dehydrating agent in the presence or absence of an inert solvent after or without isolating the amides, to obtain an imide of the general formula (III), and then reacting said imide with an amine or its salt of the general formula (II-1) or the general formula (II-2), respectively, in the presence or absence of an inert solvent after or without isolating the imide.

(1-1). General Formula (VIII)→General Formula (VII)

As an inert solvent usable in this reaction, there can be used, for example, water, alcohols (e.g. methanol, ethanol and propanol) as water-soluble solvents, and mixed solvents of water and water-soluble solvents.

As the base used for the hydrolysis, hydroxides of alkali metals, such as sodium hydroxide, potassium hydroxide and the like can be used. As to the amount of the base used, the base may be used in an amount properly chosen in the range of 2 to 10 equivalents per equivalent of the diester of the general formula (VIII). As the acid, there can be used, for example, inorganic acids such as hydrochloric acid, sulfuric acid, etc.; and organic acids such as trifluoroacetic acid, etc. The amount of the acid used may be a catalytic amount relative to the diester of the general formula (VIII) and ranges from 0.001 to 0.1 equivalent per equivalent of the diester.

As to the reaction temperature, the reaction can be carried out at room temperature or while refluxing the inert solvent used. Although the reaction time is varied depending on the scale of reaction, the reaction temperature and the like, the reaction may be carried out for a time properly chosen in the range of several minutes to 48 hours.

After completion of the reaction, the desired compound is isolated from the reaction system containing the desired compound by a conventional method, and if necessary, purified by a recrystallization method, a distillation method, a column chromatographic method, etc., whereby the desired compound can be produced.

It is also possible to subject the desired compound to the subsequent reaction without isolation after completion of the reaction.

(1-2). General Formula (VII)→General Formula (VI)

As an inert solvent usable in this reaction, any inert solvent may be used so long as it does not markedly inhibit the progress of the reaction. There can be used, for example, halogenated hydrocarbons such as dichloromethane, chloroform, carbon tetrachloride, etc.; aromatic hydrocarbons such as benzene, toluene, xylene, chlorobenzene, etc.; acyclic or cyclic ethers such as Methyl Cellosolves, diethyl ether, diisopropyl ether, dioxane, tetrahydrofuran, etc.; and organic acids such as acetic acid, trifluoroacetic acid, etc. These inert solvents may be used singly or as a mixture thereof.

The dehydrating agent may be used in excess to serve also as the inert solvent.

As the dehydrating agent, there can be used dehydrating agents such as acetic anhydride, trifluoroacetic anhydride, etc. As to the amount of these dehydrating agents used, they may be used in an amount properly chosen in the range of 1 mole to excess moles per mole of the compound of the general formula (VII), and they are preferably used in an amount equimolar with the amount of the compound of the general formula (VII).

The reaction temperature may be properly chosen in the range of room temperature to the boiling point of the inert solvent used. When no inert solvent is used, it is sufficient that the reaction is carried out below the boiling point of the dehydrating agent used.

Although the reaction time is varied depending on the reaction temperature, the scale of reaction, and the like, the reaction may be carried out in the range of several minutes to 48 hours.

After completion of the reaction, the desired compound is isolated from the reaction system containing the desired compound by a conventional method, and if necessary, purified by a recrystallization method, a distillation method, a column chromatographic method, etc., whereby the desired compound can be produced.

It is also possible to subject the desired compound to the subsequent reaction without isolation after completion of the reaction.

(1-3). General Formula (VI)→General Formula (IV-1)+ General Formula (IV-2)

As the inert solvent usable in this reaction, any inert solvent may be used so long as it does not markedly inhibit the progress of the reaction. There can be exemplified inert solvent including aromatic hydrocarbons such as benzene, toluene, xylene, etc.; halogenated hydrocarbons such as dichloromethane, chloroform, carbon tetrachloride, chlorobenzene, dichlorobenzene, etc.; acyclic or cyclic ethers such as diethyl ether, dioxane, tetrahydrofuran, etc.; esters such as ethyl acetate, etc.; amides such as dimethylformamide, dimethylacetamide, etc.; acids such as acetic acid, etc.; dimethyl sulfoxide; 1,3-dimethyl-2-imidazolidinone; and water. These inert solvents may be used singly or as a mixture of two or more thereof.

Since the reaction is an equimolar reaction, it is sufficient that the reactants are used in equimolar amounts, though either of them may be used in excess. If necessary, the reaction may be carried out under dehydrating conditions.

As to the reaction temperature, the reaction can be carried out at room temperature or while refluxing the inert solvent used. Although the reaction time is varied depending on the scale of reaction, the reaction temperature and the like, the reaction may be carried out for a time properly chosen in the range of several minutes to 48 hours.

After completion of the reaction, the desired compounds are isolated from the reaction system containing the desired compounds by a conventional method, and if necessary, purified by a recrystallization method, a distillation method, a column chromatographic method, etc., whereby the desired compounds can be produced.

It is also possible to subject the desired compounds to the subsequent reaction without isolation after completion of the reaction.

(1-4). General Formula (IV-1)+General Formula (IV-2)→ General Formula (III)

In the case of this reaction, the desired compound can be produced in a manner similar to that described in (1-2).

It is also possible to subject the desired compounds to the subsequent reaction without isolation after completion of the reaction.

(1-5). General Formula (III)→General Formula (I-1)

As the inert solvent usable in this reaction, pyridines can be used besides, for example, the inert solvents exemplified in (1-2).

Since the reaction is an equimolar reaction, it is sufficient that the amine of the general formula (II-1) or the amine salt of the general formula (II-2) is used in an amount equimolar with the amount of the imide of the general formula (III), though the amine or the amine salt may be used in excess.

When the amine salt of the general formula (II-2) is used in the reaction, a base is necessary in order to produce free amine in the reaction system. As the base, an inorganic base or an organic base can be used. The inorganic base includes, for example, hydroxides and carbonates of alkali metals, such as sodium hydroxide, potassium hydroxide, sodium carbonate and potassium carbonate. The organic base includes, for example, triethylamine, pyridine, 4-(dimethylamino)pyridine and 1,8-diazabicyclo[5.4.0]-7-undecene. As to the amount of these bases used, they may be used in an amount properly chosen in the range of 1 mole to excess moles per mole of the amine salt of the general formula (II-2).

The reaction temperature may be properly chosen in the range of $-10°$ C. to the boiling point of the inert solvent used, and the reaction is preferably carried out in the range of $0°$ C. to $150°$ C.

Although the reaction time is varied depending on the reaction temperature, the scale of reaction, and the like, the reaction may be carried out in the range of several minutes to 48 hours.

After completion of the reaction, the desired compound is isolated from the reaction system containing the desired compound by a conventional method, and if necessary, purified by a recrystallization method, a distillation method, a column-chromatographic method, etc., whereby the desired compound can be produced.

The compound of the general formula (VIII), i.e., the starting material in the reaction can be produced according to a well-known process, for example, the processes described in, for instance, J. Am. Chem. Soc., 63, 1762 (1941), J. Heterocyclic Chem., 21, 1431 (1984), J. Indian Chem. Soc., 1982, 1372, J. Org. Chem., 14, 723 (1949), Heterocycles, 27, 1489 (1988), J. Am. Chem. Soc., 78, 2220 (1956), J. Prakt. Chem., 311, 807 (1969), Tetrahedron, 36, 1801 (1980), JP-A-6-122684, U.S. Pat. No. 3,414,580, ditto 3,686,171, J. Med. Chem., 27, 1396 (1984), J. Heterocyclic Chem., 12, 1303 (1975)., ditto 15, 1477 (1978), ditto 16, 1141 (1979), ditto 17, 443 (1982), ditto 21, 689 (1984), Beil., 25III, 2028, JP-A-52-77086, J. Am. Chem. Soc., 81, 2456 (1956), J. Org. Chem., 37, 3224 (1972), JP-A-62-175480, JP-A-62-230782, JP-A-60-69083, JP-A-60-185783, JP-A-61-109790, JP-A-62-277385, JP-A-63-295575, JP-A-63-99067, JP-A-64-75474, JP-A-64-90118, Yakugaku Zasshi, 84, 416 (1964), Chem. and Pharm. Bull., 5, 277 (1957), Chem. Research (S), 1989, 196, Chem. Pharm. Bull., 2, (7), 1513 (1972), J. Heterocyclic Chem., 27, 579 (1990), Tetrahedron, 53 (42), 14497 (1997), ditto 41 (7), 1199 (1985), Chem. Ber., 107, 3036 (1974), J. Heterocyclic Chem., 23, 1103 (1986), ditto 5, 125 (1968), J. Org. Chem., 26, 468 (1961), etc.

Production Process 2

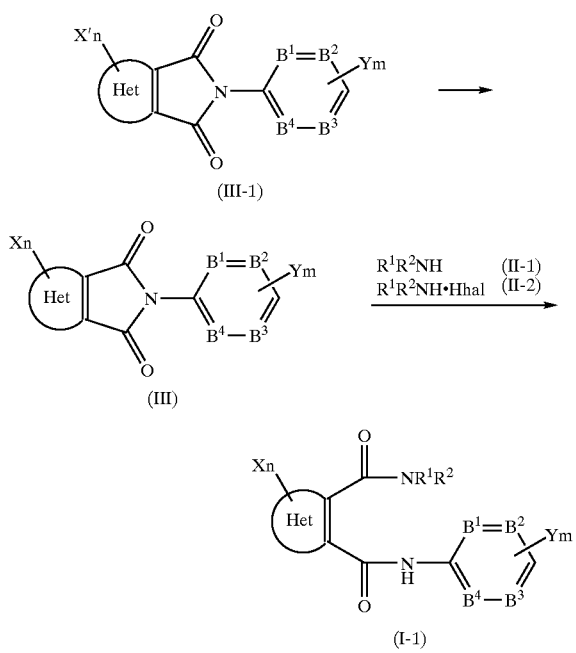

wherein $R^1$, $R^2$, Het, $B^1$, $B^2$, $B^3$, $B^4$, X, Y, hal, m and n are as defined above, and X' is a halogen atom or a nitro group, provided that X is other than hydrogen atom and nitro group.

A heterocyclic dicarboxylic acid diamide derivative of the general formula (I-1) can be produced by reacting a heterocyclic dicarboxylic acid imide derivative of the general formula (III-1) with a reactant corresponding to X, in the presence of an inert solvent to obtain a heterocyclic dicarboxylic acid imide derivative of the general formula (III), and reacting said heterocyclic dicarboxylic acid imide derivative (III) with an amine or its salt of the general formula (II-1) or the general formula (II-2), respectively, after or without isolating the derivative (III).

(2-1). General Formula (III-1)→General Formula (III)

In the case of this reaction, the production can be carried out according to the process described in J. Org. Chem., 42, 3415 (1977), Tetrahedron, 25, 5921 (1969), Synthesis, 1984, 667, Chem. Lett., 1973, 471, J. Org. Chem., 39, 3318 (1974), ditto 39, 3327 (1974), etc.

(2-2). General Formula (III)→General Formula (I-1)

In the case of this reaction, the production can be carried out according to production process (1-5).

Production Process 3

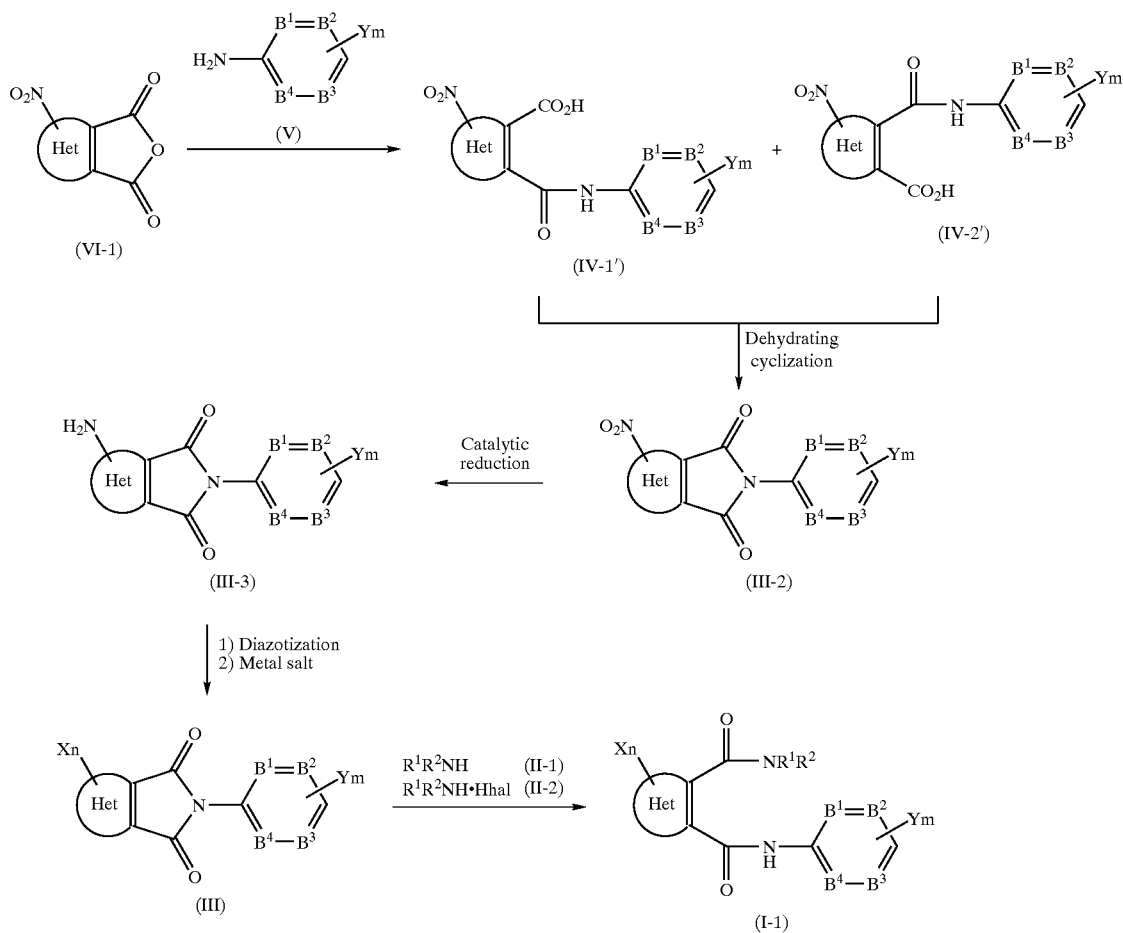

wherein $R^1$, $R^2$, Het, $B^1$, $B^2$, $B^3$, $B^4$, X, Y, hal, m and n are as defined above.

A heterocyclic dicarboxylic acid diamide derivative of the general formula (I-1) can be produced by reacting a heterocyclic dicarboxylic acid anhydride derivative of the general formula (VI-1) with an aromatic amine of the general formula (V) in the presence of an inert solvent to obtain amides of the general formulas (IV-1') and (IV-2'), reacting said amides with a dehydrating agent in the presence or absence of an inert solvent after or without isolating the amides, to obtain a heterocyclic dicarboxylic acid imide derivative of the general formula (III-2), subjecting said heterocyclic dicarboxylic acid imide derivative (III-2) to catalytic reduction with hydrogen after or without isolation to obtain a heterocyclic dicarboxylic acid imide derivative of the general formula (III-3), diazotizing said heterocyclic dicarboxylic acid imide derivative (III-3) after or without isolation, adding a metal salt thereto to obtain a heterocyclic dicarboxylic acid imide derivative of the general formula (III), and then reacting said heterocyclic dicarboxylic acid imide derivative (III) with an amine or its salt of the general formula (II-1) or the general formula (II-2), respectively, after or without isolating the derivative (III).

(3-1). General Formula (VI-1)→General Formula (IV-1')+ General Formula (IV-2')

In the case of this reaction, the desired compound can be produced in a manner similar to that described in production process (1-3).

(3-2). General Formula (IV-1')+General Formula (IV-2')→ General Formula (III-2)

In the case of this reaction, the desired compound can be produced in a manner similar to that described in production process (1-4).

(3-3). General Formula (III-2)→General Formula (III-3)

As an inert solvent usable in this reaction, any inert solvent may be used so long as it does not markedly inhibit the progress of the reaction. There can be exemplified alcohols such as methanol, ethanol, propanol, etc.; acyclic or cyclic ethers such as diethyl ether, dioxane, tetrahydrofuran, etc.; and acids such as acetic acid, etc. These inert solvents may be used singly or as a mixture of two or more thereof.

As a catalyst for the catalytic reduction used in the reaction, there can be exemplified palladium-carbon, Raney nickel, palladium black and platinum black. As to the amount of the catalyst used, the catalyst may be used in an amount properly chosen in the range of 0.1 to 10 wt % based on the weight of the heterocyclic dicarboxylic acid imide derivative of the general formula (III-2). The reaction is carried out under a hydrogen atmosphere, and the reaction may be carried out at a hydrogen pressure properly chosen in the range of 1 to 10 atmospheric pressure.

As to the reaction temperature, the reaction may be carried out at room temperature to the reflux temperature of the inert solvent used. Although the reaction time is varied depending on the scale of reaction, the reaction temperature and the like, it may be properly chosen in the range of several minutes to 48 hours.

After completion of the reaction, the desired compound is isolated from the reaction system containing the desired compound by a conventional method, and if necessary, purified by recrystallization, column chromatography, etc., whereby the desired compound can be produced. It is also possible to subject the desired compound to the subsequent reaction without isolation from the reaction system.

(3-4). General Formula (III-3)→General Formula (III)

As an inert solvent used in this reaction, acidic solvents can be used. There can be exemplified an aqueous hydrochloric acid solution, an aqueous hydrobromic acid solution, an aqueous hydroiodic acid solution, an aqueous sulfuric acid solution, acetic acid and trifluoroacetic acid. These acidic solvents may be used singly or as a mixture of two or more thereof. In addition, these acidic solvents may be used in admixture with ethers such as tetrahydrofuran, dioxane, etc.

As a diazotizing agent, there can be exemplified diazotizing agents such as sodium nitrite, nitrosyl hydrogensulfate, alkyl nitrites, etc. As to the amount of these diazotizing agents used, the reaction may be carried out by properly choosing the amount in the range of an amount equal to that of the heterocyclic dicarboxylic acid imide derivative of the general formula (III-3) to an excess amount over this derivative.

As to the reaction temperature, the reaction may be carried out at −50° C. to room temperature or at the reflux temperature of the inert solvent used. Although the reaction time is varied depending on the scale of reaction, the reaction temperature and the like, it may be properly chosen in the range of several minutes to 48 hours.

As the metal salt added after the production of the diazonium salt, there can be used metal salts such as cuprous chloride, cuprous bromide, potassium iodide, copper cyanide, potassium xanthate, mercaptan sodium, etc. As to the amount of the metal salt used, the reaction may be carried out by properly choosing the amount in the range of 1 equivalent to excess equivalents per equivalent of the heterocyclic dicarboxylic acid imide derivative of the general formula (III-3).

After completion of the reaction, the desired compound is isolated from the reaction system containing the desired compound by a conventional method, and if necessary, purified by recrystallization, column chromatography, etc., whereby the desired compound can be produced. It is also possible to subject the desired compound to the subsequent reaction without isolation from the reaction system.

In the case of the reaction, the production can be carried out according to the process described in Org. Synth., IV, 160 (1963), ditto III, 809 (1959), J. Am. Chem. Soc., 92, 3520 (1970), etc.

C. (3-5). General Formula (III)→General Formula (I-1)

In the case of this reaction, the desired compound can be produced in a manner similar to that described in production process (1-5).

Production Process 4

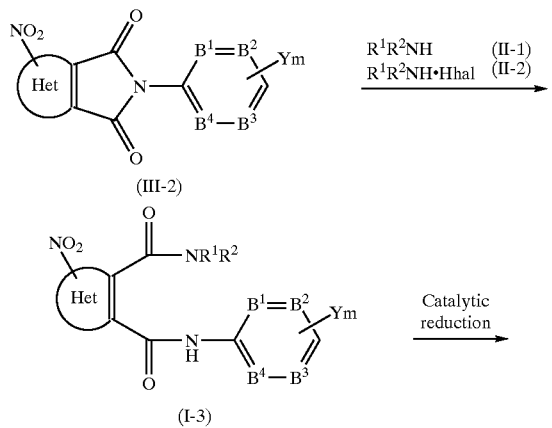

-continued

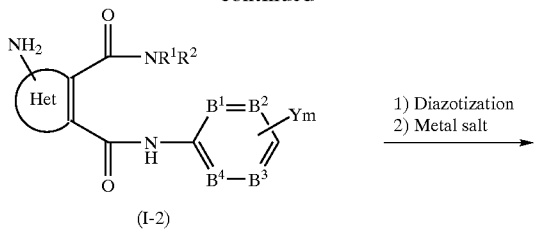

wherein $R^1$, $R^2$, Het, $B^1$, $B^2$, $B^3$, $B^4$, X, Y, hal, m and n are as defined above.

A heterocyclic dicarboxylic acid diamide derivative of the general formula (I-1) can be produced by reacting a heterocyclic dicarboxylic acid imide derivative of the general formula (III-2) with an amine or its salt of the general formula (II-1) or the general formula (II-2), respectively, in the presence of an inert solvent to obtain a heterocyclic dicarboxylic acid diamide derivative of the general formula (I-3), subjecting said heterocyclic dicarboxylic acid diamide derivative (I-3) to catalytic reduction with hydrogen after or without isolation to obtain a heterocyclic dicarboxylic acid diamide derivative of the general formula (I-2), diazotizing said heterocyclic dicarboxylic acid diamide derivative (I-2) after or without isolation, and then adding a metal salt thereto.

(4-1). General Formula (III-2)→General Formula (I-3)

In the case of this reaction, the desired compound can be produced in a manner similar to that described in production process (1-5).

(4-2). General Formula (I-3)→General Formula (I-2)

In the case of this reaction, the desired compound can be produced in a manner similar to that described in production process (3-3).

(4-3). General Formula (I-2)→General Formula (I-1)

In the case of this reaction, the desired compound can be produced in a manner similar to that described in production process (3-4).

Production Process 5

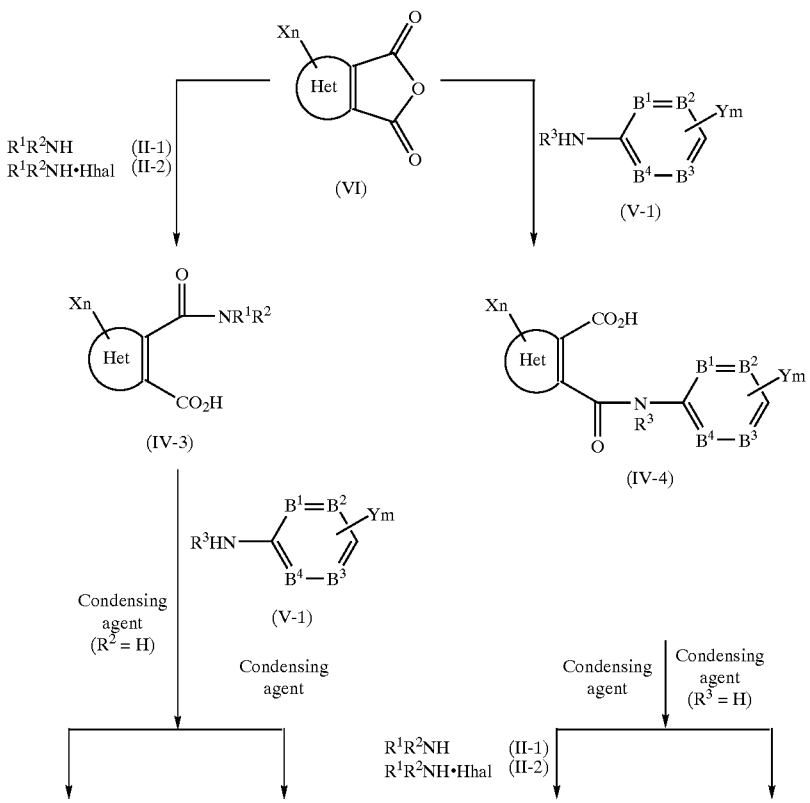

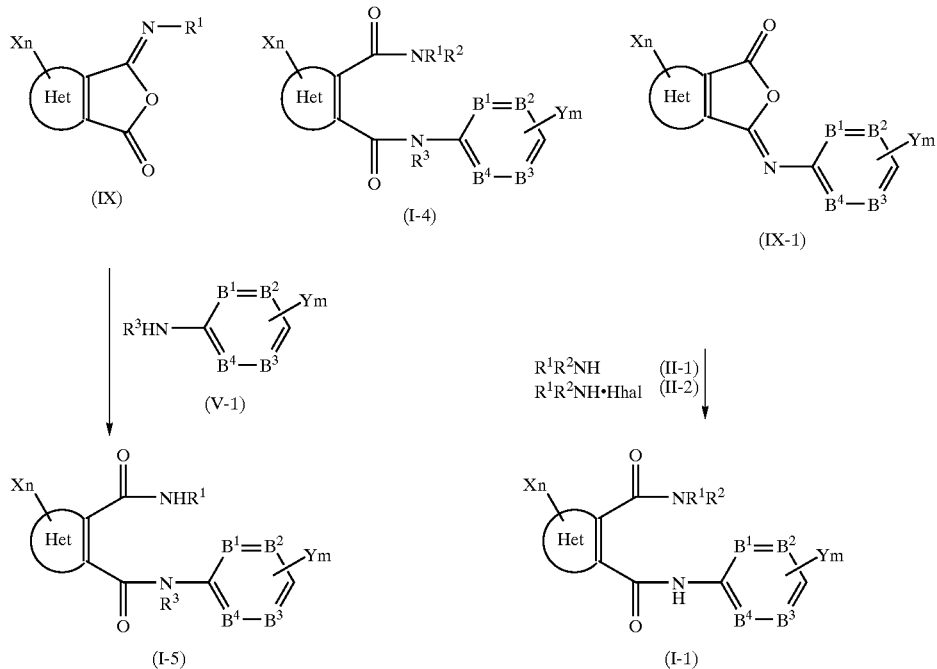

wherein $R^1$, $R^2$, $R^3$, Het, $B^1$, $B^2$, $B^3$, $B^4$, X, Y, m and n are as defined above.

A heterocyclic dicarboxylic acid diamide derivative of the general formula (I-5) or the general formula (I-4) can be produced by reacting a heterocyclic dicarboxylic acid anhydride of the general formula (VI) with an amine or its salt of the general formula (II-1) or the general formula (II-2), respectively, in the presence of an inert solvent to obtain a heterocyclic dicarboxylic acid amide of the general formula (IV-3), and treating said heterocyclic dicarboxylic acid amide after or without isolation as follows: when its $R^2$ is a hydrogen atom, the heterocyclic dicarboxylic acid amide (IV-3) is subjected to condensation reaction in the presence of a condensing agent to obtain a compound of the general formula (IX), and said compound (IX) is reacted with an aromatic amine of the general formula (V-1) in the presence of an inert solvent after or without isolating the compound (IX); or when its $R^2$ is other than a hydrogen atom, the heterocyclic dicarboxylic acid amide (IV-3) is condensed with an aromatic amine of the general formula (V-1) in the presence of a condensing agent.

Alternatively, a heterocyclic dicarboxylic acid diamide derivative of the general formula (I-1) or the general formula (I-4) can be produced by reacting a heterocyclic dicarboxylic acid anhydride of the general formula (VI) with an aromatic amine of the general formula (V-1) in the presence of an inert solvent to obtain a heterocyclic dicarboxylic acid amide of the general formula (IV-4), and treating said heterocyclic dicarboxylic acid amide (IV-4) after or without isolation as follows: when its $R^3$ is a hydrogen atom, the heterocyclic dicarboxylic acid amide (IV-4) is subjected to condensation reaction in the presence of a condensing agent to obtain a compound of the general formula (IX-1), and said compound (IX-1) is reacted with an amine or its salt of the general formula (II-1) or the general formula (II-2), respectively, in the presence of an inert solvent after or without isolating the compound (IX-1); or when its $R^3$ is other than a hydrogen atom, the heterocyclic dicarboxylic acid amide (IV-4) is condensed with an amine or its salt of the general formula (II-1) or the general formula (II-2), respectively, in the presence of a condensing agent.

(5-1). General Formula (VI)→General Formula (IV-3) or General Formula (IV-4)

In the case of this reaction, the desired compound can be produced in a manner similar to that described in production process (1-3).

(5-2). General Formula (IV-3)→General Formula (IX) or General Formula (IV-4)→General Formula (IX-1)

In the case of this reaction, the desired compound can be produced according to the process described in J. Med. Chem., 10, 982 (1967).

(5-3). General Formula (IV-3) or General Formula (IV-4)→ General Formula (I-4)

The production can be carried out by reacting a heterocyclic dicarboxylic acid amide derivative of the general formula (IV-3) or the general formula (IV-4) with an amine of the general formula (II-1) or (II-2) or the general formula (V-1) in the presence of a condensing agent and an inert solvent. It is also possible to carry out the reaction in the presence of a base if necessary.

The inert solvent used in the reaction includes, for example, tetrahydrofuran, diethyl ether, dioxane, chloroform and dichloromethane. As the condensing agent used in the reaction, any condensing agent may be used so long as it is used in conventional amide synthesis. The condensing agent includes, for example, Mukaiyama reagent (2-chloro-N-methylpyridinium iodide), DCC (1,3-dicyclohexylcarbodiimide), CDI (carbonyl diumidazole) and DEPC (diethyl cyanophosphonate). As to the amount of the condensing agent used, the condensing agent may be used in an amount properly chosen in the range of 1 mole to excess moles per mole of the heterocyclic dicarboxylic acid amide derivative of the general formula (IV-3) or the general formula (IV-4).

The base usable in the reaction includes, for example, organic bases such as triethylamine, pyridine, etc.; and inorganic bases such as potassium carbonate. As to the amount of the base used, the base may be used in an amount properly chosen in the range of 1 mole to excess moles per mole of the heterocyclic dicarboxylic acid amide derivative of the general formula (IV-3) or the general formula (IV-4).

As to the reaction temperature, the reaction may be carried out at 0° C. to the boiling point of the inert solvent used. Although the reaction time is varied depending on the scale of reaction, the reaction temperature and the like, it ranges from several minutes to 48 hours.

After completion of the reaction, the desired compound is isolated from the reaction system containing the desired compound by a conventional method, and if necessary, purified by recrystallization, column chromatography, etc., whereby the desired compound can be produced.

(5-4). General Formula (IX)→General Formula (I-5) or General Formula (IX-1)→General Formula (I-1)

In the case of this reaction, the desired compound can be produced in a manner similar to that described in production process (1-5).

Production Process 6

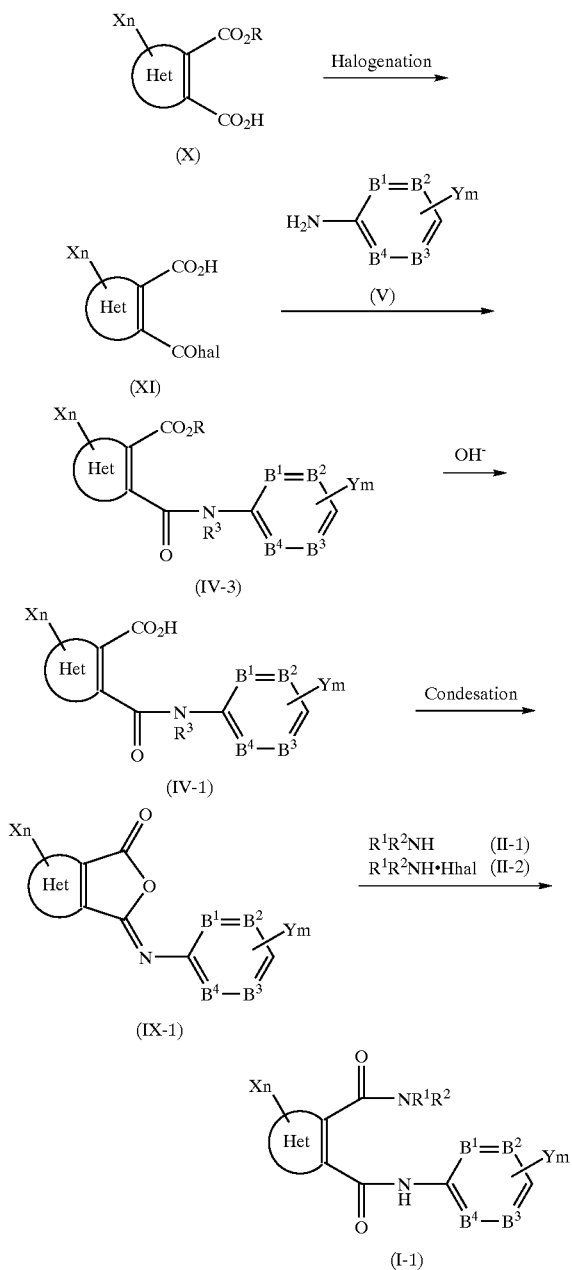

wherein R, $R^1$, $R^2$, Het, $B^1$, $B^2$, $B^3$, $B^4$, X, Y, hal, m and n are as defined above.

A heterocyclic dicarboxylic acid diamide derivative of the general formula (I-1) can be produced by halogenating a heterocyclic dicarboxylic acid ester derivative of the general formula (X) in the presence or absence of an inert solvent to obtain a heterocyclic dicarboxylic acid halide of the general formula (XI), reacting said heterocyclic dicarboxylic acid halide (XI) with an aromatic amine of the general formula (V) in the presence of an inert solvent and a base after or without isolating the halide (XI), to obtain a heterocyclic dicarboxylic acid amide of the general formula (IV-3), hydrolyzing said heterocyclic dicarboxylic acid amide (IV-3) in the presence or absence of an inert solvent after or without isolating the amide (IV-3), to obtain a heterocyclic dicarboxylic acid amide of the general formula (IV-1), subjecting said heterocyclic dicarboxylic acid amide (IV-1) to condensation reaction after or without isolation to obtain a heterocyclic dicarboxylic acid isoimide derivative of the general formula (IX-1), reacting said heterocyclic dicarboxylic acid isoimide derivative (IX-1) with an amine or its salt of the general formula (II-1) or the general formula (II-2), respectively.

(6-1). General Formula (X)→General Formula (XI)

As the inert solvent usable in this reaction, any inert solvent may be used so long as it does not markedly inhibit the progress of the reaction. There can be exemplified inert solvents including aromatic hydrocarbons such as benzene, toluene, xylene, etc.; halogenated hydrocarbons such as dichloromethane, chloroform, carbon tetrachloride, etc.; chlorinated aromatic hydrocarbons such as chlorobenzene, dichlorobenzene, etc.; acyclic or cyclic ethers such as diethyl ether, dioxane, tetrahydrofuran, etc.; and esters such as ethyl acetate, etc. These inert solvents may be used singly or as a mixture of two or more thereof.

As a halogenating agent, there can be used halogenating agents such as thionyl chloride, phosphorus oxychloride, phosphorus trichloride, etc. As to the amount of the halogenating agent used, the halogenating agent may be used in an amount properly chosen in the range of 1 to 10 equivalents per equivalent of the heterocyclic dicarboxylic acid ester derivative of the general formula (X).

As to the reaction temperature, the reaction may be carried out at 0° C. to the reflux temperature of the inert solvent used. Although the reaction time is varied depending on the scale of reaction, the reaction temperature and the like, it may be properly chosen in the range of several minutes to 48 hours.

After completion of the reaction, the desired compound is isolated from the reaction system containing the desired compound by a conventional method, and if necessary, purified by recrystallization, column chromatography, etc., whereby the desired compound can be produced. It is also possible to subject the desired compound to the subsequent reaction without isolation from the reaction system.

(6-2). General Formula (XI)→General Formula (IV-3)

As the inert solvent usable in this reaction, there can be used, for example, the inert solvents exemplified in production process (1-3).

As the base, an inorganic base or an organic base can be used. As the inorganic base, there can be used, for example, hydroxides of alkali metals, such as sodium hydroxide, potassium hydroxide, etc. As the organic base, organic bases such as triethylamine, pyridine and the like can be used. As to the amount of the base used, the base may be used in an amount properly chosen in the range of 0.5 to 3 equivalents per equivalent of the heterocyclic dicarboxylic acid halide of the general formula (XI).

Since the reaction is an equimolar reaction, it is sufficient that the reactants are used in equimolar amounts, though the reaction may be carried out by properly choosing the amount of the aromatic amine of the general formula (V) in the range of 0.5 to 2 equivalents per equivalent of the aromatic dicarboxylic acid halide of the general formula (XI).

As to the reaction temperature, the reaction may be carried out at 0° C. to the reflux temperature of the inert solvent used. Although the reaction time is varied depending on the scale of reaction, the reaction temperature and the like, it may be properly chosen in the range of several minutes to 48 hours.

After completion of the reaction, the desired compound is isolated from the reaction system containing the desired compound by a conventional method, and if necessary, purified by recrystallization, column chromatography, etc., whereby the desired compound can be produced. It is also possible to subject the desired compound to the subsequent reaction without isolation from the reaction system.

(6-3). General Formula (IV-3)→General Formula (IV-1)

In the case of this reaction, the desired compound can be produced according to production process (1-1).

(6-4). General Formula (IV-1)→General Formula (IX-1)

In the case of this reaction, the desired compound can be produced according to production process (5-2).

(6-5). General Formula (IX-1)→General Formula (I-1)

In the case of this reaction, the desired compound can be produced according to production process (I-5).

Production Process 7

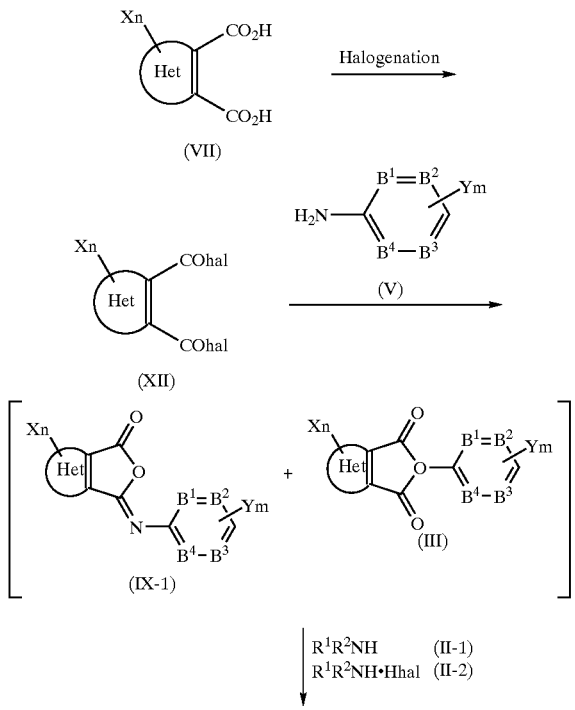

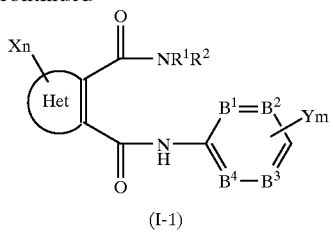

wherein $R^1$, $R^2$, Het, $B^1$, $B^2$, $B^3$, $B^4$, X, Y, hal, m and n are as defined above.

A heterocyclic dicarboxylic acid diamide derivative of the general formula (I-1) can be produced by halogenating a heterocyclic dicarboxylic acid of the general formula (VII) in the presence of a halogenating agent to obtain an acid halide of the general formula (XII), reacting said acid halide (XII) with a substituted aromatic amine of the general formula (V) in the presence or absence of an inert solvent to obtain a heterocyclic dicarboxylic acid isoimide and a heterocyclic dicarboxylic acid imide of the general formulas (IX-1) and (III), respectively, and reacting these compounds with an amine or its salt of the general formula (II-1) or the general formula (II-2), respectively, in the presence or absence of an inert go solvent after or without isolating said compounds.

(7-1). General Formula (VII)→General Formula (XII)

In the case of this reaction, the desired compound can be produced according to production process (6-1).

(7-2). General Formula (XII)→General Formulas (IX-1) and (III)

In the case of this reaction, the desired compound can be produced in a manner similar to that described in production process (6-2).

(7-3). General Formulas (IX-1) and (III)→General Formula (I-1)

In the case of this reaction, the desired compound can be produced in a manner similar to that described in production process (1-5).

Production Process 8

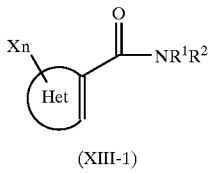

(XIII-1)

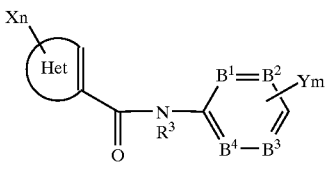

(XIII-2)

1) n-BuLi
2) $CO_2$ 1) n-BuLi
2) $CO_2$

-continued

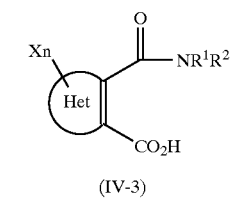
(IV-3)

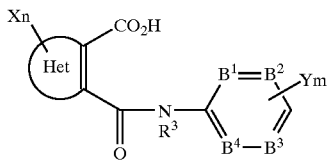
(IV-4)

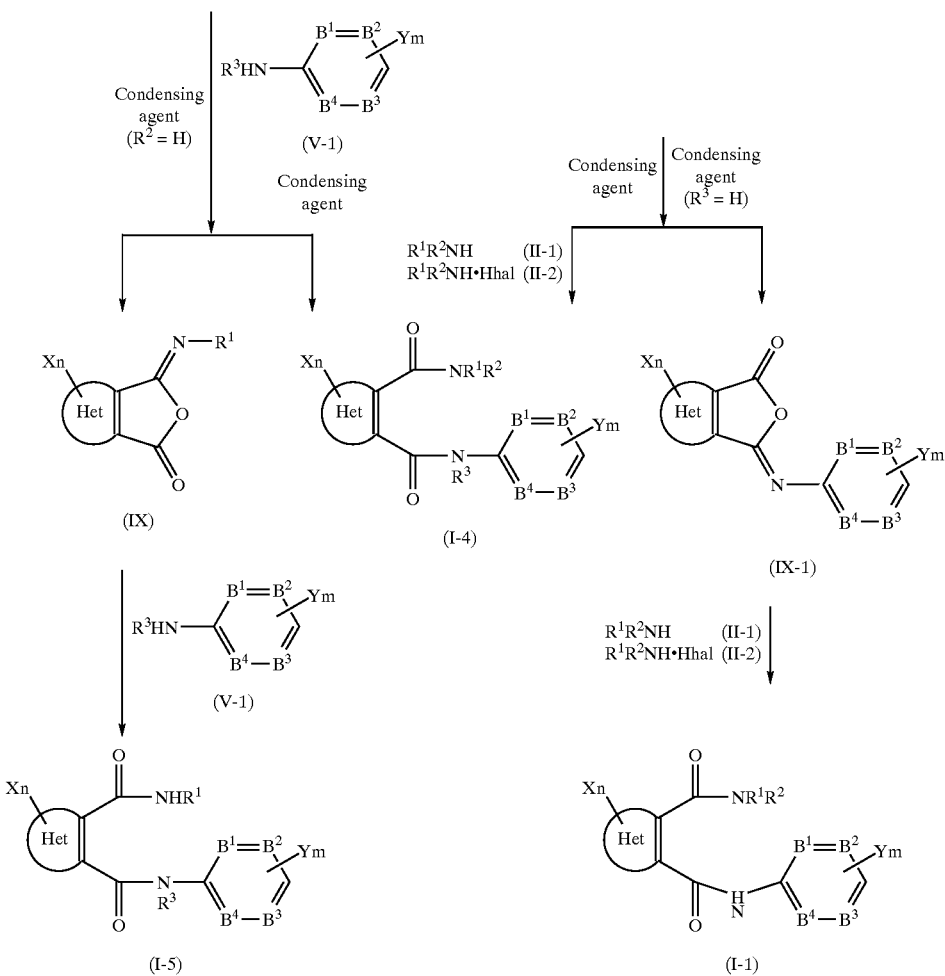

wherein $R^1$, $R^2$, Het, $B^1$, $B^2$, $B^3$, $B^4$, X, Y, hal, m and n are as defined above.

A heterocyclic dicarboxylic acid diamide derivative of the general formula (I-1), (I-4) or (1-5) can be produced by subjecting a heterocyclic carboxylic acid amide of the general formula (XIII-1) or the general formula (XIII-2) to ortho-metallation by the use of a metal reagent such as butyllithium, reacting the ortho-metallation product with carbon dioxide to obtain a heterocyclic dicarboxylic acid amide derivative of the general formula (IV-3) or the general formula (IV-4), and treating this derivative in the same manner as in production processes (5-2) to (5-4).

(8-1). General Formula (XIII-1) or General Formula (XIII-2)→General Formula (IV-3) or General Formula (IV-4)

In the case of this reaction, the production can be carried out by lithiation at the ortho-position according to the method described in J. Org. Chem., 29, 853 (1964) and then introducing carbon dioxide to replace the lithium therewith at −80° C. to room temperature.

After completion of the reaction, the desired compound is isolated from the reaction system containing the desired compound by a conventional method, and if necessary, purified by recrystallization, column chromatography, etc., whereby the desired compound can be produced.

Production Process 9

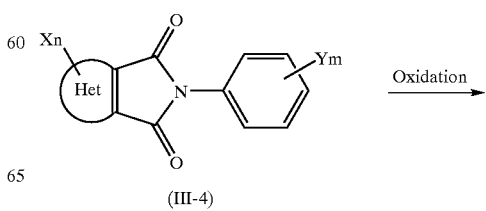
(III-4)

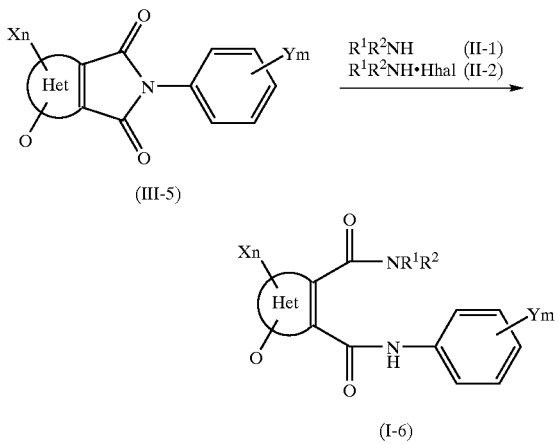

(III-5)

(I-6)

wherein $R^1$, $R^2$, Het, X, Y, hal, m and n are as defined above.

The reaction is oxidation of the nitrogen atom in the heterocyclic ring. A heterocyclic dicarboxylic acid diamide derivative of the general formula (I-6) can be produced by reacting a heterocyclic dicarboxylic acid imide of the general formula (III-4) with an oxidizing agent in the presence of an inert solvent to obtain a heterocyclic dicarboxylic acid imide derivative of the general formula (III-5), and reacting said heterocyclic dicarboxylic acid imide derivative (III-5) with an amine or its salt of the general formula (II-1) or the general formula (II-2), respectively, after or without isolating the derivative (III-5).

(9-1). General Formula (III-4)→General Formula (III-5)

As the inert solvent usable in this reaction, any inert solvent may be used so long as it does not inhibit the progress of the reaction. There can be exemplified dichloromethane, chloroform, carbon tetrachloride, chlorobenzene, water, acetic acid, ethyl acetate and trifluoroacetic acid. These inert solvents may be used singly or as a mixture of two or more thereof.

As the oxidizing agent used in the reaction, hydrogen peroxide, m-chloroperbenzoic acid and peracetic acid can be exemplified.

As to the reaction temperature for said reaction, the reaction may be carried out at 0° C. to 100° C. Although the reaction time is varied depending on the scale of reaction, the reaction temperature and the like, it may be properly chosen in the range of several minutes to 48 hours.

(9-2). General Formula (III-5)→General Formula (I-6)

In the case of this reaction, the production can be carried out according to production process (I-5).

Typical examples of the heterocyclic dicarboxylic acid diamide derivative of the general formula (I) of the present invention are given in Tables 1 to 33 but they are not intended in any way to limit the scope of the present invention.

General Formula (I)

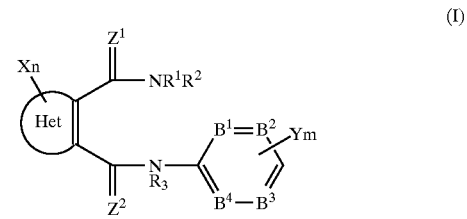

(I)

TABLE 1

($Z^1 = Z^2 = O$, $R^3 = H$, Het = Q1, $B^1 = B^2 = B^3 = B^4 = C$)

| No | $R^1$ | $R^2$ | p | Xn | Ym | Physical property m.p. ° C. |
|---|---|---|---|---|---|---|
| 1 | H | H | 0 | H | 2-$CH_3$-4-$CF_2CF_3$ | |
| 2 | $CH_3$ | H | 0 | H | 4-$CF_3$ | |
| 3 | $CH_3$ | H | 0 | H | 2-$CH_3$-4-Cl | |
| 4 | $CH_3$ | H | 0 | H | 2-$CH_3$-4-$OCHF_2$ | |
| 5 | $CH_3$ | H | 0 | H | 2-$CH_3$-4-$CF_2CF_3$ | |
| 6 | $CH_3$ | H | 0 | H | 2-$CH_3$-4-$OCF_3$ | |
| 7 | $C_2H_5$ | H | 0 | H | 2-$CH_3$-4-$CF_3$ | |
| 8 | $C_2H_5$ | H | 0 | H | 2-$CH_3$-4-$OCHF_2$ | |
| 9 | $C_2H_5$ | H | 0 | H | 2-$CH_3$-4-$OCF_3$ | |
| 10 | $C_2H_5$ | H | 0 | H | 2-$CH_3$-4-$CF_2CF_3$ | |
| 11 | $C_2H_5$ | H | 0 | H | 2-$CH_3$-4-$CF(CF_3)_2$ | |
| 12 | $C_2H_5$ | $C_2H_5$ | 0 | H | 2-$CH_3$-4-$CF_2CF_3$ | 108–111 |
| 13 | $C_2H_5$ | $C_2H_5$ | 0 | 4-Cl | 2-$CH_3$-4-$CF_2CF_3$ | 111–114 |
| 14 | n-$C_3H_7$ | H | 0 | H | 2-$CH_3$-4-$CF(CF_3)_2$ | |
| 15 | n-$C_3H_7$ | H | 0 | H | 4-$CF_3$ | |
| 16 | n-$C_3H_7$ | H | 0 | H | 2-$CH_3$-4-$OCF_3$ | |
| 17 | n-$C_3H_7$ | H | 0 | H | 2-$CH_3$-4-$CF_2CF_3$ | |
| 18 | $C(CH_3)_2CH_2$ | H | 0 | H | 2-$CH_3$-4-$CF(CF_3)_2$ | 64–65 |
|  | —$SCH_3$ | H | 0 | H | 2-$CH_3$-4-$CF(CF_2)_2$ | |
| 19 | n-$C_3H_7$ | H | 0 | H | 2-Cl-4-$CF(CF_3)_2$ | |
| 20 | i-$C_3H_7$ | H | 0 | H | 4-$CF_3$ | |
| 21 | i-$C_3H_7$ | H | 0 | H | 2-$NO_2$ | |
| 22 | i-$C_3H_7$ | H | 0 | H | 4-$NO_2$ | |
| 23 | i-$C_3H_7$ | H | 0 | H | 4-F | |
| 24 | i-$C_3H_7$ | H | 0 | H | 2-$CH_3$ | |
| 25 | i-$C_3H_7$ | H | 0 | H | 4-$CF_3$ | |
| 26 | i-$C_3H_7$ | H | 0 | H | 3-$CF_3$ | |
| 27 | i-$C_3H_7$ | H | 0 | H | 4-$CF_2CF_2CF_3$ | |

TABLE 1-continued ($Z^1 = Z^2 = O$, $R^3 = H$, Het = Q1, $B^1 = B^2 = B^3 = B^4 = C$)

| No | $R^1$ | $R^2$ | p | Xn | Ym | Physical property m.p. ° C. |
|---|---|---|---|---|---|---|
| 28 | i-$C_3H_7$ | H | 0 | H | 4-$(CF_2)_3CF_3$ | |
| 29 | i-$C_3H_7$ | H | 0 | H | 4-$OCF_3$ | |
| 30 | i-$C_3H_7$ | H | 0 | H | 4-$OCF_2CHFOC_3F_7$-n | |
| 31 | i-$C_3H_7$ | H | 0 | H | 3-$SCF_3$ | |
| 32 | $CH(CH_3)CH_2SCH_3$ | H | 0 | H | 2-$CH_3$-4-$CF(CF_3)_2$ | paste |
| 33 | i-$C_3H_7$ | H | 0 | H | 4-$SCH_2CF_3$ | |
| 34 | i-$C_3H_7$ | H | 0 | H | 4-$SCF_2CHF_2$ | |
| 35 | i-$C_3H_7$ | H | 0 | H | 4-$S(CF_2)_3CF_3$ | |
| 36 | i-$C_3H_7$ | H | 0 | H | 4-$SCF(CF_3)_2$ | |
| 37 | i-$C_3H_7$ | H | 0 | H | 4-$SCF_2BrF_2$ | |
| 38 | i-$C_3H_7$ | H | 0 | H | 4-$SOCF_2CBrF_2$ | |
| 39 | i-$C_3H_7$ | H | 0 | H | 4-$SO(CF_2)_3CF_3$ | |
| 40 | i-$C_3H_7$ | H | 0 | H | 4-$SO_2CH_2CF_3$ | |
| 41 | i-$C_3H_7$ | H | 0 | H | 2,3-$Cl_2$ | |
| 42 | i-$C_3H_7$ | H | 0 | H | 2,4-$Cl_2$ | |
| 43 | i-$C_3H_7$ | H | 0 | H | 3,4-$F_2$ | |
| 44 | i-$C_3H_7$ | H | 0 | H | 2,4-$(CH_3)_2$ | |
| 45 | i-$C_3H_7$ | H | 0 | H | 2-Cl-4-$CF_3$ | |
| 46 | i-$C_3H_7$ | H | 0 | H | 2-Cl-4-$CF(CF_3)_2$ | |
| 47 | i-$C_3H_7$ | H | 0 | H | 2-Cl-4-$OCF_3$ | |
| 48 | i-$C_3H_7$ | H | 0 | H | 2-Br-4-$OCF_3$ | |
| 49 | i-$C_3H_7$ | H | 0 | H | 2-$CH_3$-3-Cl | |
| 50 | i-$C_3H_7$ | H | 0 | H | 2-$CH_3$-4-Cl | |
| 51 | i-$C_3H_7$ | H | 0 | H | 2-$CH_3$-5-Cl | |
| 52 | i-$C_3H_7$ | H | 0 | H | 2-$CH_3$-4-Br | |
| 53 | i-$C_3H_7$ | H | 0 | H | 2-$CH_3$-5-F | |
| 54 | i-$C_3H_7$ | H | 0 | H | 2-$CH_3$-4-$CF_3$ | 167–169 |
| 55 | i-$C_3H_7$ | H | 0 | H | 2-$CH_3$-4-$CF_2CF_3$ | 188–189 |
| 56 | i-$C_3H_7$ | H | 0 | H | 2-$CH_3$-4-$CF_2CF_2CF_3$ | |
| 57 | i-$C_3H_7$ | H | 0 | H | 2-$CH_3$-4-$CF(CF_3)_2$ | 134–136 |
| 58 | i-$C_3H_7$ | H | 1 | H | 2-$CH_3$-4-$CF(CF_3)_2$ | |
| 59 | i-$C_3H_7$ | H | 0 | H | 2-$CH_3$-4-$OCF_3$ | |
| 60 | i-$C_3H_7$ | H | 0 | H | 2-$CH_3$-4-$OCF_2CHF_2$ | |
| 61 | i-$C_3H_7$ | H | 0 | H | 2-$CH_3$-3-$OCF_2CHClF$ | |
| 62 | i-$C_3H_7$ | H | 0 | H | 2-$CH_3$-4-$OCF_2CHClF$ | |
| 63 | i-$C_3H_7$ | H | 0 | H | 2-$CH_3$-4-$CF_2CBrF_2$ | |
| 64 | i-$C_3H_7$ | H | 0 | H | 2-$CH_3$-4-$CF_2CCl_2F$ | |
| 65 | i-$C_3H_7$ | H | 0 | H | 2-$CH_3$-4-$OCF_2CHFCF_3$ | |
| 66 | i-$C_3H_7$ | H | 0 | H | 2-$CH_3$-4-$OCF_2CBrFCF_3$ | |
| 67 | i-$C_3H_7$ | H | 0 | H | 2-$CH_3$-4-$OCF_2CHFOCF_3$ | |
| 68 | i-$C_3H_7$ | H | 0 | H | 2-$CH_3$-4-$SC_3H_7$-i | |
| 69 | i-$C_3H_7$ | H | 0 | H | 2-$CH_3$-4-$OCH_2OCH_3$ | |
| 70 | i-$C_3H_7$ | H | 0 | H | 2-$CH_3$-4-$OCH_2SCH_3$ | |
| 71 | i-$C_3H_7$ | H | 0 | H | 2-$CH_3$-4-$COOCH_3$ | |
| 72 | i-$C_3H_7$ | H | 0 | H | 2-$CH_3$-4-$OCH_2COOCH_3$ | |
| 73 | i-$C_3H_7$ | H | 0 | H | 2-$CH_3$-4-($F_5$—PhO) | |
| 74 | i-$C_3H_7$ | H | 0 | H | 2-$CH_3$-4-(3-$CF_3$—PhO) | |
| 75 | i-$C_3H_7$ | H | 0 | H | 2-$CH_3$-4-(2-Cl-4-$CF_3$—PhO) | |
| 76 | i-$C_3H_7$ | H | 0 | H | 2-$CH_3$-4-(4-Cl-Ph—$CH_2O$) | |
| 77 | i-$C_3H_7$ | H | 0 | H | 2-$CH_3$-4-(4-Cl—PhS) | |
| 78 | i-$C_3H_7$ | H | 0 | H | 2-$CH_3$-4-(5-$CF_3$-2-Pyr—O) | |
| 79 | i-$C_3H_7$ | H | 0 | H | 2-$CH_3$-4-(3-Cl-5-$CF_3$-2-Pyr—O) | |
| 80 | i-$C_3H_7$ | H | 0 | H | 4-(3-Cl-5-$CF_3$-2-Pyr—S) | |
| 81 | i-$C_3H_7$ | H | 0 | H | 2-$CH_3$-4-P=$O(OC_2H_5)_2$ | |
| 82 | i-$C_3H_7$ | H | 0 | H | 2-$CH_3$-4-OP=$S(OCH_3)_2$ | |
| 83 | i-$C_3H_7$ | H | 0 | H | 2-$CF_3$-4-$OCHF_2$ | |
| 84 | i-$C_3H_7$ | H | 0 | H | 3,5-$Cl_2$-4-$OCHF_2$ | |
| 85 | i-$C_3H_7$ | H | 0 | H | 3-N=C($CF_3$)—NH-4 | |
| 86 | i-$C_3H_7$ | H | 0 | H | 3-N=C($CF_3$)—N($CH_3$)-4 | |
| 87 | i-$C_3H_7$ | H | 0 | 4-Cl | 4-$C_4H_9$-n | |
| 88 | i-$C_3H_7$ | H | 0 | 4-Cl | 4-$C_4H_9$-t | |
| 89 | i-$C_3H_7$ | H | 0 | 4-Cl | 4-$CF(CF_3)_2$ | |
| 90 | i-$C_3H_7$ | H | 0 | 4-Cl | 4-$CF_2CF_2CF_3$ | |
| 91 | i-$C_3H_7$ | H | 0 | 4-Cl | 4-$(CF_2)_3CF_3$ | |
| 92 | i-$C_3H_7$ | H | 0 | 4-Cl | 4-$OCHF_2$ | |
| 93 | i-$C_3H_7$ | H | 0 | 4-Cl | 4-$OCF_2CHFOC_3F_7$-n | |
| 94 | i-$C_3H_7$ | H | 0 | 4-Cl | 4-$SCH_3$ | |
| 95 | i-$C_3H_7$ | H | 0 | 4-Cl | 4-$SOCH_3$ | |
| 96 | i-$C_3H_7$ | H | 0 | 4-Cl | 4-$SO_2CH_3$ | |
| 97 | i-$C_3H_7$ | H | 0 | 4-Cl | 4-$SCHF_2$ | |
| 98 | i-$C_3H_7$ | H | 0 | 4-Cl | 3-$SCF_3$ | |
| 99 | i-$C_3H_7$ | H | 0 | 4-Cl | 3-$SOCF_3$ | |
| 100 | i-$C_3H_7$ | H | 0 | 4-Cl | 4-$SCH_2CF_3$ | |

TABLE 1-continued ($Z^1 = Z^2 = O$, $R^3 = H$, Het = Q1, $B^1 = B^2 = B^3 = B^4 = C$)

| No | $R^1$ | $R^2$ | p | Xn | Ym | Physical property m.p. ° C. |
|---|---|---|---|---|---|---|
| 101 | i-$C_3H_7$ | H | 0 | 4-Cl | 4-$SCF_2CHF_2$ | |
| 102 | i-$C_3H_7$ | H | 0 | 4-Cl | 4-$SCF_2CBrF_2$ | |
| 103 | i-$C_3H_7$ | H | 0 | 4-Cl | 4-$SCF(CF_3)_2$ | |
| 104 | i-$C_3H_7$ | H | 0 | 4-Cl | 4-$S(CF_2)_3CF_3$ | |
| 105 | i-$C_3H_7$ | H | 0 | 4-Cl | 4-$SOCF(CF_3)_2$ | |
| 106 | i-$C_3H_7$ | H | 0 | 4-Cl | 4-$SO_2CH_2CF_3$ | |
| 107 | i-$C_3H_7$ | H | 0 | 4-Cl | 4-$SO_2CF_2CHF_2$ | |
| 108 | i-$C_3H_7$ | H | 0 | 4-Cl | 4-$COCH_3$ | |
| 109 | i-$C_3H_7$ | H | 0 | 4-Cl | 4-Ph | |
| 110 | i-$C_3H_7$ | H | 0 | 4-Cl | 2,3-$Cl_2$ | |
| 111 | i-$C_3H_7$ | H | 0 | 4-Cl | 2,4-$Cl_2$ | |
| 112 | i-$C_3H_7$ | H | 0 | 4-Cl | 2,4-$F_2$ | |
| 113 | i-$C_3H_7$ | H | 0 | 4-Cl | 2-Cl-4-F | |
| 114 | i-$C_3H_7$ | H | 0 | 4-Cl | 2-F-4-Cl | |
| 115 | i-$C_3H_7$ | H | 0 | 4-Cl | 2,3,4-$F_3$ | |
| 116 | i-$C_3H_7$ | H | 0 | 4-Cl | 2,3-$(CH_3)_2$ | |
| 117 | i-$C_3H_7$ | H | 0 | 4-Cl | 2-$CH_3$-3-Cl | |
| 118 | i-$C_3H_7$ | H | 0 | 4-Cl | 2-$CH_3$-4-Cl | |
| 119 | i-$C_3H_7$ | H | 0 | 4-Cl | 2-$CH_3$-5-Cl | |
| 120 | i-$C_3H_7$ | H | 0 | 4-Cl | 2-$CH_3$-4-Br | |
| 121 | i-$C_3H_7$ | H | 0 | 4-Cl | 2-$CH_3$-4-I | |
| 122 | i-$C_3H_7$ | H | 0 | 4-Cl | 2-$CH_3$-4-$OCH_3$ | |
| 123 | i-$C_3H_7$ | H | 0 | 4-Cl | 2,3-$(CH_3)_2$-4-$OCH_3$ | |
| 124 | i-$C_3H_7$ | H | 0 | 4-Cl | 2-Cl-4-$CF_3$ | |
| 125 | i-$C_3H_7$ | H | 1 | 4-Cl | 2-Cl-4-$CF(CF_3)_2$ | |
| 126 | i-$C_3H_7$ | H | 0 | 4-Cl | 2-$CH_3$-4-$CF_3$ | |
| 127 | i-$C_3H_7$ | H | 0 | 4-Cl | 2-$CH_3$-4-$CF_2CF_3$ | 162–167 |
| 128 | i-$C_3H_7$ | H | 0 | 4-Cl | 2-$CH_3$-4-$OCF_2CCl_3$ | |
| 129 | i-$C_3H_7$ | H | 0 | 4-Cl | 2-$CH_3$-4-$CF_2CF_2CF_3$ | |
| 130 | i-$C_3H_7$ | H | 0 | 4-Cl | 2-$CH_3$-4-$CF(CF_3)_2$ | |
| 131 | i-$C_3H_7$ | H | 0 | 4-Cl | 2-$CH_3$-4-$(CF_2)_3CF_3$ | |
| 132 | s-$C_4H_9$ | H | 0 | 4-Cl | 2-$CH_3$-4-$(CF_2)_3CF_3$ | |
| 133 | i-$C_4H_9$ | H | 0 | 4-Cl | 2-$CH_3$-4-$CF(CF_3)_2$ | |
| 134 | t-$C_4H_9$ | H | 0 | 4-Cl | 2-Cl-4-$OCF_3$ | |
| 135 | t-$C_4H_9$ | H | 0 | 4-Cl | 2-Br-4-$OCF_3$ | |
| 136 | t-$C_4H_9$ | H | 0 | 4-Cl | 2-$CH_3$-4-$CF_2CF_3$ | 175–180 |
| 137 | i-$C_3H_7$ | H | 0 | 4-Br | 2-Cl-4-$CF_3$ | |
| 138 | i-$C_3H_7$ | H | 0 | 4-Br | 2-Cl-4-$CF(CF_3)_2$ | |
| 139 | i-$C_3H_7$ | H | 0 | 4-Br | 2-$CH_3$-4-$CF_3$ | |
| 140 | i-$C_3H_7$ | H | 0 | 4-Br | 2-$CH_3$-4-$CF_2CF_3$ | |
| 141 | i-$C_3H_7$ | H | 0 | 4-Br | 2-$CH_3$-4-$OCF_2CCl_2$ | |
| 142 | i-$C_3H_7$ | H | 0 | 4-Br | 2-$CH_3$-4-$CF_2CF_2CF_3$ | |
| 143 | i-$C_3H_7$ | H | 0 | 4-Br | 2-$CH_3$-4-$CF(CF_3)_2$ | |
| 144 | i-$C_3H_7$ | H | 0 | 4-Br | 2-$CH_3$-4-$(CF_2)_3CF_3$ | |
| 145 | i-$C_3H_7$ | H | 0 | 4-Br | 2-$CH_3$-4-$(CF_2)_5CF_3$ | |
| 146 | i-$C_3H_7$ | H | 0 | 4-Br | 3-Cl-4-$OCHF_2$ | |
| 147 | i-$C_3H_7$ | H | 0 | 4-Br | 2-Cl-4-$OCF_3$ | |
| 148 | i-$C_3H_7$ | H | 0 | 4-Br | 2-Br-4-$OCF_3$ | |
| 149 | i-$C_3H_7$ | H | 0 | 4-Br | 2-Br-4-$CF(CF_3)_2$ | |
| 150 | i-$C_3H_7$ | H | 0 | 4-I | 2-$CH_3$-3-Cl | |
| 151 | i-$C_3H_7$ | H | 0 | 4-I | 2-$CH_3$-4-Cl | |
| 152 | i-$C_3H_7$ | H | 0 | 4-I | 2-$CH_3$-5-Cl | |
| 153 | i-$C_3H_7$ | H | 0 | 4-I | 2-$CH_3$-4-Br | |
| 154 | i-$C_3H_7$ | H | 0 | 4-I | 2-$CH_3$-4-I | |
| 155 | i-$C_3H_7$ | H | 0 | 4-I | 2-$CH_3$-4-$OCH_3$ | |
| 156 | i-$C_3H_7$ | H | 0 | 4-I | 2,3-$(CH_3)_2$-4-$OCH_3$ | |
| 157 | i-$C_3H_7$ | H | 0 | 4-I | 2-Cl-4-$CF_3$ | |
| 158 | i-$C_3H_7$ | H | 0 | 4-I | 2-Cl-4-$CF(CF_3)_2$ | |
| 159 | i-$C_3H_7$ | H | 0 | 4-I | 2-$CH_3$-4-$CF_3$ | |
| 160 | i-$C_3H_7$ | H | 1 | 4-I | 2-$CH_3$-4-$CF_2CF_3$ | |
| 161 | i-$C_3H_7$ | H | 0 | 4-I | 2-$CH_3$-4-$OCF_2CCl_3$ | |
| 162 | i-$C_3H_7$ | H | 0 | 4-I | 2-$CH_3$-4-$CF_2CF_2CF_3$ | |
| 163 | i-$C_3H_7$ | H | 0 | 4-I | 2-$CH_3$-4-$CF(CF_3)_2$ | |
| 164 | i-$C_3H_7$ | H | 0 | 4-I | 2-$CH_3$-4-$(CF_2)_3CF_3$ | |
| 165 | i-$C_3H_7$ | H | 0 | 4-I | 2-$CH_3$-4-$(CF_2)_5CF_3$ | |
| 166 | i-$C_3H_7$ | H | 0 | 4-I | 3-Cl-4-$OCHF_2$ | |
| 167 | i-$C_3H_7$ | H | 0 | 4-I | 2-Cl-4-$OCF_3$ | |
| 168 | i-$C_3H_7$ | H | 0 | 4-I | 2-Br-4-$OCF_3$ | |
| 169 | i-$C_3H_7$ | H | 0 | 4-I | 2-Br-4-$CF(CF_3)_2$ | |
| 170 | i-$C_3H_7$ | H | 0 | 6-Cl | 2-$CH_3$-3-Cl | |
| 171 | i-$C_3H_7$ | H | 0 | 6-Cl | 2-$CH_3$-4-Cl | |
| 172 | i-$C_3H_7$ | H | 0 | 6-Cl | 2-$CH_3$-5-Cl | |
| 173 | i-$C_3H_7$ | H | 0 | 6-Cl | 2-$CH_3$-4-Br | |

TABLE 1-continued ($Z^1 = Z^2 = O$, $R^3 = H$, Het = Q1, $B^1 = B^2 = B^3 = B^4 = C$)

| No | $R^1$ | $R^2$ | p | Xn | Ym | Physical property m.p. °C |
|---|---|---|---|---|---|---|
| 174 | i-$C_3H_7$ | H | 0 | 6-Cl | 2-$CH_3$-4-I | |
| 175 | i-$C_3H_7$ | H | 0 | 6-Cl | 2-$CH_3$-4-$OCH_3$ | |
| 176 | i-$C_3H_7$ | H | 0 | 6-Cl | 2,3-$(CH_3)_2$-4-$OCH_3$ | |
| 177 | i-$C_3H_7$ | H | 0 | 6-Cl | 2-Cl-4-$CF_3$ | |
| 178 | i-$C_3H_7$ | H | 0 | 6-Cl | 2-Cl-4-$CF(CF_3)_2$ | |
| 179 | i-$C_3H_7$ | H | 0 | 6-Cl | 2-$CH_3$-4-$CF_3$ | |
| 180 | i-$C_3H_7$ | H | 0 | 6-Cl | 2-$CH_3$-4-$CF_2CF_3$ | |
| 181 | i-$C_3H_7$ | H | 0 | 6-Cl | 2-$CH_3$-4-$OCF_2CCl_3$ | |
| 182 | i-$C_3H_7$ | H | 0 | 6-Cl | 2-$CH_3$-4-$CF_2CF_2CF_3$ | |
| 183 | i-$C_3H_7$ | H | 0 | 6-Cl | 2-$CH_3$-4-$CF(CF_3)_2$ | |
| 184 | i-$C_3H_7$ | H | 0 | 6-Cl | 2-$CH_3$-4-$(CF_2)_3CF_3$ | |
| 185 | i-$C_3H_7$ | H | 0 | 6-Cl | 2-$CH_3$-4-$(CF_2)_5CF_3$ | |
| 186 | i-$C_3H_7$ | H | 0 | 6-Cl | 3-Cl-4-$OCHF_2$ | |
| 187 | i-$C_3H_7$ | H | 0 | 6-Cl | 2-Cl-4-$OCF_3$ | |
| 188 | i-$C_3H_7$ | H | 0 | 6-Cl | 2-Br-4-$OCF_3$ | |
| 189 | i-$C_3H_7$ | H | 0 | 6-Cl | 2-Br-4-$CF(CF_3)_2$ | |
| 190 | i-$C_3H_7$ | H | 0 | 6-I | 2-$CH_3$-3-Cl | |
| 191 | i-$C_3H_7$ | H | 0 | 6-I | 2-$CH_3$-4-Cl | |
| 192 | i-$C_3H_7$ | H | 0 | 6-I | 2-$CH_3$-5-Cl | |
| 193 | i-$C_3H_7$ | H | 0 | 6-I | 2-$CH_3$-4-Br | |
| 194 | i-$C_3H_7$ | H | 0 | 6-I | 2-$CH_3$-4-I | |
| 195 | i-$C_3H_7$ | H | 0 | 6-I | 2-$CH_3$-4-$OCH_3$ | |
| 196 | i-$C_3H_7$ | H | 0 | 6-I | 2,3-$(CH_3)_2$-4-$OCH_3$ | |
| 197 | i-$C_3H_7$ | H | 0 | 6-I | 2-Cl-4-$CF_3$ | |
| 198 | i-$C_3H_7$ | H | 0 | 6-I | 2-Cl-4-$CF(CF_3)_2$ | |
| 199 | i-$C_3H_7$ | H | 0 | 6-I | 2-$CH_3$-4-$CF_3$ | |
| 200 | i-$C_3H_7$ | H | 0 | 6-I | 2-$CH_3$-4-$CF_2CF_3$ | |
| 201 | i-$C_3H_7$ | H | 0 | 6-I | 2-$CH_3$-4-$OCF_2CCl_3$ | |
| 202 | i-$C_3H_7$ | H | 0 | 6-I | 2-$CH_3$-4-$CF_2CF_2CF_3$ | |
| 203 | i-$C_3H_7$ | H | 0 | 6-I | 2-$CH_3$-4-$CF(CF_3)_2$ | |
| 204 | i-$C_3H_7$ | H | 0 | 6-I | 2-$CH_3$-4-$(CF_2)_3CF_3$ | |
| 205 | i-$C_3H_7$ | H | 0 | 6-I | 2-$CH_3$-4-$(CF_2)_5CF_3$ | |
| 206 | i-$C_3H_7$ | H | 0 | 6-I | 3-Cl-4-$OCHF_2$ | |
| 207 | i-$C_3H_7$ | H | 0 | 6-I | 2-Cl-4-$OCF_3$ | |
| 208 | i-$C_3H_7$ | H | 0 | 6-I | 2-Br-4-$OCF_3$ | |
| 209 | i-$C_3H_7$ | H | 0 | 6-I | 2-Br-4-$CF(CF_3)_2$ | |
| 210 | i-$C_3H_7$ | H | 0 | 6-I | 2-$CH_3$-4-$CF_3$ | |
| 211 | i-$C_3H_7$ | H | 0 | 4-I | 2-$CH_3$-4-$CF_2CF_3$ | |
| 212 | i-$C_3H_7$ | H | 0 | 4-I | 2-$CH_3$-4-$OCF_2CCl_3$ | |
| 213 | i-$C_3H_7$ | H | 0 | 4-I | 2-$CH_3$-4-$CF_2CF_2CF_3$ | |
| 214 | i-$C_3H_7$ | H | 0 | 4-I | 2-$CH_3$-4-$CF(CF_3)_2$ | |
| 215 | i-$C_3H_7$ | H | 0 | 4-I | 2-$CH_3$-4-$(CF_2)_3CF_3$ | |
| 216 | i-$C_3H_7$ | H | 0 | 4-I | 2-$CH_3$-4-$(CF_2)_5CF_3$ | |
| 217 | i-$C_3H_7$ | H | 0 | 4-I | 3-Cl-4-$OCHF_2$ | |
| 218 | i-$C_3H_7$ | H | 0 | 4-I | 2-Cl-4-$OCF_3$ | |
| 219 | i-$C_3H_7$ | H | 0 | 4-I | 2-Br-4-$OCF_3$ | |

TABLE 2

($Z^1 = Z^2 = O$, $R^3 = H$, Het = Q2, $B^1 = B^2 = B^3 = B^4 = C$)

| No | $R^1$ | $R^2$ | p | Xn | Ym | Physical property m.p. °C |
|---|---|---|---|---|---|---|
| 220 | i-$C_3H_7$ | H | 0 | H | 2-$CH_3$-4-$CF_3$ | |
| 221 | i-$C_3H_7$ | H | 0 | H | 2-$CH_3$-4-$OCHF_2$ | |
| 222 | i-$C_3H_7$ | H | 0 | H | 2-$CH_3$-4-$OCF_2$ | |
| 223 | i-$C_3H_7$ | H | 0 | H | 2-$CH_3$-4-$OCBrF_2$ | |
| 224 | i-$C_3H_7$ | H | 0 | H | 2-$CH_3$-4-$OCF_2CHF_2$ | |
| 225 | i-$C_3H_7$ | H | 0 | H | 2-$CH_3$-3-$OCF_2CHClF$ | |
| 226 | i-$C_3H_7$ | H | 0 | H | 2-$CH_3$-4-$OCF_2CCl_2F$ | |
| 227 | i-$C_3H_7$ | H | 0 | H | 2-$CH_3$-4-$OCF_2CBrF_2$ | |
| 228 | i-$C_3H_7$ | H | 0 | H | 2-$CH_3$-4-$OCH_2CF_2CHF_2$ | |
| 229 | i-$C_3H_7$ | H | 0 | H | 2-$CH_3$-4-$CF_2CF_3$ | |
| 230 | i-$C_3H_7$ | H | 0 | H | 2-$CH_3$-4-$CF(CF_3)_2$ | 234–236 |
| 231 | i-$C_3H_7$ | H | 0 | H | 2-$CH_3$-4-$SCF_2CBrF_2$ | |
| 232 | i-$C_3H_7$ | H | 0 | H | 2-$CH_3$-4-$SCH_2CF_2CHF_2$ | |
| 233 | i-$C_3H_7$ | H | 0 | H | 2-$CH_3$-4-$SO_2CH_2CF_2CHF_2$ | |
| 234 | i-$C_3H_7$ | H | 0 | H | 2-Cl-4-$CF_3$ | |

TABLE 2-continued ($Z^1$ = $Z^2$ = O, $R^3$ = H, Het = Q2, $B^1$ = $B^2$ = $B^3$ = $B^4$ = C)

| No | $R^1$ | $R^2$ | p | Xn | Ym | Physical property m.p. ° C. |
|---|---|---|---|---|---|---|
| 235 | i-$C_3H_7$ | H | 0 | H | 2-Cl-4-CF($CF_2$)$_2$ | |
| 236 | i-$C_3H_7$ | H | 0 | H | 3-Cl-4-OCHF$_2$ | |
| 237 | i-$C_3H_7$ | H | 0 | H | 3-F-4-OCHF$_2$ | |
| 238 | i-$C_3H_7$ | H | 0 | H | 2-Cl-4-OCF$_3$ | |
| 239 | i-$C_3H_7$ | H | 1 | H | 2-CH$_3$-4-CF$_2$CF$_3$ | |
| 240 | i-$C_3H_7$ | H | 1 | H | 2-CH$_3$-4-CF(CF$_3$)$_2$ | |
| 241 | i-$C_3H_7$ | H | 0 | 2-Cl | 2-CH$_3$-4-CF$_2$CF$_3$ | |
| 242 | i-$C_3H_7$ | H | 0 | 2-Cl | 2-CH$_3$-4-CF(CF$_3$)$_2$ | 315 (dec.) |
| 243 | i-$C_3H_7$ | H | 0 | 2-Cl | 2-CH$_3$-4-OCF$_2$CBrFCF$_3$ | |
| 244 | i-$C_3H_7$ | H | 0 | 2-Cl | 2-CH$_3$-4-OCF$_2$CHFOCF$_3$ | |
| 245 | i-$C_3H_7$ | H | 0 | 2-Cl | 2-CH$_3$-4-OCHF$_2$-5-Cl | |
| 246 | i-$C_3H_7$ | H | 0 | 2-Cl | 2-CH$_3$-4-OCF$_2$CHF$_2$-5-Cl | |
| 247 | i-$C_3H_7$ | H | 0 | 2-Cl | 2-CH$_3$-4-SCHF$_2$ | |
| 248 | i-$C_3H_7$ | H | 0 | 2-Cl | 2-CH$_3$-4-(F$_5$—PhO) | |
| 249 | i-$C_3H_7$ | H | 0 | 2-Cl | 2-CH$_3$-4-(5-CF$_3$-2-Pyr—O) | |
| 250 | i-$C_3H_7$ | H | 0 | 2-Cl | 2-CH$_3$-4-(3-Cl-5-CF$_2$-2-Pyr—O) | |
| 251 | i-$C_3H_7$ | H | 0 | 2-Cl | 2-CH$_3$-4-P=O(OC$_2$H$_5$)$_2$ | |
| 252 | i-$C_3H_7$ | H | 0 | 2-Cl | 2-CH$_3$-4-OP=S(OCH$_3$)$_2$ | |
| 253 | i-$C_3H_7$ | H | 0 | 2-Cl | 2-CF$_3$-4-OCHF$_2$ | |
| 254 | i-$C_3H_7$ | H | 0 | 2-Cl | 3-CF$_3$-4-OCHF$_2$ | |
| 255 | i-$C_3H_7$ | H | 0 | 2-Cl | 3-N=C(CF$_3$)-O-4 | |
| 256 | i-$C_3H_7$ | H | 0 | 2-Cl | 3-N=C(CF$_3$)-NH-4 | |
| 257 | i-$C_3H_7$ | H | 0 | 2-Cl | 3-N=C(CF$_3$)-N(CH$_3$)-4 | |
| 258 | i-$C_3H_7$ | H | 0 | 2-Cl | 2-CH$_3$-4-OCF3 | 229–231 |
| 259 | i-$C_3H_7$ | H | 0 | 2-Br | 2-CH$_3$-4-CF$_3$ | |
| 260 | i-$C_3H_7$ | H | 0 | 2-Br | 2-CH$_3$-4-OCHF$_2$ | |
| 261 | i-$C_3H_7$ | H | 0 | 2-Br | 2-CH$_3$-4-OCF$_3$ | |
| 262 | i-$C_3H_7$ | H | 0 | 2-Br | 2-CH$_3$-4-OCBrF$_2$ | |
| 263 | i-$C_3H_7$ | H | 0 | 2-Br | 2-CH$_3$-4-OCF$_2$CHF$_2$ | |
| 264 | i-$C_3H_7$ | H | 0 | 2-Br | 2-CH$_3$-3-OCF$_2$CHClF | |
| 265 | i-$C_3H_7$ | H | 0 | 2-Br | 2-CH$_3$-4-OCF$_2$CCl$_2$F | |
| 266 | i-$C_3H_7$ | H | 0 | 2-Br | 2-CH$_3$-4-OCF$_2$CBrF$_2$ | |
| 267 | i-$C_3H_7$ | H | 0 | 2-Br | 2-CH$_3$-4-OCH$_2$CF$_2$CHF$_2$ | |
| 268 | i-$C_3H_7$ | H | 0 | 2-Br | 2-CH$_3$-4-CF$_2$CF$_3$ | |
| 269 | i-$C_3H_7$ | H | 0 | 2-Br | 2-CH$_3$-4-CF(CF$_3$)$_2$ | |
| 270 | i-$C_3H_7$ | H | 0 | 2-Br | 2-CH$_3$-4-SCF$_2$CBrF$_2$ | |
| 271 | i-$C_3H_7$ | H | 0 | 2-Br | 2-CH$_3$-4-SCH$_2$CF$_2$CHF$_2$ | |
| 272 | i-$C_3H_7$ | H | 0 | 2-Br | 2-CH$_3$-4-SO$_2$CH$_2$CF$_2$CHF$_2$ | |
| 273 | i-$C_3H_7$ | H | 0 | 2-Br | 2-Cl-4-CF$_3$ | |
| 274 | i-$C_3H_7$ | H | 0 | 2-Br | 2-Cl-4-CF(CF$_2$)$_2$ | |
| 275 | i-$C_3H_7$ | H | 0 | 2-Br | 3-Cl-4-OCHF$_2$ | |
| 276 | i-$C_3H_7$ | H | 0 | 2-Br | 3-F-4-OCHF$_2$ | |
| 277 | i-$C_3H_7$ | H | 0 | 2-Br | 2-Cl-4-OCF$_3$ | |
| 278 | i-$C_3H_7$ | H | 0 | 2-Br | 2-Br-4-OCF$_3$ | |
| 279 | i-$C_3H_7$ | H | 0 | 2-Br | 3,5-Cl$_2$-4-OCHF$_2$ | |
| 280 | i-$C_3H_7$ | H | 0 | 2-I | 2-CH$_3$-4-CF(CF$_3$)$_2$ | |
| 281 | i-$C_3H_7$ | H | 0 | 2-I | 2-CH$_3$-4-(CF$_2$)$_3$CF$_3$ | |
| 282 | i-$C_3H_7$ | H | 0 | 2-I | 2-CH$_3$-4-OCH$_3$ | |
| 283 | i-$C_3H_7$ | H | 0 | 2-I | 2-CH$_3$-4-OCH$_2$CF$_2$CHF$_2$ | |
| 284 | i-$C_3H_7$ | H | 0 | 2-I | 2,4-(CH$_3$)$_2$-3-OCHF$_2$ | |
| 285 | i-$C_3H_7$ | H | 0 | 2-I | 2,3-(CH$_3$)$_2$-4-OCH$_3$ | |
| 286 | i-$C_3H_7$ | H | 0 | 2-I | 2-Cl-4-OCF$_3$ | |
| 287 | i-$C_3H_7$ | H | 0 | 2-I | 2-Br-4-OCF$_3$ | |
| 288 | i-$C_3H_7$ | H | 0 | 2-I | 2-CH$_3$-4-OCHF$_2$ | |
| 289 | i-$C_3H_7$ | H | 0 | 2-I | 2-CH$_3$-4-OCF$_3$ | |
| 290 | i-$C_3H_7$ | H | 0 | 2-I | 2-CH$_3$-4-OCBrF$_2$ | |
| 291 | i-$C_3H_7$ | H | 0 | 2-I | 2-CH$_3$-4-OCF$_2$CHFCF$_3$ | |
| 292 | i-$C_3H_7$ | H | 0 | 2-I | 2-CH$_3$-4-OCF$_2$CHClF | |
| 293 | i-$C_3H_7$ | H | 0 | 2-I | 2-CH$_3$-4-OCF$_2$CHF$_2$ | |
| 294 | i-$C_3H_7$ | H | 0 | 2-I | 2-CH$_3$-3-Cl-4-OCHF$_2$ | |
| 295 | i-$C_3H_7$ | H | 0 | 2-I | 2,3-(CH$_3$)$_2$-4-OCHF$_2$ | |
| 296 | i-$C_3H_7$ | H | 0 | 2-I | 2-CH$_3$-4-SCH$_3$ | |
| 297 | i-$C_3H_7$ | H | 0 | 2-I | 2-CH$_3$-4-(3-CF$_3$—PhO) | |
| 298 | i-$C_3H_7$ | H | 0 | 2-I | 2-CH$_3$-4-(3-Cl-5-CF$_3$-2-Pyr—O) | |
| 299 | i-$C_3H_7$ | H | 0 | 5-Cl | 2-CH$_3$-4-(5-CF$_3$-2-Pyr—O) | |
| 300 | i-$C_3H_7$ | H | 0 | 5-Cl | -3-OCH$_2$O-4- | |
| 301 | i-$C_3H_7$ | H | 0 | 5-Cl | 4-CF$_3$ | |
| 302 | i-$C_3H_7$ | H | 0 | 5-Cl | 4-OCF$_3$ | |
| 303 | i-$C_3H_7$ | H | 0 | 5-Cl | 2,3-(CH$_3$)$_2$ | |
| 304 | i-$C_3H_7$ | H | 0 | 5-Cl | 2,4,6-(CH$_3$)$_3$ | |
| 305 | i-$C_3H_7$ | H | 0 | 5-Cl | 2-CH$_3$-3-Cl | |

TABLE 2-continued ($Z^1 = Z^2 = O$, $R^3 = H$, Het = Q2, $B^1 = B^2 = B^3 = B^4 = C$)

| No | $R^1$ | $R^2$ | p | Xn | Ym | Physical property m.p. ° C. |
|---|---|---|---|---|---|---|
| 306 | i-$C_3H_7$ | H | 0 | 5-Cl | 2-$CH_3$-4-Cl | |
| 307 | i-$C_3H_7$ | H | 0 | 5-Cl | 2-$CH_3$-5-Cl | |
| 308 | i-$C_3H_7$ | H | 0 | 5-Cl | 2,3-$(CH_3)_2$-4-Cl | |
| 309 | i-$C_3H_7$ | H | 0 | 5-Cl | 2,4-$(CH_3)_2$-3-Cl | |
| 310 | i-$C_3H_7$ | H | 0 | 5-Cl | 2-$C_2H_5$-4-Cl | |
| 311 | i-$C_3H_7$ | H | 0 | 5-Cl | 2-$CH_3$-4-Br | |
| 312 | i-$C_3H_7$ | H | 0 | 5-Cl | 2,3-$(CH_3)_2$-4-Br | |
| 313 | i-$C_3H_7$ | H | 0 | 5-Cl | 2-$CH_3$-4-I | |
| 314 | i-$C_3H_7$ | H | 0 | 5-Cl | 2-$CH_3$-4-F | |
| 315 | i-$C_3H_7$ | H | 0 | 5-Cl | 2-Cl-4-$CF_3$ | |
| 316 | i-$C_3H_7$ | H | 0 | 5-Cl | 2-$CH_3$-4-$CF_3$ | |
| 317 | i-$C_3H_7$ | H | 0 | 5-Cl | 2-$CH_3$-4-$CF(CF_3)_2$ | |
| 318 | i-$C_3H_7$ | H | 0 | 5-Cl | 2-$CH_3$-4-$(CF_2)_3CF_3$ | |
| 319 | i-$C_3H_7$ | H | 0 | 5-Cl | 2-$CH_3$-4-$OCH_2CF_2CHF_2$ | |
| 320 | i-$C_3H_7$ | H | 0 | 5-Cl | 2,4-$(CH_3)_2$-3-$OCHF_2$ | |
| 321 | i-$C_3H_7$ | H | 0 | 5-Cl | 2,3-$(CH_3)_2$-4-$OCH_3$ | |
| 322 | i-$C_3H_7$ | H | 0 | 5-Cl | 2-$CH_3$-4-$OCH_3$ | |
| 323 | i-$C_3H_7$ | H | 0 | 5-Cl | 2-Cl-4-$OCF_3$ | |
| 324 | i-$C_3H_7$ | H | 0 | 5-Cl | 2-Br-4-$OCF_3$ | |
| 325 | i-$C_3H_7$ | H | 0 | 5-Cl | 2-$CH_3$-4-$OCHF_2$ | |
| 326 | i-$C_3H_7$ | H | 0 | 5-Cl | 2-$CH_3$-4-$OCF_3$ | |
| 327 | i-$C_3H_7$ | H | 0 | 5-Cl | 2-$CH_3$-4-$OCBrF_2$ | |
| 328 | i-$C_3H_7$ | H | 0 | 5-Cl | 2-$CH_3$-4-$OCF_2CHFCF_3$ | |
| 329 | i-$C_3H_7$ | H | 0 | 5-Cl | 2-$CH_3$-4-$OCF_2CHClF$ | |
| 330 | i-$C_3H_7$ | H | 0 | 5-Cl | 2-$CH_3$-4-$OCF_2CHF_2$ | |
| 331 | i-$C_3H_7$ | H | 0 | 5-Cl | 2,3-$(CH_3)_2$-4-$OCHF_2$ | |
| 332 | i-$C_3H_7$ | H | 0 | 5-Cl | 2-$CH_3$-3-Cl-4-$OCHF_2$ | |
| 333 | i-$C_3H_7$ | H | 0 | 5-Cl | 2-$CH_3$-4-$SCH_3$ | |
| 334 | i-$C_3H_7$ | H | 0 | 5-Cl | 2-$CH_3$-4-(3-$CF_3$—PhO) | |
| 335 | i-$C_3H_7$ | H | 0 | 5-Cl | 2-$CH_3$-4-(5-$CF_3$-2-Pyr—O) | |
| 336 | i-$C_3H_7$ | H | 0 | 5-Cl | 2-$CH_3$-4-(3-Cl-5-$CF_3$-2-Pyr—O) | |
| 337 | i-$C_3H_7$ | H | 0 | 5-Cl | -3-$OCH_2O$-4- | |
| 338 | i-$C_3H_7$ | H | 0 | 5-Cl | 2-Cl-4-$OCHF_2$ | |
| 339 | i-$C_3H_7$ | H | 0 | 5-I | 4-Cl | |
| 340 | i-$C_3H_7$ | H | 0 | 5-I | 4-Br | |
| 341 | i-$C_3H_7$ | H | 0 | 5-I | 4-I | |
| 342 | i-$C_3H_7$ | H | 0 | 5-I | 3-$CF_3$ | |
| 343 | i-$C_3H_7$ | H | 0 | 5-I | 4-$CF_3$ | |
| 344 | i-$C_3H_7$ | H | 0 | 5-I | 4-$CF_2CF_2CF_3$ | |
| 345 | i-$C_3H_7$ | H | 0 | 5-I | 4-$CF(CF_3)_2$ | |
| 346 | i-$C_3H_7$ | H | 0 | 5-I | 4-$OCF_3$ | |
| 347 | i-$C_3H_7$ | H | 0 | 5-I | 4-$OCF_2CHFOCF_3$ | |
| 348 | i-$C_3H_7$ | H | 0 | 5-I | 4-$SCHF_2$ | |
| 349 | i-$C_3H_7$ | H | 0 | 5-I | 4-$SCH_2CF_3$ | |
| 350 | i-$C_3H_7$ | H | 0 | 5-I | 4-$SCF_2CHF_2$ | |
| 351 | i-$C_3H_7$ | H | 0 | 5-I | 4-$SCF_2CBrF_2$ | |
| 352 | i-$C_3H_7$ | H | 0 | 5-I | 4-$SCF(CF_3)_2$ | |
| 353 | i-$C_3H_7$ | H | 0 | 5-I | 4-$S(CF_2)_3CF_3$ | |
| 354 | i-$C_3H_7$ | H | 0 | 5-I | 3,4-$F_2$ | |
| 355 | i-$C_3H_7$ | H | 0 | 5-I | 2-$CH_3$-3-Cl | |
| 356 | i-$C_3H_7$ | H | 0 | 5-I | 2-$CH_3$-4-Cl | |
| 357 | i-$C_3H_7$ | H | 0 | 5-I | 2-$CH_3$-5-Cl | |
| 358 | i-$C_3H_7$ | H | 0 | 5-I | 2,4-$(CH_3)_2$-3-Cl | |
| 359 | i-$C_3H_7$ | H | 0 | 5-I | 2,3-$(CH_3)_2$-4-Cl | |
| 360 | i-$C_3H_7$ | H | 0 | 5-I | 2-Cl-4-$CF_3$ | |
| 361 | i-$C_3H_7$ | H | 0 | 5-I | 2-Cl-4-$CF_2CF_3$ | |
| 362 | i-$C_3H_7$ | H | 0 | 5-I | 2-Cl-4-$CF_2CF_2CF_3$ | |
| 363 | i-$C_3H_7$ | H | 0 | 5-I | 2-Cl-4-$CF(CF_3)_2$ | |
| 364 | i-$C_3H_7$ | H | 0 | 5-I | 2-Cl-4-$(CF_2)_3CF_3$ | |
| 365 | i-$C_3H_7$ | H | 0 | 5-I | 2-$C_2H_5$-4-$CF(CF_3)_2$ | |
| 366 | i-$C_3H_7$ | H | 0 | 5-I | 2-$CH_3$-4-Br | |
| 367 | i-$C_3H_7$ | H | 0 | 5-I | 2-$CH_3$-4-I | |
| 368 | i-$C_3H_7$ | H | 0 | 5-I | 2-$CH_3$-4-F | |
| 369 | i-$C_3H_7$ | H | 0 | 5-I | 2-Cl-4-$CF_3$ | |
| 370 | i-$C_3H_7$ | H | 0 | 5-I | 2-$CH_3$-3-$CF_3$ | |
| 371 | i-$C_3H_7$ | H | 0 | 5-I | 2-$CH_3$-4-$CF_3$ | |
| 372 | i-$C_3H_7$ | H | 0 | 5-I | 2-$CH_3$-4-$CF_2CF_3$ | |
| 373 | i-$C_3H_7$ | H | 0 | 5-I | 2-$CH_3$-4-$CF_2CF_2CF_3$ | |
| 374 | i-$C_3H_7$ | H | 0 | 5-I | 2-$CH_3$-4-$CF(CF_3)_2$ | |

TABLE 2-continued ($Z^1 = Z^2 = O$, $R^3 = H$, Het = Q2, $B^1 = B^2 = B^3 = B^4 = C$)

| No | $R^1$ | $R^2$ | p | Xn | Ym | Physical property m.p. °C. |
|---|---|---|---|---|---|---|
| 375 | i-$C_3H_7$ | H | 0 | 5-I | 2-$CH_3$-4-$(CF_2)_3CF_3$ | |
| 376 | i-$C_3H_7$ | H | 0 | 5-I | 2-$CH_3$-4-$OCH_3$ | |
| 377 | i-$C_3H_7$ | H | 0 | 5-I | 2-$CH_3$-4-O—$C_3H_7$-i | |
| 378 | i-$C_3H_7$ | H | 0 | 5-I | 2,3-$(CH_3)_2$-4-$OCH_3$ | |
| 379 | i-$C_3H_7$ | H | 0 | 5-I | 2-$CH_3$-4-$OCH_2CF_3$ | |
| 380 | i-$C_3H_7$ | H | 0 | 5-I | 2-$CH_3$-4-$OCF_2CBrF_2$ | |
| 381 | i-$C_3H_7$ | H | 0 | 5-Br | 2-$CH_3$-4-$OCF_2CCl_2F$ | |
| 382 | i-$C_3H_7$ | H | 0 | 5-Br | 3-F-4-$OCHF_2$ | |
| 383 | i-$C_3H_7$ | H | 0 | 5-Br | 3,5-$Cl_2$-4-$OCHF_2$ | |
| 384 | i-$C_3H_7$ | H | 0 | 5-Br | 3-$OCH_3$-4-$OCHF_2$ | |
| 385 | i-$C_3H_7$ | H | 0 | 5-Br | 3,4-$(OCHF_2)_2$ | |
| 386 | i-$C_3H_7$ | H | 0 | 5-Br | 2-$CH_3$-4-$OCF_3$ | |
| 387 | i-$C_3H_7$ | H | 0 | 5-Br | 2-$CH_3$-4-$OCHF_2$ | |
| 388 | i-$C_3H_7$ | H | 0 | 5-Br | 2-$CH_3$-4-$OCH_2CF_2CHF_2$ | |
| 389 | i-$C_3H_7$ | H | 0 | 5-Br | 2-$CH_3$-4-$OCBrF_2$ | |
| 390 | i-$C_3H_7$ | H | 0 | 5-Br | 2-$CH_3$-4-$OCF_2CHF_2$ | |
| 391 | i-$C_3H_7$ | H | 0 | 5-Br | 2-$CH_3$-4-$OCF_2CHF_2$-5-Cl | |
| 392 | i-$C_3H_7$ | H | 0 | 5-Br | 2-$CH_3$-4-$OCF_2CHClF$ | |
| 393 | i-$C_3H_7$ | H | 0 | 5-Br | 2-$CH_3$-4-$OCF_2CHFCF_3$ | |
| 394 | i-$C_3H_7$ | H | 0 | 5-Br | 2-$CH_3$-4-$OCF_2CBrFCF_3$ | |
| 395 | i-$C_3H_7$ | H | 0 | 5-Br | 2-$CH_3$-4-$OCF_2CHFOCF_3$ | |
| 396 | i-$C_3H_7$ | H | 0 | 5-Br | 2-$CH_3$-4-$OCHF_2$-5-Cl | |
| 397 | i-$C_3H_7$ | H | 0 | 5-Br | 2-$CH_3$-4-$(F_5$—PhO) | |
| 398 | i-$C_3H_7$ | H | 0 | 5-Br | 2-$CH_3$-4-(3-$CF_3$—PhO) | |
| 399 | i-$C_3H_7$ | H | 0 | 5-Br | 2-$CH_3$-4-(5-$CF_3$-2-Pyr—O) | |
| 400 | i-$C_3H_7$ | H | 0 | 2-$CH_3$ | 2-$CH_3$-4-$OCF_3$ | |
| 401 | i-$C_3H_7$ | H | 0 | 2-$CH_3$ | 2-$CH_3$-4-$CF_2CF_3$ | |
| 402 | i-$C_3H_7$ | H | 0 | 2-$CH_3$ | 2-$CH_3$-4-$CF_2CF_2CF_3$ | |
| 403 | i-$C_3H_7$ | H | 0 | 2-$CH_3$ | 2-$CH_3$-4-$CF(CF_3)_2$ | |
| 404 | i-$C_3H_7$ | H | 0 | 2-$CH_3$ | 2-$CH_3$-4-$(CF_2)_3CF_3$ | |
| 405 | i-$C_3H_7$ | H | 0 | 2-$CH_3$ | 2-Cl-4-$CF(CF_3)_2$ | |
| 406 | i-$C_3H_7$ | H | 0 | 2-$CH_3$ | 2-Cl-4-$(CF_2)_3CF_3$ | |
| 407 | i-$C_3H_7$ | H | 0 | 2-$CH_3$ | 2-$C_2H_5$-4-$CF(CF_3)_2$ | |
| 408 | i-$C_3H_7$ | H | 0 | 2-$CH_3$ | 2-F-4-$CF_2CF_3$ | |
| 409 | i-$C_3H_7$ | H | 0 | 2-$CF_3$ | 2-$CH_3$-4-$OCF_3$ | |
| 410 | i-$C_3H_7$ | H | 0 | 2-$CF_3$ | 2-$CH_3$-4-$CF_2CF_3$ | |
| 411 | i-$C_3H_7$ | H | 0 | 2-$CF_3$ | 2-$CH_3$-4-$CF_2CF_2CF_3$ | |
| 412 | i-$C_3H_7$ | H | 0 | 2-$CF_3$ | 2-$CH_3$-4-$CF(CF_3)_2$ | |
| 413 | i-$C_3H_7$ | H | 0 | 2-$CF_3$ | 2-$CH_3$-4-$(CF_2)_3CF_3$ | |
| 414 | i-$C_3H_7$ | H | 0 | 2-$CF_3$ | 2-Cl-4-$CF(CF_3)_2$ | |
| 415 | i-$C_3H_7$ | H | 0 | 2-$CF_3$ | 2-Cl-4-$(CF_2)_3CF_3$ | |
| 416 | i-$C_3H_7$ | H | 0 | 2-$CF_3$ | 2-$C_2H_5$-4-$CF(CF_3)_2$ | |
| 417 | i-$C_3H_7$ | H | 0 | 2-$CF_3$ | 2-F-4-$CF_2CF_3$ | |
| 418 | i-$C_3H_7$ | H | 0 | 2-$CF_3$ | 2-$C_2H_5$-4-$CF_2CF_3$ | |
| 419 | i-$C_3H_7$ | H | 0 | 2-$CF_3$ | 2-Br-4-$CF_2CF_3$ | |
| 420 | i-$C_3H_7$ | H | 0 | 5-$CH_3$ | 2-$CH_3$-4-$OCF_3$ | |
| 421 | i-$C_3H_7$ | H | 0 | 5-$CH_3$ | 2-$CH_3$-4-$CF_2CF_3$ | |
| 422 | i-$C_3H_7$ | H | 0 | 5-$CH_3$ | 2-$CH_3$-4-$CF_2CF_2CF_3$ | |
| 423 | i-$C_3H_7$ | H | 0 | 5-$CH_3$ | 2-$CH_3$-4-$CF(CF_3)_2$ | |
| 424 | i-$C_3H_7$ | H | 0 | 5-$CH_3$ | 2-$CH_3$-4-$(CF_2)_3CF_3$ | |
| 425 | i-$C_3H_7$ | H | 0 | 5-$CH_3$ | 2-Cl-4-$CF(CF_3)_2$ | |
| 426 | i-$C_3H_7$ | H | 0 | 5-$CH_3$ | 2-Cl-4-$(CF_2)_3CF_3$ | |
| 427 | i-$C_3H_7$ | H | 0 | 5-$CH_3$ | 2-$C_2H_5$-4-$CF(CF_3)_2$-i | |
| 428 | i-$C_3H_7$ | H | 0 | 5-$CH_3$ | 2-F-4-$CF_2CF_3$ | |
| 429 | i-$C_3H_7$ | H | 0 | 5-$CF_3$ | 2-$CH_3$-4-$OCF_3$ | |
| 430 | i-$C_3H_7$ | H | 0 | 5-$CF_3$ | 2-$CH_3$-4-$CF_3CF_3$ | |
| 431 | i-$C_3H_7$ | H | 0 | 5-$CF_3$ | 2-$CH_3$-4-$CF_2CF_2CF_3$ | |
| 432 | i-$C_3H_7$ | H | 0 | 5-$CF_3$ | 2-$CH_3$-4-$CF(CF_3)_2$ | |
| 433 | i-$C_3H_7$ | H | 0 | 5-$CF_3$ | 2-$CH_3$-4-$(CF_2)_3CF_3$ | |
| 434 | i-$C_3H_7$ | H | 0 | 5-$CF_3$ | 2-Cl-4-$CF(CF_3)_2$ | |
| 435 | i-$C_3H_7$ | H | 0 | 5-$CF_3$ | 2-Cl-4-$(CF_2)_3CF_3$ | |
| 436 | i-$C_3H_7$ | H | 0 | 5-$CF_3$ | 2-$C_2H_5$-4-$CF_2CF_3$ | |
| 437 | i-$C_3H_7$ | H | 0 | 5-$CF_3$ | 2-$C_2H_5$-4-$CF(CF_3)_2$ | |
| 438 | i-$C_3H_7$ | H | 0 | 5-$CF_3$ | 2-F-4-$CF_2CF_3$ | |
| 439 | i-$C_3H_7$ | H | 0 | 5-$CF_3$ | 2-Br-4-$CF_2CF_3$ | |
| 440 | i-$C_3H_7$ | H | 0 | 5-$CF_3$ | 2-Br-4-$CF(CF_3)_2$ | |

TABLE 3

($R^1$ = CH(CH$_3$)CH$_2$SCH$_3$, $R^3$ = H, $Z^1$ = $Z^2$ = O, Het = Q2, $B^1$ = $B^2$ = $B^3$ = $B^4$ = C)

| No | $R^2$ | p | Xn | Ym | Physical property m.p. °C. |
|---|---|---|---|---|---|
| 441 | H | 0 | H | 2-CH$_3$-4-OCF$_3$ | |
| 442 | H | 0 | H | 2-CH$_3$-4-CF$_2$CF$_3$ | |
| 443 | H | 0 | H | 2-CH$_3$-4-CF$_2$CF$_2$CF$_3$ | |
| 444 | H | 0 | H | 2-CH$_3$-4-CF(CF$_3$)$_2$ | |
| 445 | H | 0 | H | 2-CH$_3$-4-(CF$_2$)$_3$CF$_3$ | |
| 446 | H | 0 | H | 2-Cl-4-CF(CF$_3$)$_2$ | |
| 447 | H | 0 | H | 2-Cl-4-(CF$_2$)$_3$CF$_3$ | |
| 448 | H | 0 | H | 2-C$_2$H$_5$-4-CF$_2$CF$_3$ | |
| 449 | H | 0 | H | 2-C$_2$H$_5$-4-CF(CF$_3$)$_2$ | |
| 450 | H | 0 | H | 2-F-4-CF$_2$CF$_3$ | |
| 451 | H | 0 | H | 2-Br-4-CF$_2$CF$_3$ | |
| 452 | H | 0 | H | 2-Br-4-CF(CF$_3$)$_2$ | |
| 453 | H | 0 | 2-Cl | 2-CH$_3$-4-CF$_2$CF$_3$ | |
| 454 | H | 0 | 2-Cl | 2-CH$_3$-4-CF(CF$_3$)$_2$ | |
| 455 | H | 0 | 5-Cl | 2-CH$_3$-4-CF(CF$_3$)$_2$ | |
| 456 | H | 0 | 2-I | 2-CH$_3$-4-CF(CF$_3$)$_2$ | |
| 457 | H | 0 | 2-I | 2-CH$_3$-4-CF$_2$CF$_3$ | |
| 458 | H | 0 | 2-I | 2-Cl-4-CF(CF$_3$)$_2$ | |
| 459 | H | 0 | 5-I | 2-CH$_3$-4-CF(CF$_3$)$_2$ | |
| 460 | H | 0 | 5-I | 2-CH$_3$-4-CF$_2$CF$_3$ | |

TABLE 4

($R^1$ = C(CH$_3$)$_2$CH$_2$SCH$_3$, $R^3$ = H, $Z^1$ = $Z^2$ = O, Het = Q2, $B^1$ = $B^2$ = $B^3$ = $B^4$ = C)

| No | $R^2$ | p | Xn | Ym | Physical property m.p. °C. |
|---|---|---|---|---|---|
| 461 | H | 0 | H | 2-CH$_3$-4-OCF$_3$ | |
| 462 | H | 0 | H | 2-CH$_3$-4-CF$_2$CF$_3$ | |
| 463 | H | 0 | H | 2-CH$_3$-4-CF$_2$CF$_2$CF$_3$ | |
| 464 | H | 0 | H | 2-CH$_3$-4-CF(CF$_3$)$_2$ | 148–149 |
| 465 | H | 0 | H | 2-CH$_3$-4-(CF$_2$)$_3$CF$_3$ | |
| 466 | H | 0 | H | 2-Cl-4-CF(CF$_3$)$_2$ | |
| 467 | H | 0 | H | 2-Cl-4-(CF$_2$)$_3$CF$_3$ | |
| 468 | H | 0 | H | 2-C$_2$H$_5$-4-CF$_2$CF$_3$ | |
| 469 | H | 0 | H | 2-C$_2$H$_5$-4-CF(CF$_3$)$_2$ | |
| 470 | H | 0 | H | 2-F-4-CF$_2$CF$_3$ | |
| 471 | H | 0 | H | 2-Br-4-CF$_2$CF$_3$ | |

TABLE 4-continued ($R^1$ = C(CH$_3$)$_2$CH$_2$SCH$_3$, $R^3$ = H, $Z^1$ = $Z^2$ = O, Het = Q2, $B^1$ = $B^2$ = $B^3$ = $B^4$ = C)

| No | $R^2$ | p | Xn | Ym | Physical property m.p. °C. |
|---|---|---|---|---|---|
| 472 | H | 0 | H | 2-Br-4-CF(CF$_3$)$_2$ | |
| 473 | H | 0 | 2-Cl | 2-CH$_3$-4-CF$_2$CF$_3$ | |
| 474 | H | 0 | 2-Cl | 2-CH$_3$-4-CF(CF$_3$)$_2$ | |
| 475 | H | 0 | 5-I | 2-CH$_3$-4-CF(CF$_3$)$_2$ | |
| 476 | H | 0 | 2-I | 2-CH$_3$-4-CF(CF$_3$)$_2$ | |
| 477 | H | 0 | 2-I | 2-CH$_3$-4-CF$_2$CF$_3$ | |
| 478 | H | 0 | 2-I | 2-Cl-4-CF(CF$_3$)$_2$ | |
| 479 | H | 0 | 5-I | 2-CH$_3$-4-CF(CF$_3$)$_2$ | |
| 480 | H | 0 | 5-I | 2-CH$_3$-4-CF$_2$CF$_3$ | |

TABLE 5

($R^2$ = $R^3$ = H, $Z^1$ = $Z^2$ = O, Het = Q2, p = 0, $B^1$ = $B^2$ = $B^3$ = $B^4$ = C)

| No | $R^1$ | Xn | Ym | Physical property m.p. °C. |
|---|---|---|---|---|
| 481 | CH(CH$_3$)CH$_2$SC$_2$H$_5$ | H | 2-CH$_3$-4-OCF$_3$ | |
| 482 | CH(CH$_3$)CH$_2$SC$_2$H$_5$ | H | 2-CH$_3$-4-CF$_2$CF$_3$ | |
| 483 | CH(CH$_3$)CH$_2$SC$_2$H$_5$ | H | 2-CH$_3$-4-CF$_2$CF$_2$CF$_3$ | |
| 484 | C(CH$_3$)$_2$CH$_2$SOCH$_3$ | H | 2-CH$_3$-4-CF(CF$_3$)$_2$ | 180–182 |
| 485 | CH(CH$_3$)CH$_2$SC$_2$H$_5$ | 2-Cl | 2-CH$_3$-4-(CF$_2$)$_3$CF$_3$ | |
| 486 | CH(CH$_3$)CH$_2$SC$_2$H$_5$ | 2-I | 2-Cl-4-CF(CF$_3$)$_2$ | |
| 487 | C(CH$_3$)$_2$CH$_2$SC$_2$H$_5$ | H | 2-CH$_3$-4-OCF$_3$ | |
| 488 | C(CH$_3$)$_2$CH$_2$SC$_2$H$_5$ | H | 2-CH$_3$-4-CF$_2$CF$_3$ | |
| 489 | C(CH$_3$)$_2$CH$_2$SC$_2$H$_5$ | H | 2-CH$_3$-4-CF$_2$CF$_2$CF$_3$ | |
| 490 | C(CH$_3$)$_2$CH$_2$SC$_2$H$_5$ | 5-Cl | 2-CH$_3$-4-CF(CF$_3$)$_2$ | |
| 491 | C(CH$_3$)$_2$CH$_2$SC$_2$H$_5$ | 5-Br | 2-CH$_3$-4-(CF$_2$)$_3$CF$_3$ | |
| 492 | C(CH$_3$)$_2$CH$_2$SC$_2$H$_5$ | 5-I | 2-Cl-4-CF(CF$_3$)$_2$ | |
| 493 | CH(CH$_3$)CH$_2$NHAc | 2-Cl | 2-CH$_3$-4-OCF$_3$ | |
| 494 | CH(CH$_3$)CH$_2$NHAc | 5-Cl | 2-CH$_3$-4-CF$_2$CF$_3$ | |
| 495 | CH(CH$_3$)CH$_2$NHAc | 5-I | 2-CH$_3$-4-CF$_2$CF$_2$CF$_3$ | |
| 496 | CH(CH$_3$)CH$_2$NHAc | 2-I | 2-CH$_3$-4-CF(CF$_3$)$_2$ | |
| 497 | C(CH$_3$)$_2$CH$_2$NHAc | 2-Cl | 2-CH$_3$-4-(CF$_2$)$_3$CF$_3$ | |
| 498 | C(CH$_3$)$_2$CH$_2$NHAc | 5-I | 2-Cl-4-CF(CF$_3$)$_2$ | |
| 499 | CH(CH$_3$)C$_2$H$_4$OCH$_3$ | 2-Cl | 2-CH$_3$-4-CF(CF$_3$)$_2$ | |
| 500 | CH(CH$_3$)C$_2$H$_4$OCH$_3$ | 2-I | 2-CH$_3$-4-CF(CH$_3$)$_2$ | |
| 501 | C(CH$_3$)$_2$C$_2$H$_4$OCH$_3$ | 5-I | 2-CH$_3$-4-CF(CF$_3$)$_2$ | |

TABLE 6

($Z^1$ = $Z^2$ = O, $R^3$ = H, Het = Q3, $B^1$ = $B^2$ = $B^3$ = $B^4$ = C)

| No | $R^1$ | $R^2$ | p | Xn | Ym | Physical property m.p. °C. |
|---|---|---|---|---|---|---|
| 502 | i-C$_3$H$_7$ | H | 0 | H | 2-CH$_3$-4-CF$_3$ | |
| 503 | i-C$_3$H$_7$ | H | 0 | H | 2-CH$_3$-4-OCHF$_2$ | |
| 504 | i-C$_3$H$_7$ | H | 0 | H | 2-CH$_3$-4-OCF$_3$ | |
| 505 | i-C$_3$H$_7$ | H | 0 | H | 2-CH$_3$-4-OCBrF$_2$ | |
| 506 | i-C$_3$H$_7$ | H | 0 | H | 2-CH$_3$-4-OCF$_2$CHF$_2$ | |
| 507 | i-C$_3$H$_7$ | H | 0 | H | 2-CH$_3$-3-OCF$_2$CHClF | |
| 508 | i-C$_3$H$_7$ | H | 0 | H | 2-CH$_3$-4-OCF$_2$CCl$_2$F | |
| 509 | i-C$_3$H$_7$ | H | 0 | H | 2-CH$_3$-4-OCF$_2$CBrF$_2$ | |
| 510 | i-C$_3$H$_7$ | H | 0 | H | 2-CH$_3$-4-OCH$_2$CF$_2$CHF$_2$ | |
| 511 | i-C$_3$H$_7$ | H | 0 | H | 2-CH$_3$-4-CF$_2$CF$_3$ | |
| 512 | i-C$_3$H$_7$ | H | 0 | H | 2-CH$_3$-4-CF(CF$_3$)$_2$ | 206–208 |
| 513 | i-C$_3$H$_7$ | H | 0 | H | 2-CH$_3$-4-SCF$_2$CBrF$_2$ | |
| 514 | i-C$_3$H$_7$ | H | 0 | H | 2-CH$_3$-4-SCH$_2$CF$_2$CHF$_2$ | |
| 515 | i-C$_3$H$_7$ | H | 0 | H | 2-CH$_3$-4-SO$_2$CH$_2$CF$_2$CHF$_2$ | |

TABLE 6-continued ($Z^1 = Z^2 = O$, $R^3 = H$, Het = Q3, $B^1 = B^2 = B^3 = B^4 = C$)

| No | $R^1$ | $R^2$ | p | Xn | Ym | Physical property m.p. ° C. |
|---|---|---|---|---|---|---|
| 516 | i-$C_3H_7$ | H | 0 | H | 2-Cl-4-$CF_3$ | |
| 517 | i-$C_3H_7$ | H | 0 | H | 2-Cl-4-CF($CF_2$)$_2$ | |
| 518 | i-$C_3H_7$ | H | 0 | H | 3-Cl-4-$OCHF_2$ | |
| 519 | i-$C_3H_7$ | H | 0 | H | 3-F-4-$OCHF_2$ | |
| 520 | i-$C_3H_7$ | H | 0 | H | 2-Cl-4-$OCF_3$ | |
| 521 | i-$C_3H_7$ | H | 1 | H | 2-$CH_3$-4-$CF_2CF_3$ | |
| 522 | i-$C_3H_7$ | H | 1 | H | 2-$CH_3$-4-CF($CF_3$)$_2$ | |
| 523 | i-$C_3H_7$ | H | 0 | 2-Cl | 2-$CH_3$-4-$CF_2CF_3$ | |
| 524 | i-$C_3H_7$ | H | 0 | 2-Cl | 2-$CH_3$-4-CF($CF_3$)$_2$ | 275–277 |
| 525 | i-$C_3H_7$ | H | 0 | 2-Cl | 2-$CH_3$-4-$OCF_2$CBrF$CF_3$ | |
| 526 | i-$C_3H_7$ | H | 0 | 2-Cl | 2-$CH_3$-4-$OCF_2$CHFO$CF_3$ | |
| 527 | i-$C_3H_7$ | H | 0 | 2-Cl | 2-$CH_3$-4-$OCHF_2$-5-Cl | |
| 528 | i-$C_3H_7$ | H | 0 | 2-Cl | 2-$CH_3$-4-$OCF_2CHF_2$-5-Cl | |
| 529 | i-$C_3H_7$ | H | 0 | 2-Cl | 2-$CH_3$-4-$SCHF_2$ | |
| 530 | i-$C_3H_7$ | H | 0 | 2-Cl | 2-$CH_3$-4-($F_5$—PhO) | |
| 531 | i-$C_3H_7$ | H | 0 | 2-Cl | 2-$CH_3$-4-(5-$CF_3$-2-Pyr—O) | |
| 532 | i-$C_3H_7$ | H | 0 | 2-Cl | 2-$CH_3$-4-(3-Cl-5-$CF_3$-2-Pyr—O) | |
| 533 | i-$C_3H_7$ | H | 0 | 2-Cl | 2-$CH_3$-4-P=O(O$C_2H_5$)$_2$ | |
| 534 | i-$C_3H_7$ | H | 0 | 2-Cl | 2-$CH_3$-4-OP=S(O$CH_3$)$_2$ | |
| 535 | i-$C_3H_7$ | H | 0 | 2-Cl | 2-$CF_3$-4-$OCHF_2$ | |
| 536 | i-$C_3H_7$ | H | 0 | 2-Cl | 3-$CF_3$-4-$OCHF_2$ | |
| 537 | i-$C_3H_7$ | H | 0 | 2-Cl | 3-N=C($CF_3$)—O-4 | |
| 538 | i-$C_3H_7$ | H | 0 | 2-Cl | 3-N=C($CF_3$)—NH-4 | |
| 540 | i-$C_3H_7$ | H | 0 | 2-Cl | 3-N=C($CF_3$)—N($CH_3$)-4 | |
| 541 | i-$C_3H_7$ | H | 0 | 2-Cl | 2-$CH_3$-4-$OCHF_2$ | |
| 542 | i-$C_3H_7$ | H | 0 | 2-Br | 2-$CH_3$-4-$CF_3$ | |
| 543 | i-$C_3H_7$ | H | 0 | 2-Br | 2-$CH_3$-4-$OCHF_2$ | |
| 544 | i-$C_3H_7$ | H | 0 | 2-Br | 2-$CH_3$-4-$OCF_3$ | |
| 545 | i-$C_3H_7$ | H | 0 | 2-Br | 2-$CH_3$-4-$OCBrF_2$ | |
| 546 | i-$C_3H_7$ | H | 0 | 2-Br | 2-$CH_3$-4-$OCF_2CHF_2$ | |
| 547 | i-$C_3H_7$ | H | 0 | 2-Br | 2-$CH_3$-3-$OCF_2$CHClF | |
| 548 | i-$C_3H_7$ | H | 0 | 2-Br | 2-$CH_3$-4-$OCF_2CCl_2$F | |
| 549 | i-$C_3H_7$ | H | 0 | 2-Br | 2-$CH_3$-4-$OCF_2$CBr$F_2$ | |
| 550 | i-$C_3H_7$ | H | 0 | 2-Br | 2-$CH_3$-4-$OCH_2CF_2CHF_2$ | |
| 551 | i-$C_3H_7$ | H | 0 | 2-Br | 2-$CH_3$-4-$CF_2CF_3$ | |
| 552 | i-$C_3H_7$ | H | 0 | 2-Br | 2-$CH_3$-4-CF($CF_3$)$_2$ | |
| 553 | i-$C_3H_7$ | H | 0 | 2-Br | 2-$CH_3$-4-$SCF_2$CBr$F_2$ | |
| 554 | i-$C_3H_7$ | H | 0 | 2-Br | 2-$CH_3$-4-$SCH_2CF_2CHF_2$ | |
| 555 | i-$C_3H_7$ | H | 0 | 2-Br | 2-$CH_3$-4-$SO_2CH_2CF_2CHF_2$ | |
| 556 | i-$C_3H_7$ | H | 0 | 2-Br | 2-Cl-4-$CF_3$ | |
| 557 | i-$C_3H_7$ | H | 0 | 2-Br | 2-Cl-4-CF($CF_2$)$_2$ | |
| 558 | i-$C_3H_7$ | H | 0 | 2-Br | 3-Cl-4-$OCHF_2$ | |
| 559 | i-$C_3H_7$ | H | 0 | 2-Br | 3-F-4-$OCHF_2$ | |
| 560 | i-$C_3H_7$ | H | 0 | 2-Br | 2-Cl-4-$OCF_3$ | |
| 561 | i-$C_3H_7$ | H | 0 | 2-Br | 2-Br-4-$OCF_3$ | |
| 562 | i-$C_3H_7$ | H | 0 | 2-Br | 3,5-$Cl_2$-4-$OCHF_2$ | |
| 563 | i-$C_3H_7$ | H | 0 | 2-I | 2-$CH_3$-4-CF($CF_3$)$_2$ | |
| 564 | i-$C_3H_7$ | H | 0 | 2-I | 2-$CH_3$-4-($CF_2$)$_3CF_3$ | |
| 565 | i-$C_3H_7$ | H | 0 | 2-I | 2-$CH_3$-4-$OCH_3$ | |
| 566 | i-$C_3H_7$ | H | 0 | 2-I | 2-$CH_3$-4-$OCH_2CF_2CHF_2$ | |
| 567 | i-$C_3H_7$ | H | 0 | 2-I | 2,4-($CH_3$)$_2$-3-$OCHF_2$ | |
| 568 | i-$C_3H_7$ | H | 0 | 2-I | 2,3-($CH_3$)$_2$-4-$OCH_3$ | |
| 569 | i-$C_3H_7$ | H | 0 | 2-I | 2-Cl-4-$OCF_3$ | |
| 570 | i-$C_3H_7$ | H | 0 | 2-I | 2-Br-4-$OCF_3$ | |
| 571 | i-$C_3H_7$ | H | 0 | 2-I | 2-$CH_3$-4-$OCHF_2$ | |
| 572 | i-$C_3H_7$ | H | 0 | 2-I | 2-$CH_3$-4-$OCF_3$ | |
| 573 | i-$C_3H_7$ | H | 0 | 2-I | 2-$CH_3$-4-$OCBrF_2$ | |
| 574 | i-$C_3H_7$ | H | 0 | 2-I | 2-$CH_3$-4-$OCF_2$CHF$CF_3$ | |
| 575 | i-$C_3H_7$ | R | 0 | 2-I | 2-$CH_3$-4-$OCF_2$CHClF | |
| 576 | i-$C_3H_7$ | H | 0 | 2-I | 2-$CH_3$-4-$OCF_2CHF_2$ | |
| 577 | i-$C_3H_7$ | H | 0 | 2-I | 2-$CH_3$-3-Cl-4-$OCHF_2$ | |
| 578 | i-$C_3H_7$ | H | 0 | 2-I | 2,3-($CH_3$)$_2$-4-$OCHF_2$ | |
| 579 | i-$C_3H_7$ | H | 0 | 2-I | 2-$CH_3$-4-$SCH_3$ | |
| 580 | i-$C_3H_7$ | H | 0 | 2-I | 2-(3-$CF_3$—PhO) | |
| 581 | i-$C_3H_7$ | H | 0 | 2-I | 2-$CH_3$-4-(3-Cl-5-$CF_3$-2-Pyr—O) | |
| 582 | i-$C_3H_7$ | H | 0 | 5-Cl | 2-$CH_3$-4-(5-$CF_3$-2-Pyr—O) | |
| 583 | i-$C_3H_7$ | H | 0 | 5-Cl | -3-$OCH_2$O-4- | |
| 584 | i-$C_3H_7$ | H | 0 | 5-Cl | 4-$CF_3$ | |
| 585 | i-$C_3H_7$ | H | 0 | 5-Cl | 4-$OCF_3$ | |
| 586 | i-$C_3H_7$ | H | 0 | 5-Cl | 2,3-($CH_3$)$_2$ | |
| 587 | i-$C_3H_7$ | H | 0 | 5-Cl | 2,4,6-($CH_3$)$_3$ | |

TABLE 6-continued ($Z^1 = Z^2 = O, R^3 = H, Het = Q3, B^1 = B^2 = B^3 = B^4 = C$)

| No | $R^1$ | $R^2$ | p | Xn | Ym | Physical property m.p. ° C. |
|---|---|---|---|---|---|---|
| 588 | i-$C_3H_7$ | H | 0 | 5-Cl | 2-$CH_3$-3-Cl | |
| 589 | i-$C_3H_7$ | H | 0 | 5-Cl | 2-$CH_3$-4-Cl | |
| 590 | i-$C_3H_7$ | H | 0 | 5-Cl | 2-$CH_3$-5-Cl | |
| 591 | i-$C_3H_7$ | H | 0 | 5-Cl | 2,3-$(CH_3)_2$-4-Cl | |
| 592 | i-$C_3H_7$ | H | 0 | 5-Cl | 2,4-$(CH_3)_2$-3-Cl | |
| 593 | i-$C_3H_7$ | H | 0 | 5-Cl | 2-$C_2H_5$-4-Cl | |
| 594 | i-$C_3H_7$ | H | 0 | 5-Cl | 2-$CH_3$-4-Br | |
| 595 | i-$C_3H_7$ | H | 0 | 5-Cl | 2,3-$(CH_3)_2$-4-Br | |
| 596 | i-$C_3H_7$ | H | 0 | 5-Cl | 2-$CH_3$-4-I | |
| 597 | i-$C_3H_7$ | H | 0 | 5-Cl | 2-$CH_3$-4-F | |
| 598 | i-$C_3H_7$ | H | 0 | 5-Cl | 2-Cl-4-$CF_3$ | |
| 599 | i-$C_3H_7$ | H | 0 | 5-Cl | 2-$CH_3$-4-$CF_3$ | |
| 600 | i-$C_3H_7$ | H | 0 | 5-Cl | 2-$CH_3$-4-$CF(CF_3)_2$ | |
| 601 | i-$C_3H_7$ | H | 0 | 5-Cl | 2-$CH_3$-4-$(CF_2)_3CF_3$ | |
| 602 | i-$C_3H_7$ | H | 0 | 5-Cl | 2-$CH_3$-4-$OCH_2CF_2CHF_2$ | |
| 603 | i-$C_3H_7$ | H | 0 | 5-Cl | 2,4-$(CH_3)_2$-3-$OCHF_2$ | |
| 604 | i-$C_3H_7$ | H | 0 | 5-Cl | 2,3-$(CH_3)_2$-4-$OCH_3$ | |
| 605 | i-$C_3H_7$ | H | 0 | 5-Cl | 2-$CH_3$-4-$OCH_3$ | |
| 606 | i-$C_3H_7$ | H | 0 | 5-Cl | 2-Cl-4-$OCF_3$ | |
| 607 | i-$C_3H_7$ | H | 0 | 5-Cl | 2-Br-4-$OCF_3$ | |
| 608 | i-$C_3H_7$ | H | 0 | 5-Cl | 2-$CH_3$-4-$OCHF_2$ | |
| 609 | i-$C_3H_7$ | H | 0 | 5-Cl | 2-$CH_3$-4-$OCF_3$ | |
| 610 | i-$C_3H_7$ | H | 0 | 5-Cl | 2-$CH_3$-4-$OCBrF_2$ | |
| 611 | i-$C_3H_7$ | H | 0 | 5-Cl | 2-$CH_3$-4-$OCF_2CHFCF_3$ | |
| 612 | i-$C_3H_7$ | H | 0 | 5-Cl | 2-$CH_3$-4-$OCF_2CHClF$ | |
| 613 | i-$C_3H_7$ | H | 0 | 5-Cl | 2-$CH_3$-4-$OCF_2CHF_2$ | |
| 614 | i-$C_3H_7$ | H | 0 | 5-Cl | 2,3-$(CH_3)_2$-4-$OCHF_2$ | |
| 615 | i-$C_3H_7$ | H | 0 | 5-Cl | 2-$CH_3$-3-Cl-4-$OCHF_2$ | |
| 616 | i-$C_3H_7$ | H | 0 | 5-Cl | 2-$CH_3$-4-$SCH_3$ | |
| 617 | i-$C_3H_7$ | H | 0 | 5-Cl | 2-$CH_3$-4-(3-$CF_3$—PhO) | |
| 618 | i-$C_3H_7$ | H | 0 | 5-Cl | 2-$CH_3$-4-(5-$CF_3$-2-Pyr—O) | |
| 619 | i-$C_3H_7$ | H | 0 | 5-Cl | 2-$CH_3$-4-(3-Cl-5-$CF_3$-2-Pyr—O) | |
| 620 | i-$C_3H_7$ | H | 0 | 5-Cl | -3-$OCH_2$O-4- | |
| 621 | i-$C_3H_7$ | H | 0 | 5-Cl | 2-Cl-4-$OCHF_2$ | |
| 622 | i-$C_3H_7$ | H | 0 | 5-I | 4-Cl | |
| 623 | i-$C_3H_7$ | H | 0 | 5-I | 4-Br | |
| 624 | i-$C_3H_7$ | H | 0 | 5-I | 4-I | |
| 625 | i-$C_3H_7$ | H | 0 | 5-I | 3-$CF_3$ | |
| 626 | i-$C_3H_7$ | H | 0 | 5-I | 4-$CF_3$ | |
| 627 | i-$C_3H_7$ | H | 0 | 5-I | 4-$CF_2CF_2CF_3$ | |
| 628 | i-$C_3H_7$ | H | 0 | 5-I | 4-$CF(CF_3)_2$ | |
| 629 | i-$C_3H_7$ | H | 0 | 5-I | 4-$OCF_3$ | |
| 630 | i-$C_3H_7$ | H | 0 | 5-I | 4-$OCF_2CHFOCF_3$ | |
| 631 | i-$C_3H_7$ | H | 0 | 5-I | 4-$SCHF_2$ | |
| 632 | i-$C_3H_7$ | H | 0 | 5-I | 4-$SCH_2CF_3$ | |
| 633 | i-$C_3H_7$ | H | 0 | 5-I | 4-$SCF_2CHF_2$ | |
| 634 | i-$C_3H_7$ | H | 0 | 5-I | 4-$SCF_2CBrF_2$ | |
| 635 | i-$C_3H_7$ | H | 0 | 5-I | 4-$SCF(CF_3)_2$ | |
| 636 | i-$C_3H_7$ | H | 0 | 5-I | 4-$S(CF_2)_3CF_3$ | |
| 637 | i-$C_3H_7$ | H | 0 | 5-I | 3,4-$F_2$ | |
| 638 | i-$C_3H_7$ | H | 0 | 5-I | 2-$CH_3$-3-Cl | |
| 639 | i-$C_3H_7$ | H | 0 | 5-I | 2-$CH_3$-4-Cl | |
| 640 | i-$C_3H_7$ | H | 0 | 5-I | 2-$CH_3$-5-Cl | |
| 641 | i-$C_3H_7$ | H | 0 | 5-I | 2,4-$(CH_3)_2$-3-Cl | |
| 642 | i-$C_3H_7$ | H | 0 | 5-I | 2,3-$(CH_3)_2$-4-Cl | |
| 643 | i-$C_3H_7$ | H | 0 | 5-I | 2-Cl-4-$CF_3$ | |
| 644 | i-$C_3H_7$ | H | 0 | 5-I | 2-Cl-4-$CF_2CF_3$ | |
| 645 | i-$C_3H_7$ | H | 0 | 5-I | 2-Cl-4-$CF_2CF_2CF_3$ | |
| 646 | i-$C_3H_7$ | H | 0 | 5-I | 2-Cl-4-$CF(CF_3)_2$ | |
| 647 | i-$C_3H_7$ | H | 0 | 5-I | 2-Cl-4-$(CF_2)_3CF_3$ | |
| 648 | i-$C_3H_7$ | H | 0 | 5-I | 2-$C_2H_5$-4-$CF(CF_3)_2$ | |
| 649 | i-$C_3H_7$ | H | 0 | 5-I | 2-$CH_3$-4-Br | |
| 650 | i-$C_3H_7$ | H | 0 | 5-I | 2-$CH_3$-4-I | |
| 651 | i-$C_3H_7$ | H | 0 | 5-I | 2-$CH_3$-4-F | |
| 652 | i-$C_3H_7$ | H | 0 | 5-I | 2-Cl-4-$CF_3$ | |
| 653 | i-$C_3H_7$ | H | 0 | 5-I | 2-$CH_3$-3-$CF_3$ | |
| 654 | i-$C_3H_7$ | H | 0 | 5-I | 2-$CH_3$-4-$CF_3$ | |
| 655 | i-$C_3H_7$ | H | 0 | 5-I | 2-$CH_3$-4-$CF_2CF_3$ | |
| 656 | i-$C_3H_7$ | H | 0 | 5-I | 2-$CH_3$-4-$CF_2CF_2CF_3$ | |

TABLE 6-continued ($Z^1 = Z^2 = O, R^3 = H, Het = Q3, B^1 = B^2 = B^3 = B^4 = C$)

| No | $R^1$ | $R^2$ | p | Xn | Ym | Physical property m.p. °C. |
|---|---|---|---|---|---|---|
| 657 | i-$C_3H_7$ | H | 0 | 5-I | 2-$CH_3$-4-CF($CF_3$)$_2$ | |
| 658 | i-$C_3H_7$ | H | 0 | 5-I | 2-$CH_3$-4-($CF_2$)$_3CF_3$ | |
| 659 | i-$C_3H_7$ | H | 0 | 5-I | 2-$CH_3$-4-$OCH_3$ | |
| 660 | i-$C_3H_7$ | H | 0 | 5-I | 2-$CH_3$-4-O—$C_3H_7$-i | |
| 661 | i-$C_3H_7$ | H | 0 | 5-I | 2,3-($CH_3$)$_2$-4-$OCH_3$ | |
| 662 | i-$C_3H_7$ | H | 0 | 5-I | 2-$CH_3$-4-$OCH_2CF_3$ | |
| 663 | i-$C_3H_7$ | H | 0 | 5-I | 2-$CH_3$-4-$OCF_2CBrF_2$ | |
| 664 | i-$C_3H_7$ | H | 0 | 5-Br | 2-$CH_3$-4-$OCF_2CCl_2F$ | |
| 665 | i-$C_3H_7$ | H | 0 | 5-Br | 3-F-4-$OCHF_2$ | |
| 666 | i-$C_3H_7$ | H | 0 | 5-Br | 3,5-$Cl_2$-4-$OCHF_2$ | |
| 667 | i-$C_3H_7$ | H | 0 | 5-Br | 3-$OCH_3$-4-$OCHF_2$ | |
| 668 | i-$C_3H_7$ | H | 0 | 5-Br | 3,4-($OCHF_2$)$_2$ | |
| 669 | i-$C_3H_7$ | H | 0 | 5-Br | 2-$CH_3$-4-$OCF_3$ | |
| 670 | i-$C_3H_7$ | H | 0 | 5-Br | 2-$CH_3$-4-$OCHF_2$ | |
| 671 | i-$C_3H_7$ | H | 0 | 5-Br | 2-$CH_3$-4-$OCH_2CF_2CHF_2$ | |
| 672 | i-$C_3H_7$ | H | 0 | 5-Br | 2-$CH_3$-4-$OCBrF_2$ | |
| 673 | i-$C_3H_7$ | H | 0 | 5-Br | 2-$CH_3$-4-$OCF_2CHF_2$ | |
| 674 | i-$C_3H_7$ | H | 0 | 5-Br | 2-$CH_3$-4-$OCF_2CHF_2$-5-Cl | |
| 675 | i-$C_3H_7$ | H | 0 | 5-Br | 2-$CH_3$-4-$OCF_2CHClF$ | |
| 676 | i-$C_3H_7$ | H | 0 | 5-Br | 2-$CH_3$-4-$OCF_2CHFCF_3$ | |
| 677 | i-$C_3H_7$ | H | 0 | 5-Br | 2-$CH_3$-4-$OCF_2CBrFCF_3$ | |
| 678 | i-$C_3H_7$ | H | 0 | 5-Br | 2-$CH_3$-4-$OCF_2CHFOCF_3$ | |
| 679 | i-$C_3H_7$ | H | 0 | 5-Br | 2-$CH_3$-4-$OCHF_2$-5-Cl | |
| 680 | i-$C_3H_7$ | H | 0 | 5-Br | 2-$CH_3$-4-($F_5$—PhO) | |
| 681 | i-$C_3H_7$ | H | 0 | 5-Br | 2-$CH_3$-4-(3-$CF_3$—PhO) | |
| 682 | i-$C_3H_7$ | H | 0 | 5-Br | 2-$CH_3$-4-(5-$CF_3$-2-Pyr—O) | |
| 683 | i-$C_3H_7$ | H | 0 | 2-$CH_3$ | 2-$CH_3$-4-$OCF_3$ | |
| 684 | i-$C_3H_7$ | H | 0 | 2-$CH_3$ | 2-$CH_3$-4-$CF_2CF_3$ | |
| 685 | i-$C_3H_7$ | H | 0 | 2-$CH_3$ | 2-$CH_3$-4-$CF_2CF_2CF_3$ | |
| 686 | i-$C_3H_7$ | H | 0 | 2-$CH_3$ | 2-$CH_3$-4-CF($CF_3$)$_2$ | |
| 687 | i-$C_3H_7$ | H | 0 | 2-$CH_3$ | 2-$CH_3$-4-($CF_2$)$_3CF_3$ | |
| 688 | i-$C_3H_7$ | H | 0 | 2-$CH_3$ | 2-Cl-4-CF($CF_3$)$_2$ | |
| 689 | i-$C_3H_7$ | H | 0 | 2-$CH_3$ | 2-Cl-4-($CF_2$)$_3CF_3$ | |
| 690 | i-$C_3H_7$ | H | 0 | 2-$CH_3$ | 2-$C_2H_5$-4-CF($CF_3$)$_2$ | |
| 691 | i-$C_3H_7$ | H | 0 | 2-$CH_3$ | 2-F-4-$CF_2CF_3$ | |
| 692 | i-$C_3H_7$ | H | 0 | 2-$CF_3$ | 2-$CH_3$-4-$OCF_3$ | |
| 693 | i-$C_3H_7$ | H | 0 | 2-$CF_3$ | 2-$CH_3$-4-$CF_2CF_3$ | |
| 694 | i-$C_3H_7$ | H | 0 | 2-$CF_3$ | 2-$CH_3$-4-$CF_2CF_2CF_3$ | |
| 695 | i-$C_3H_7$ | H | 0 | 2-$CF_3$ | 2-$CH_3$-4-CF($CF_3$)$_2$ | |
| 696 | i-$C_3H_7$ | H | 0 | 2-$CF_3$ | 2-$CH_3$-4-($CF_2$)$_3CF_3$ | |
| 697 | i-$C_3H_7$ | H | 0 | 2-$CF_3$ | 2-Cl-4-CF($CF_3$)$_2$ | |
| 698 | i-$C_3H_7$ | H | 0 | 2-$CF_3$ | 2-Cl-4-($CF_2$)$_3CF_3$ | |
| 699 | i-$C_3H_7$ | H | 0 | 2-$CF_3$ | 2-$C_2H_5$-4-CF($CF_3$)$_2$ | |
| 700 | i-$C_3H_7$ | H | 0 | 2-$CF_3$ | 2-F-4-$CF_2CF_3$ | |
| 701 | i-$C_3H_7$ | H | 0 | 2-$CF_3$ | 2-$C_2H_5$-4-$CF_2CF_3$ | |
| 702 | i-$C_3H_7$ | H | 0 | 2-$CF_3$ | 2-Br-4-$CF_2CF_3$ | |
| 703 | i-$C_3H_7$ | H | 0 | 5-$CH_3$ | 2-$CH_3$-4-$OCF_3$ | |
| 704 | i-$C_3H_7$ | H | 0 | 5-$CH_3$ | 2-$CH_3$-4-$CF_2CF_3$ | |
| 705 | i-$C_3H_7$ | H | 0 | 5-$CH_3$ | 2-$CH_3$-4-$CF_2CF_2CF_3$ | |
| 706 | i-$C_3H_7$ | H | 0 | 5-$CH_3$ | 2-$CH_3$-4-CF($CF_3$)$_2$ | |
| 707 | i-$C_3H_7$ | H | 0 | 5-$CH_3$ | 2-$CH_3$-4-($CF_2$)$_3CF_3$ | |
| 708 | i-$C_3H_7$ | H | 0 | 5-$CH_3$ | 2-Cl-4-CF($CF_3$)$_2$ | |
| 709 | i-$C_3H_7$ | H | 0 | 5-$CH_3$ | 2-Cl-4-($CF_2$)$_3CF_3$ | |
| 710 | i-$C_3H_7$ | H | 0 | 5-$CH_3$ | 2-$C_2H_5$-4-CF($CF_3$)$_2$ | |
| 711 | i-$C_3H_7$ | H | 0 | 5-$CH_3$ | 2-F-4-$CF_2CF_3$ | |
| 712 | i-$C_3H_7$ | H | 0 | 5-$CF_3$ | 2-$CH_3$-4-$OCF_3$ | |
| 713 | i-$C_3H_7$ | H | 0 | 5-$CF_3$ | 2-$CH_3$-4-$CF_2CF_3$ | |
| 714 | i-$C_3H_7$ | H | 0 | 5-$CF_3$ | 2-$CH_3$-4-$CF_2CF_2CF_3$ | |
| 715 | i-$C_3H_7$ | H | 0 | 5-$CF_3$ | 2-$CH_3$-4-CF($CF_3$)$_2$ | |
| 716 | i-$C_3H_7$ | H | 0 | 5-$CF_3$ | 2-$CH_3$-4-($CF_2$)$_3CF_3$ | |
| 717 | i-$C_3H_7$ | H | 0 | 5-$CF_3$ | 2-Cl-4-CF($CF_3$)$_2$ | |
| 718 | i-$C_3H_7$ | H | 0 | 5-$CF_3$ | 2-Cl-4-($CF_2$)$_3CF_3$ | |
| 719 | i-$C_3H_7$ | H | 0 | 5-$CF_3$ | 2-$C_2H_5$-4-$CF_2CF_3$ | |
| 720 | i-$C_3H_7$ | H | 0 | 5-$CF_3$ | 2-$C_2H_5$-4-CF($CF_3$)$_2$ | |
| 721 | i-$C_3H_7$ | H | 0 | 5-$CF_3$ | 2-F-4-$CF_2CF_3$ | |
| 722 | i-$C_3H_7$ | H | 0 | 5-$CF_3$ | 2-Br-4-$CF_2CF_3$ | |
| 723 | i-$C_3H_7$ | H | 0 | 5-$CF_3$ | 2-Br-4-CF($CF_3$)$_2$ | |

TABLE 7

($R^1$ = CH(CH$_3$)CH$_2$SCH$_3$, $R^3$ = H, $Z^1$ = $Z^2$ = O, Het = Q3, $B^1$ = $B^2$ = $B^3$ = $B^4$ = C)

| No | $R^2$ | p | Xn | Ym | Physical property m.p. ° C. |
|---|---|---|---|---|---|
| 724 | H | 0 | H | 2-CH$_3$-4-OCF$_3$ | |
| 725 | H | 0 | H | 2-CH$_3$-4-CF$_2$CF$_3$ | |
| 726 | H | 0 | H | 2-CH$_3$-4-CF$_2$CF$_2$CF$_3$ | |
| 727 | H | 0 | H | 2-CH$_3$-4-CF(CF$_3$)$_2$ | |
| 728 | H | 0 | H | 2-CH$_3$-4-(CF$_2$)$_3$CF$_3$ | |
| 729 | H | 0 | H | 2-Cl-4-CF(CF$_3$)$_2$ | |
| 730 | H | 0 | H | 2-Cl-4-(CF$_2$)$_3$CF$_3$ | |
| 731 | H | 0 | H | 2-C$_2$H$_5$-4-CF$_2$CF$_3$ | |
| 732 | H | 0 | H | 2-C$_2$H$_5$-4-CF(CF$_3$)$_2$ | |
| 733 | H | 0 | H | 2-F-4-CF$_2$CF$_3$ | |
| 734 | H | 0 | H | 2-Br-4-CF$_2$CF$_3$ | |
| 735 | H | 0 | H | 2-Br-4-CF(CF$_3$)$_2$ | |
| 736 | H | 0 | 2-Cl | 2-CH$_3$-4-CF$_2$CF$_3$ | |
| 737 | H | 0 | 2-Cl | 2-CH$_3$-4-CF(CF$_3$)$_2$ | 237–239 |
| 738 | H | 0 | 5-Cl | 2-CH$_3$-4-CF(CF$_3$)$_2$ | |
| 739 | H | 0 | 2-I | 2-CH$_3$-4-CF(CF$_3$)$_2$ | |
| 740 | H | 0 | 2-I | 2-CH$_3$-4-CF$_2$CF$_3$ | |
| 741 | H | 0 | 2-I | 2-Cl-4-CF(CF$_3$)$_2$ | |
| 742 | H | 0 | 5-I | 2-CH$_3$-4-CF(CF$_3$)$_2$ | |
| 743 | H | 0 | 5-I | 2-CH$_3$-4-CF$_2$CF$_3$ | |

TABLE 8

($R^1$ = C(CH$_3$)$_2$CH$_2$SCH$_3$, $R^3$ = H, $Z^1$ = $Z^2$ = O, Het = Q3, $B^1$ = $B^2$ = $B^3$ = $B^4$ = C)

| No | $R^2$ | p | Xn | Ym | Physical property m.p. ° C. |
|---|---|---|---|---|---|
| 744 | H | 0 | H | 2-CH$_3$-4-OCF$_3$ | |
| 745 | H | 0 | H | 2-CH$_3$-4-CF$_2$CF$_3$ | |
| 746 | H | 0 | H | 2-CH$_3$-4-CF$_2$CF$_2$CF$_3$ | |
| 747 | H | 0 | H | 2-CH$_3$-4-CF(CF$_3$)$_2$ | |
| 748 | H | 0 | H | 2-CH$_3$-4-(CF$_2$)$_3$CF$_3$ | |
| 749 | H | 0 | H | 2-Cl-4-CF(CF$_3$)$_2$ | |
| 750 | H | 0 | H | 2-Cl-4-(CF$_2$)$_3$CF$_3$ | |
| 751 | H | 0 | H | 2-C$_2$H$_5$-4-CF$_2$CF$_3$ | |
| 752 | H | 0 | H | 2-C$_2$H$_5$-4-CF(CF$_3$)$_2$ | |
| 753 | H | 0 | H | 2-F-4-CF$_2$CF$_3$ | |
| 754 | H | 0 | H | 2-Br-4-CF$_2$CF$_3$ | |

TABLE 8-continued ($R^1$ = C(CH$_3$)$_2$CH$_2$SCH$_3$, $R^3$ = H, $Z^1$ = $Z^2$ = O, Het = Q3, $B^1$ = $B^2$ = $B^3$ = $B^4$ = C)

| No | $R^2$ | p | Xn | Ym | Physical property m.p. ° C. |
|---|---|---|---|---|---|
| 755 | H | 0 | H | 2-Br-4-CF(CF$_3$)$_2$ | |
| 756 | H | 0 | 2-Cl | 2-CH$_3$-4-CF$_2$CF$_3$ | |
| 757 | H | 0 | 2-Cl | 2-CH$_3$-4-CF(CF$_3$)$_2$ | |
| 758 | H | 0 | 5-I | 2-CH$_3$-4-CF(CF$_3$)$_2$ | |
| 759 | H | 0 | 2-I | 2-CH$_3$-4-CF(CF$_3$)$_2$ | |
| 760 | H | 0 | 2-I | 2-CH$_3$-4-CF$_2$CF$_3$ | |
| 761 | H | 0 | 2-I | 2-Cl-4-CF(CF$_3$)$_2$ | |
| 762 | H | 0 | 5-I | 2-CH$_3$-4-CF(CF$_3$)$_2$ | |
| 763 | H | 0 | 5-I | 2-CH$_3$-4-CF$_2$CF$_3$ | |

TABLE 9

($R^2$ = $R^3$ = H, $Z^1$ = $Z^2$ = O, Het = Q3, p = 0, $B^1$ = $B^2$ = $B^3$ = $B^4$ = C)

| No | $R^1$ | Xn | Ym | Physical property m.p. ° C. |
|---|---|---|---|---|
| 764 | CH(CH$_3$)CH$_2$SC$_2$H$_5$ | H | 2-CH$_3$-4-OCF$_3$ | |
| 765 | CH(CH$_3$)CH$_2$SC$_2$H$_5$ | H | 2-CH$_3$-4-CF$_2$CF$_3$ | |
| 766 | CH(CH$_3$)CH$_2$SC$_2$H$_5$ | H | 2-CH$_3$-4-CF$_2$CF$_2$CF$_3$ | |
| 767 | CH(CH$_3$)CH$_2$SC$_2$H$_5$ | H | 2-CH$_3$-4-CF(CF$_3$)$_2$ | |
| 768 | CH(CH$_3$)CH$_2$SC$_2$H$_5$ | 2-Cl | 2-CH$_3$-4-(CF$_2$)$_3$CF$_3$ | |
| 769 | CH(CH$_3$)CH$_2$SC$_2$H$_5$ | 2-I | 2-Cl-4-CF(CF$_3$)$_2$ | |
| 770 | C(CH$_3$)$_2$CH$_2$SC$_2$H$_5$ | H | 2-CH$_3$-4-OCF$_3$ | |
| 771 | C(CH$_3$)$_2$CH$_2$SC$_2$H$_5$ | H | 2-CH$_3$-4-CF$_2$CF$_3$ | |
| 772 | C(CH$_3$)$_2$CH$_2$SC$_2$H$_5$ | H | 2-CH$_3$-4-CF$_2$CF$_2$CF$_3$ | |
| 773 | C(CH$_3$)$_2$CH$_2$SC$_2$H$_5$ | 5-Cl | 2-CH$_3$-4-CF(CF$_3$)$_2$ | |
| 774 | C(CH$_3$)$_2$CH$_2$SC$_2$H$_5$ | 5-Br | 2-CH$_3$-4-(CF$_2$)$_3$CF$_3$ | |
| 775 | C(CH$_3$)$_2$CH$_2$SC$_2$H$_5$ | 5-I | 2-Cl-4-CF(CF$_3$)$_2$ | |
| 776 | CH(CH$_3$)CH$_2$NHAc | 2-Cl | 2-CH$_3$-4-OCF$_3$ | |
| 777 | CH(CH$_3$)CH$_2$NHAc | 5-Cl | 2-CH$_3$-4-CF$_2$CF$_3$ | |
| 778 | CH(CH$_3$)CH$_2$NHAc | 5-I | 2-CH$_3$-4-CF$_2$CF$_2$CF$_3$ | |
| 779 | CH(CH$_3$)CH$_2$NHAc | 2-I | 2-CH$_3$-4-CF(CF$_3$)$_2$ | |
| 780 | C(CH$_3$)$_2$CH$_2$NHAc | 2-Cl | 2-CH$_3$-4-(CF$_2$)$_3$CF$_3$ | |
| 781 | C(CH$_3$)$_2$CH$_2$NHAc | 5-I | 2-Cl-4-CF(CF$_3$)$_2$ | |
| 782 | CH(CH$_3$)C$_2$H$_4$OCH$_3$ | 2-Cl | 2-CH$_3$-4-CF(CF$_3$)$_2$ | |
| 783 | CH(CH$_3$)C$_2$H$_4$OCH$_3$ | 2-I | 2-CH$_3$-4-CF(CH$_3$)$_2$ | |
| 784 | C(CH$_3$)$_2$C$_2$H$_4$OCH$_3$ | 5-I | 2-CH$_3$-4-CF(CF$_3$)$_2$ | |

TABLE 10

($Z^1$ = $Z^2$ = O, $R^3$ = H, Het = Q4, $B^1$ = $B^2$ = $B^3$ = $B^4$ = C)

| No | $R^1$ | $R^2$ | p | Xn | Ym | Physical property m.p. ° C. |
|---|---|---|---|---|---|---|
| 785 | i-C$_3$H$_7$ | H | 0 | H | 2-CH$_3$-4-CF$_3$ | 184–185 |
| 786 | i-C$_3$H$_7$ | H | 0 | H | 2-CH$_3$-4-OCHF$_2$ | |
| 787 | i-C$_3$H$_7$ | H | 0 | H | 2-CH$_3$-4-OCF$_3$ | |
| 788 | i-C$_3$H$_7$ | H | 0 | H | 2-CH$_3$-4-OCBrF$_2$ | |
| 789 | i-C$_3$H$_7$ | H | 0 | H | 2-CH$_3$-4-OCF$_2$CHF$_2$ | |
| 790 | i-C$_3$H$_7$ | H | 0 | H | 2-CH$_3$-3-OCF$_2$CHClF | |
| 791 | i-C$_3$H$_7$ | H | 0 | H | 2-CH$_3$-4-OCF$_2$CCl$_2$F | |
| 792 | i-C$_3$H$_7$ | H | 0 | H | 2-CH$_3$-4-OCF$_2$CBrF$_2$ | |
| 793 | i-C$_3$H$_7$ | H | 0 | H | 2-CH$_3$-4-OCH$_2$CF$_2$CHF$_2$ | |
| 794 | i-C$_3$H$_7$ | H | 0 | H | 2-CH$_3$-4-CF$_2$CF$_3$ | paste |
| 795 | i-C$_3$H$_7$ | H | 0 | H | 2-CH$_3$-4-CF(CF$_3$)$_2$ | 159–161 |
| 796 | i-C$_3$H$_7$ | H | 0 | H | 2-CH$_3$-4-SCF$_2$CBrF$_2$ | |
| 797 | i-C$_3$H$_7$ | H | 0 | H | 2-CH$_3$-4-SCH$_2$CF$_2$CHF$_2$ | |
| 798 | i-C$_3$H$_7$ | H | 0 | H | 2-CH$_3$-4-SO$_2$CH$_2$CF$_2$CHF$_2$ | |

TABLE 10-continued ($Z^1 = Z^2 = O, R^3 = H, Het = Q4, B^1 = B^2 = B^3 = B^4 = C$)

| No | $R^1$ | $R^2$ | p | Xn | Ym | Physical property m.p. ° C. |
|---|---|---|---|---|---|---|
| 799 | i-$C_3H_7$ | H | 0 | H | 2-Cl-4-$CF_3$ | |
| 800 | i-$C_3H_7$ | H | 0 | H | 2-Cl-4-CF($CF_2$)$_2$ | |
| 801 | i-$C_3H_7$ | H | 0 | H | 3-Cl-4-$OCHF_2$ | |
| 802 | i-$C_3H_7$ | H | 0 | H | 3-F-4-$OCHF_2$ | |
| 803 | i-$C_3H_7$ | H | 1 | H | 2-$CH_3$-4-$CF_2CF_3$ | |
| 804 | i-$C_3H_7$ | H | 1 | H | 2-$CH_3$-4-CF($CF_3$)$_2$ | 108–110 |
| 805 | $C_2H_5$ | $C_2H_5$ | 0 | H | 2-$CH_3$-4-$CF_2CF_3$ | 130–132 |
| 806 | n-$C_3H_7$ | H | 0 | 4-Cl | 2-$CH_3$-4-$CF_2CF_3$ | |
| 807 | c-$C_3H_5$ | H | 0 | 4-Cl | 2-$CH_3$-4-CF($CF_3$)$_2$ | |
| 808 | n-$C_3H_7$ | H | 0 | 4-Cl | 2-$CH_3$-4-$OCF_2CBrFCF_3$ | |
| 809 | i-$C_4H_9$ | H | 0 | 4-Cl | 2-$CH_3$-4-$OCF_2CHFOCF_3$ | |
| 810 | i-$C_4H_9$ | H | 0 | 4-Cl | 2-$CH_3$-4-$OCHF_2$-5-Cl | |
| 811 | n-$C_4H_9$ | H | 0 | 4-Cl | 2-$CH_3$-4-$OCF_2CHF_2$-5-Cl | |
| 812 | i-$C_3H_7$ | H | 0 | 4-Cl | 2-$CH_3$-4-$SCHF_2$ | |
| 813 | i-$C_3H_7$ | H | 0 | 4-Cl | 2-$CH_3$-4-($F_5$—PhO) | |
| 814 | i-$C_3H_7$ | H | 0 | 4-Cl | 2-$CH_3$-4-(5-$CF_3$-2-Pyr—O) | |
| 815 | i-$C_3H_7$ | H | 0 | 4-Cl | 2-$CH_3$-4-(3-Cl-5-$CF_3$-2-Pyr—O) | |
| 816 | i-$C_3H_7$ | H | 0 | 4-Cl | 2-$CH_3$-4-P=O(O$C_2H_5$)$_2$ | |
| 817 | i-$C_3H_7$ | H | 0 | 4-Cl | 2-$CH_3$-4-OP=S(O$CH_3$)$_2$ | |
| 818 | i-$C_3H_7$ | H | 0 | 4-Cl | 2-$CF_3$-4-$OCHF_2$ | |
| 819 | i-$C_3H_7$ | H | 0 | 4-Cl | 3-$CF_3$-4-$OCHF_2$ | |
| 820 | i-$C_3H_7$ | H | 0 | 4-Cl | 3-N=C($CF_3$)—O-4 | |
| 821 | i-$C_3H_7$ | H | 0 | 4-Cl | 2-$CH_3$-4-$CF_2CF_3$ | 149–152 |
| 822 | i-$C_3H_7$ | H | 0 | 4-Cl | 2-$CH_3$-4-CF($CF_3$)$_2$ | |
| 823 | c-$C_3H_5$ | H | 0 | 4-Cl | 2-$CH_3$-4-$OCHF_2$ | |
| 824 | i-$C_3H_7$ | H | 0 | 4-Cl | 2-$CH_3$-4-$CF_3$ | |
| 825 | i-$C_3H_7$ | H | 0 | 4-Cl | 2-$CH_3$-4-$OCHF_2$ | |
| 826 | i-$C_3H_7$ | H | 0 | 4-Cl | 2-$CH_3$-4-$OCF_3$ | |
| 827 | i-$C_3H_7$ | H | 0 | 4-Cl | 2-$CH_3$-4-$OCBrF_2$ | |
| 828 | i-$C_3H_7$ | H | 0 | 4-Cl | 2-$CH_3$-4-$OCF_2CHF_2$ | |
| 829 | i-$C_3H_7$ | H | 0 | 4-Cl | 2-$CH_3$-3-$OCF_2CHClF$ | |
| 830 | i-$C_3H_7$ | H | 0 | 4-Cl | 2-$CH_3$-4-$OCF_2CCl_2F$ | |
| 831 | i-$C_3H_7$ | H | 0 | 4-Cl | 2-$CH_3$-4-$OCF_2CBrF_2$ | |
| 832 | i-$C_3H_7$ | H | 0 | 4-Br | 2-$CH_3$-4-$OCH_2CF_2CHF_2$ | |
| 833 | i-$C_3H_7$ | H | 0 | 4-Br | 2-$CH_3$-4-$CF_2CF_3$ | |
| 834 | i-$C_3H_7$ | H | 0 | 4-Br | 2-$CH_3$-4-CF($CF_3$)$_2$ | |
| 835 | i-$C_3H_7$ | H | 0 | 4-Br | 2-$CH_3$-4-$SCF_2CBrF_2$ | |
| 836 | i-$C_3H_7$ | H | 0 | 4-Br | 2-$CH_3$-4-$SCH_2CF_2CHF_2$ | |
| 837 | i-$C_3H_7$ | H | 0 | 4-Br | 2-$CH_3$-4-$SO_2CH_2CF_2CHF_2$ | |
| 838 | i-$C_3H_7$ | H | 0 | 4-Br | 2-Cl-4-$CF_3$ | |
| 839 | i-$C_3H_7$ | H | 0 | 4-Br | 2-Cl-4-CF($CF_2$)$_2$ | |
| 840 | i-$C_3H_7$ | H | 0 | 4-Br | 3-Cl-4-$OCHF_2$ | |
| 841 | i-$C_3H_7$ | H | 0 | 4-Br | 3-F-4-$OCHF_2$ | |
| 842 | i-$C_3H_7$ | H | 0 | 4-Br | 2-Cl-4-$OCF_3$ | |
| 843 | i-$C_3H_7$ | H | 0 | 4-Br | 2-Br-4-$OCF_3$ | |
| 844 | i-$C_3H_7$ | H | 0 | 4-Br | 3,5-$Cl_2$-4-$OCHF_2$ | |
| 845 | i-$C_3H_7$ | H | 0 | 4-I | 2-$CH_3$-4-CF($CF_3$)$_2$ | |
| 846 | i-$C_3H_7$ | H | 0 | 4-I | 2-$CH_3$-4-($CF_2$)$_3CF_3$ | |
| 847 | i-$C_3H_7$ | H | 0 | 4-I | 2-$CH_3$-4-$OCH_3$ | |
| 848 | i-$C_3H_7$ | H | 0 | 4-I | 2-$CH_3$-4-$OCH_2CF_2CHF_2$ | |
| 849 | i-$C_3H_7$ | H | 0 | 4-I | 2,4-($CH_3$)$_2$-3-$OCHF_2$ | |
| 850 | i-$C_3H_7$ | H | 0 | 4-I | 2,3-($CH_3$)$_2$-4-$OCH_3$ | |
| 851 | i-$C_3H_7$ | H | 0 | 4-I | 2-Cl-4-$OCF_3$ | |
| 852 | i-$C_3H_7$ | H | 0 | 4-I | 2-Br-4-$OCF_3$ | |
| 853 | i-$C_3H_7$ | H | 0 | 4-I | 2-$CH_3$-4-$OCHF_2$ | |
| 854 | i-$C_3H_7$ | H | 0 | 4-I | 2-$CH_3$-4-$OCF_3$ | |
| 855 | i-$C_3H_7$ | H | 0 | 4-I | 2-$CH_3$-4-$OCBrF_2$ | |
| 856 | i-$C_3H_7$ | H | 0 | 4-I | 2-$CH_3$-4-$OCF_2CHFCF_3$ | |
| 857 | i-$C_3H_7$ | H | 0 | 4-I | 2-$CH_3$-4-$OCF_2CHClF$ | |
| 858 | i-$C_3H_7$ | H | 0 | 4-I | 2-$CH_3$-4-$OCF_2CHF_2$ | |
| 859 | i-$C_3H_7$ | H | 0 | 4-I | 2-$CH_3$-3-Cl-4-$OCHF_2$ | |
| 860 | i-$C_3H_7$ | H | 0 | 4-I | 2,3-($CH_3$)$_2$-4-$OCHF_2$ | |
| 861 | i-$C_3H_7$ | H | 0 | 4-I | 2-$CH_3$-4-$SCH_3$ | |
| 862 | i-$C_3H_7$ | H | 0 | 4-I | 2-$CH_3$-4-(3-$CF_3$—PhO) | |
| 863 | i-$C_3H_7$ | H | 0 | 4-I | 2-$CH_3$-4-(3-Cl-5-$CF_3$-2-Pyr—O) | |
| 864 | i-$C_3H_7$ | H | 0 | 5-Cl | 2-Cl-4-$CF_3$ | |
| 865 | i-$C_3H_7$ | H | 0 | 5-Cl | 2-$CH_3$-4-$CF_3$ | |
| 866 | i-$C_3H_7$ | H | 0 | 5-Cl | 2-$CH_3$-4-CF($CF_3$)$_2$ | |
| 867 | i-$C_3H_7$ | H | 0 | 5-Cl | 2-$CH_3$-4-($CF_2$)$_3CF_3$ | |
| 868 | i-$C_3H_7$ | H | 0 | 5-Cl | 2-$CH_3$-4-$OCH_2CF_2CHF_2$ | |
| 869 | i-$C_3H_7$ | H | 0 | 5-Cl | 2,4-($CH_3$)$_2$-3-$OCHF_2$ | |
| 870 | i-$C_3H_7$ | H | 0 | 5-Cl | 2,3-($CH_3$)$_2$-4-$OCH_3$ | |
| 871 | i-$C_3H_7$ | H | 0 | 5-Cl | 2-$CH_3$-4-$OCH_3$ | |

TABLE 10-continued ($Z^1$ = $Z^2$ = O, $R^3$ = H, Het = Q4, $B^1$ = $B^2$ = $B^3$ = $B^4$ = C)

| No | $R^1$ | $R^2$ | p | Xn | Ym | Physical property m.p. ° C. |
|---|---|---|---|---|---|---|
| 872 | i-$C_3H_7$ | H | 0 | 5-Cl | 2-Cl-4-$OCF_3$ | |
| 873 | i-$C_3H_7$ | H | 0 | 5-Cl | 2-Br-4-$OCF_3$ | |
| 874 | i-$C_3H_7$ | H | 0 | 5-Cl | 2-$CH_3$-4-$OCHF_2$ | |
| 875 | i-$C_3H_7$ | H | 0 | 5-Cl | 2-$CH_3$-4-$OCF_3$ | |
| 876 | i-$C_3H_7$ | H | 0 | 5-Cl | 2-$CH_3$-4-$OCBrF_2$ | |
| 877 | i-$C_3H_7$ | H | 0 | 5-Cl | 2-$CH_3$-4-$OCF_2CHFCF_3$ | |
| 878 | i-$C_3H_7$ | H | 0 | 5-Cl | 2-$CH_3$-4-$OCF_2CHClF$ | |
| 879 | i-$C_3H_7$ | H | 0 | 5-Cl | 2-$CH_3$-4-$OCF_2CHF_2$ | |
| 880 | i-$C_3H_7$ | H | 0 | 6-Cl | 2-$CH_3$-4-$CF(CF_3)_2$ | |
| 881 | i-$C_3H_7$ | H | 0 | 6-Cl | 2-$CH_3$-4-$(CF_2)_3CF_3$ | |
| 882 | i-$C_3H_7$ | H | 1 | 6-Cl | 2-$CH_3$-4-$CF(CF_3)_2$ | |
| 883 | i-$C_3H_7$ | H | 1 | 6-Cl | 2-$CH_3$-4-$(CF_2)_3CF_3$ | |
| 884 | i-$C_3H_7$ | H | 0 | 6-Cl | 2-$CH_3$-4-$OCH_2CF_2CHF_2$ | |
| 885 | i-$C_3H_7$ | H | 0 | 4-I | 2-$CH_3$-4-$OCH_2CF_2CHF_2$ | |
| 886 | i-$C_3H_7$ | H | 0 | 4-I | 2-$CH_3$-4-$CF(CF_3)_2F_2$ | |
| 887 | i-$C_3H_7$ | H | 0 | 4-I | 2-$CH_3$-4-$(CF_2)_3CF_3$ | |
| 888 | i-$C_3H_7$ | H | 0 | 4-I | 2-$CH_3$-4-$CF(CF_3)_2$ | |
| 889 | i-$C_3H_7$ | H | 0 | 4-I | 2-$CH_3$-4-$(CF_2)_3CF$ | |
| 890 | i-$C_3H_7$ | H | 0 | 4-I | 2-Br-4-$OCF_3$ | |
| 891 | i-$C_3H_7$ | H | 0 | 4-I | 2-$CH_3$-4-$OCHF_2$ | |
| 892 | i-$C_3H_7$ | H | 0 | 4-I | 2-$CH_3$-4-$OCF_3$ | |
| 893 | i-$C_3H_7$ | H | 0 | 4-I | 2-$CH_3$-4-$OCBrF_2$ | |
| 894 | i-$C_3H_7$ | H | 0 | 4-I | 2-$CH_3$-4-$OCF_2CHFCF_3$ | |
| 895 | i-$C_3H_7$ | H | 0 | 4-I | 2-$CH_3$-4-$OCF_2CHClF$ | |
| 896 | i-$C_3H_7$ | H | 0 | 5-I | 2-$CH_3$-4-$CF_2CF_3$ | |
| 897 | i-$C_3H_7$ | H | 0 | 5-I | 2-$CH_3$-4-$CF_2CF_2CF_3$ | |
| 898 | i-$C_3H_7$ | H | 0 | 5-I | 2-$CH_3$-4-$CF(CF_3)_2$ | |
| 899 | i-$C_3H_7$ | H | 0 | 5-I | 2-$CH_3$-4-$SCH_3$ | |
| 900 | i-$C_3H_7$ | H | 0 | 5-I | 2-$CH_3$-4-(3-$CF_3$—PhO) | |
| 901 | i-$C_3H_7$ | H | 0 | 5-I | 2-$CH_3$-4-(5-$CF_3$-2-Pyr—O) | |
| 902 | i-$C_3H_7$ | H | 0 | 5-I | 2-$CH_3$-4-(3-Cl-5-$CF_3$-2-Pyr—O) | |
| 903 | i-$C_3H_7$ | H | 0 | 6-I | 2-$CH_3$-4-$CF(CF_3)_2$ | |
| 904 | i-$C_3H_7$ | H | 0 | 6-I | 2-Cl-4-$CF_2CF_3$ | |
| 905 | i-$C_3H_7$ | H | 0 | 4-Br | 2-Cl-4-$CF_3$ | |
| 906 | i-$C_3H_7$ | H | 0 | 4-Br | 2-Cl-4-$CF_2CF_3$ | |
| 907 | i-$C_3H_7$ | H | 0 | 4-Br | 2-Cl-4-$CF_2CF_2CF_3$ | |
| 908 | i-$C_3H_7$ | H | 0 | 4-Br | 2-Cl-4-$CF(CF_3)_2$ | |
| 909 | i-$C_3H_7$ | H | 0 | 4-Br | 2-Cl-4-$(CF_2)_3CF_3$ | |
| 910 | i-$C_3H_7$ | H | 0 | 4-Br | 2-$C_2H_5$-4-$CF(CF_3)_2$ | |
| 911 | i-$C_3H_7$ | H | 0 | 4-Br | 2-$CH_3$-4-Br | |
| 912 | i-$C_3H_7$ | H | 0 | 4-Br | 2-$CH_3$-4-I | |
| 913 | i-$C_3H_7$ | H | 0 | 4-Br | 2-$CH_3$-4-F | |
| 914 | i-$C_3H_7$ | H | 0 | 4-Br | 2-Cl-4-$CF_3$ | |
| 915 | i-$C_3H_7$ | H | 0 | 4-Br | 2-$CH_3$-4-$CF_3$ | |
| 916 | i-$C_3H_7$ | H | 0 | 4-Br | 2-$CH_3$-4-$CF_3$ | |
| 917 | i-$C_3H_7$ | H | 0 | 4-Br | 2-$CH_3$-4-$CF_2CF_3$ | |
| 918 | i-$C_3H_7$ | H | 0 | 4-Br | 2-$CH_3$-4-$CF_2CF_2CF_3$ | |
| 919 | i-$C_3H_7$ | H | 0 | 4-Br | 2-$CH_3$-4-$CF(CF_3)_2$ | |
| 920 | i-$C_3H_7$ | H | 0 | 4-Br | 2-$CH_3$-4-$(CF_2)_3CF_3$ | |
| 921 | i-$C_3H_7$ | H | 0 | 4-Br | 2-$CH_3$-4-$OCH_3$ | |
| 922 | i-$C_3H_7$ | H | 0 | 4-Br | 2-$CH_3$-4-O—$C_3H_7$-i | |
| 923 | i-$C_3H_7$ | H | 0 | 4-Br | 2,3-$(CH_3)_2$-4-$OCH_3$ | |
| 924 | i-$C_3H_7$ | H | 0 | 4-Br | 2-$CH_3$-4-$OCH_2CF_3$ | |
| 925 | i-$C_3H_7$ | H | 0 | 4-Br | 2-$CH_3$-4-$OCF_2CBrF_2$ | |
| 926 | i-$C_3H_7$ | H | 0 | 5-Br | 2-$CH_3$-4-$OCF_3$ | |
| 927 | i-$C_3H_7$ | H | 0 | 5-Br | 2-$CH_3$-4-$CF_2CF_3$ | |
| 928 | i-$C_3H_7$ | H | 0 | 5-Br | 2-$CH_3$-4-$CF_2CF_2CF_3$ | |
| 929 | i-$C_3H_7$ | H | 0 | 5-Br | 2-$CH_3$-4-$CF(CF_3)_2$ | |
| 930 | i-$C_3H_7$ | H | 0 | 5-Br | 2-$CH_3$-4-$(CF_2)_3CF_3$ | |
| 931 | i-$C_3H_7$ | H | 0 | 5-Br | 2-Cl-4-$CF(CF_3)_2$ | |
| 932 | i-$C_3H_7$ | H | 0 | 5-Br | 2-Cl-4-$(CF_2)_3CF_3$ | |
| 933 | i-$C_3H_7$ | H | 0 | 5-Br | 2-$C_2H_5$-4-$CF(CF_3)_2$ | |
| 934 | i-$C_3H_7$ | H | 0 | 5-Br | 2-F-4-$CF_2CF_3$ | |
| 935 | i-$C_3H_7$ | H | 0 | 6-Br | 2-$CH_3$-4-$OCF_3$ | |
| 936 | i-$C_3H_7$ | H | 0 | 6-Br | 2-$CH_3$-4-$CF_2CF_3$ | |
| 937 | i-$C_3H_7$ | H | 0 | 6-Br | 2-$CH_3$-4-$CF_2CF_2CF_3$ | |
| 938 | i-$C_3H_7$ | H | 0 | 6-Br | 2-$CH_3$-4-$CF(CF_3)_2$ | |
| 939 | i-$C_3H_7$ | H | 0 | 6-Br | 2-$CH_3$-4-$(CF_2)_3CF_3$ | |
| 940 | i-$C_3H_7$ | H | 0 | 6-Br | 2-Cl-4-$CF(CF_3)_2$ | |
| 941 | i-$C_3H_7$ | H | 0 | 6-Br | 2-Cl-4-$(CF_2)_3CF_3$ | |
| 942 | i-$C_3H_7$ | H | 0 | 6-Br | 2-$C_2H_5$-4-$CF(CF_3)_2$ | |
| 943 | i-$C_3H_7$ | H | 0 | 6-Br | 2-F-4-$CF_2CF_3$ | |
| 944 | i-$C_3H_7$ | H | 0 | 6-Br | 2-$C_2H_5$-4-$CF_2CF_3$ | |
| 945 | i-$C_3H_7$ | H | 0 | 4-$CH_3$ | 2-$CH_3$-4-$OCF_3$ | |

TABLE 10-continued ($Z^1 = Z^2 = O$, $R^3 = H$, Het = Q4, $B^1 = B^2 = B^3 = B^4 = C$)

| No | $R^1$ | $R^2$ | p | Xn | Ym | Physical property m.p. °C. |
|---|---|---|---|---|---|---|
| 946 | i-$C_3H_7$ | H | 0 | 4-$CH_3$ | 2-$CH_3$-4-$CF_2CF_3$ | |
| 947 | i-$C_3H_7$ | H | 0 | 4-$CH_3$ | 2-$CH_3$-4-$CF_2CF_2CF_3$ | |
| 948 | i-$C_3H_7$ | H | 0 | 4-$CH_3$ | 2-$CH_3$-4-$CF(CF_3)_2$ | |
| 949 | i-$C_3H_7$ | H | 0 | 4-$CH_3$ | 2-$CH_3$-4-$(CF_2)_3CF_3$ | |
| 950 | i-$C_3H_7$ | H | 0 | 4-$CH_3$ | 2-Cl-4-$CF(CF_3)_2$ | |
| 951 | i-$C_3H_7$ | H | 0 | 4-$CH_3$ | 2-Cl-4-$(CF_2)_3CF_3$ | |
| 952 | i-$C_3H_7$ | H | 0 | 4-$CH_3$ | 2-$C_2H_5$-4-$CF(CF_3)_2$ | |
| 953 | i-$C_3H_7$ | H | 0 | 4-$CH_3$ | 2-F-4-$CF_2CF_3$ | |
| 954 | i-$C_3H_7$ | H | 0 | 4-$CF_3$ | 2-$CH_3$-4-$OCF_3$ | |
| 955 | i-$C_3H_7$ | H | 0 | 4-$CF_3$ | 2-$CH_3$-4-$CF_2CF_3$ | |
| 956 | i-$C_3H_7$ | H | 0 | 4-$CF_3$ | 2-$CH_3$-4-$CF_2CF_2CF_3$ | |
| 957 | i-$C_3H_7$ | H | 0 | 4-$CF_3$ | 2-$CH_3$-4-$CF(CF_3)_2$ | |
| 958 | i-$C_3H_7$ | H | 0 | 4-$CF_3$ | 2-$CH_3$-4-$(CF_2)_3CF_3$ | |
| 959 | i-$C_3H_7$ | H | 0 | 4-$CF_3$ | 2-Cl-4-$CF(CF_3)_2$ | |
| 960 | i-$C_3H_7$ | H | 0 | 4-$CF_3$ | 2-Cl-4-$(CF_2)_3CF_3$ | |
| 961 | i-$C_3H_7$ | H | 0 | 4-$CF_3$ | 2-$C_2H_5$-4-$CF(CF_3)_2$ | |
| 962 | i-$C_3H_7$ | H | 0 | 4-$CF_3$ | 2-F-4-$CF_2CF_3$ | |
| 963 | i-$C_3H_7$ | H | 0 | 4-$CF_3$ | 2-$C_2H_5$-4-$CF_2CF_3$ | |
| 964 | i-$C_3H_7$ | H | 0 | 4-$CF_3$ | 2-Br-4-$CF_2CF_3$ | |
| 965 | i-$C_3H_7$ | H | 0 | 5-$CH_3$ | 2-$CH_3$-4-$OCF_3$ | |
| 966 | i-$C_3H_7$ | H | 0 | 5-$CH_3$ | 2-$CH_3$-4-$CF_2CF_3$ | |
| 967 | i-$C_3H_7$ | H | 0 | 5-$CH_3$ | 2-$CH_3$-4-$CF_2CF_2CF_3$ | |
| 968 | i-$C_3H_7$ | H | 0 | 5-$CH_3$ | 2-$CH_3$-4-$CF(CF_3)_2$ | |
| 969 | i-$C_3H_7$ | H | 0 | 6-$CH_3$ | 2-$CH_3$-4-$(CF_2)_3CF_3$ | |
| 970 | i-$C_3H_7$ | H | 0 | 6-$CH_3$ | 2-Cl-4-$CF(CF_3)_2$ | |
| 971 | i-$C_3H_7$ | H | 0 | 6-$CH_3$ | 2-Cl-4-$(CF_2)_3CF_3$ | |
| 972 | i-$C_3H_7$ | H | 0 | 6-$CH_3$ | 2-$C_2H_5$-4-$CF(CF_3)_2$ | |
| 973 | i-$C_3H_7$ | H | 0 | 6-$CH_3$ | 2-F-4-$CF_2CF_3$ | |
| 974 | i-$C_3H_7$ | H | 0 | 5-$CF_3$ | 2-$CH_3$-4-$OCF_3$ | |
| 975 | i-$C_3H_7$ | H | 0 | 5-$CF_3$ | 2-$CH_3$-4-$CF_2CF_3$ | |
| 976 | i-$C_3H_7$ | H | 0 | 5-$CF_3$ | 2-$CH_3$-4-$CF_2CF_2CF_3$ | |
| 977 | i-$C_3H_7$ | H | 0 | 5-$CF_3$ | 2-$CH_3$-4-$CF(CF_3)_2$ | |
| 978 | i-$C_3H_7$ | H | 0 | 5-$CF_3$ | 2-$CH_3$-4-$(CF_2)_3CF_3$ | |
| 979 | i-$C_3H_7$ | H | 0 | 5-$CF_3$ | 2-Cl-4-$CF(CF_3)_2$ | |
| 980 | i-$C_3H_7$ | H | 0 | 5-$CF_3$ | 2-Cl-4-$(CF_2)_3CF_3$ | |
| 981 | i-$C_3H_7$ | H | 0 | 5-$CF_3$ | 2-$C_2H_5$-4-$CF_2CF_3$ | |
| 982 | i-$C_3H_7$ | H | 0 | 5-$CF_3$ | 2-$C_2H_5$-4-$CF(CF_3)_2$ | |
| 983 | i-$C_3H_7$ | H | 0 | 6-$CF_3$ | 2-F-4-$CF_2CF_3$ | |
| 984 | i-$C_3H_7$ | H | 0 | 6-$CF_3$ | 2-Br-4-$CF_2CF_3$ | |
| 985 | i-$C_3H_7$ | H | 0 | 6-$CF_3$ | 2-Br-4-$CF(CF_3)_2$ | |

TABLE 11

($R^1 = CH(CH_3)CH_2SCH_3$, $R^3 = H$, $Z^1 = Z^2 = O$, Het = Q4, $B^1 = B^2 = B^3 = B^4 = C$)

| No | $R^2$ | p | Xn | Ym | Physical property m.p. °C. |
|---|---|---|---|---|---|
| 986 | H | 0 | H | 2-$CH_3$-4-$OCF_3$ | |
| 987 | H | 0 | H | 2-$CH_3$-4-$CF_2CF_3$ | |
| 988 | H | 0 | H | 2-$CH_3$-4-$CF_2CF_2CF_3$ | |
| 989 | H | 0 | H | 2-$CH_3$-4-$CF(CF_3)_2$ | 108–110 |
| 990 | H | 1 | H | 2-$CH_3$-4-$CF(CF_3)_2$ | paste |
| 991 | H | 0 | H | 2-Cl-4-$CF(CF_3)_2$ | |
| 992 | H | 0 | H | 2-Cl-4-$(CF_2)_3CF_3$ | |
| 993 | H | 0 | H | 2-$C_2H_5$-4-$CF_2CF_3$ | |
| 994 | H | 0 | H | 2-$C_2H_5$-4-$CF(CF_3)_2$ | |
| 995 | H | 0 | H | 2-F-4-$CF_2CF_3$ | |
| 996 | H | 0 | H | 2-Br-4-$CF_2CF_3$ | |
| 997 | H | 0 | H | 2-Br-4-$CF(CF_3)_2$ | |
| 998 | H | 0 | 4-Cl | 2-$CH_3$-4-$CF_2CF_3$ | |
| 999 | H | 0 | 4-Cl | 2-$CH_3$-4-$CF(CF_3)_2$ | 237–239 |
| 1000 | H | 0 | 5-Cl | 2-$CH_3$-4-$CF(CF_3)_2$ | |
| 1001 | H | 0 | 4-I | 2-$CH_3$-4-$CF(CF_3)_2$ | |
| 1002 | H | 0 | 4-I | 2-$CH_3$-4-$CF_2CF_3$ | |
| 1003 | H | 0 | 4-I | 2-Cl-4-$CF(CF_3)_2$ | |

TABLE 11-continued ($R^1 = CH(CH_3)CH_2SCH_3$, $R^3 = H$, $Z^1 = Z^2 = O$, Het = Q4, $B^1 = B^2 = B^3 = B^4 = C$)

| No | $R^2$ | p | Xn | Ym | Physical property m.p. °C. |
|---|---|---|---|---|---|
| 1004 | H | 0 | 5-I | 2-$CH_3$-4-$CF(CF_3)_2$ | |
| 1005 | H | 0 | 5-I | 2-$CH_3$-4-$CF_2CF_3$ | |

TABLE 12

($R^1 = C(CH_3)_2CH_2SCH_3$, $R^3 = H$, $Z^1 = Z^2 = O$, Het = Q4, $B^1 = B^2 = B^3 = B^4 = C$)

| No | $R^2$ | p | Xn | Ym | Physical property m.p. °C. |
|---|---|---|---|---|---|
| 1006 | H | 0 | H | 2-$CH_3$-4-$OCF_3$ | |
| 1007 | H | 0 | H | 2-$CH_3$-4-$CF_2CF_3$ | |
| 1008 | H | 0 | H | 2-$CH_3$-4-$CF_2CF_2CF_3$ | |
| 1009 | H | 0 | H | 2-$CH_3$-4-$CF(CF_3)_2$ | paste |

TABLE 12-continued ($R^1$ = C(CH$_3$)$_2$CH$_2$SCH$_3$, $R^3$ = H, $Z^1$ = $Z^2$ = O, Het = Q4, $B^1$ = $B^2$ = $B^3$ = $B^4$ = C)

| No | $R^2$ | p | Xn | Ym | Physical property m.p. ° C. |
|---|---|---|---|---|---|
| 1010 | H | 0 | H | 2-CH$_3$-4-(CF$_2$)$_3$CF$_3$ | |
| 1011 | H | 0 | H | 2-Cl-4-CF(CF$_3$)$_2$ | |
| 1012 | H | 0 | H | 2-Cl-4-(CF$_2$)$_3$CF$_3$ | |
| 1013 | H | 0 | H | 2-C$_2$H$_5$-4-CF$_2$CF$_3$ | |
| 1014 | H | 0 | H | 2-C$_2$H$_5$-4-CF(CF$_3$)$_2$ | |
| 1015 | H | 0 | H | 2-F-4-CF$_2$CF$_3$ | |
| 1016 | H | 0 | H | 2-Br-4-CF$_2$CF$_3$ | |
| 1017 | H | 0 | H | 2-Br-4-CF(CF$_3$)$_2$ | |
| 1018 | H | 0 | 4-Cl | 2-CH$_3$-4-CF$_2$CF$_3$ | |
| 1019 | H | 0 | 4-Cl | 2-CH$_3$-4-CF(CF$_3$)$_2$ | |
| 1020 | H | 0 | 5-Cl | 2-CH$_3$-4-CF(CF$_3$)$_2$ | |
| 1021 | H | 0 | 4-I | 2-CH$_3$-4-CF(CF$_3$)$_2$ | |
| 1022 | H | 0 | 4-I | 2-CH$_3$-4-CF$_2$CF$_3$ | |
| 1023 | H | 0 | 4-I | 2-Cl-4-CF(CF$_3$)$_2$ | |
| 1024 | H | 0 | 5-I | 2-CH$_3$-4-CF(CF$_3$)$_2$ | |
| 1025 | H | 0 | 5-I | 2-CH$_3$-4-CF$_2$CF$_3$ | |

TABLE 13

($R^2$ = $R^3$ = H, $Z^1$ = $Z^2$ = O, Het = Q4, p = 0, $B^1$ = $B^2$ = $B^3$ = $B^4$ = C)

| No | $R^1$ | Xn | Ym | Physical property m.p. ° C. |
|---|---|---|---|---|
| 1026 | CH(CH$_3$)CH$_2$SC$_2$H$_5$ | H | 2-CH$_3$-4-OCF$_3$ | |
| 1027 | CH(CH$_3$)CH$_2$SC$_2$H$_5$ | H | 2-CH$_3$-4-CF$_2$CF$_3$ | |
| 1028 | CH(CH$_3$)CH$_2$SC$_2$H$_5$ | H | 2-CH$_3$-4-CF$_2$CF$_2$CF$_3$ | |
| 1029 | CH(CH$_3$)CH$_2$SC$_2$H$_5$ | H | 2-CH$_3$-4-CF(CF$_3$)$_2$ | |
| 1030 | CH(CH$_3$)CH$_2$SC$_2$H$_5$ | 4-Cl | 2-CH$_3$-4-(CF$_2$)$_3$CF$_3$ | |
| 1031 | CH(CH$_3$)CH$_2$SC$_2$H$_5$ | 4-I | 2-Cl-4-CF(CF$_3$)$_2$ | |
| 1032 | C(CH$_3$)$_2$CH$_2$SC$_2$H$_5$ | H | 2-CH$_3$-4-OCF$_3$ | |
| 1033 | C(CH$_3$)$_2$CH$_2$SC$_2$H$_5$ | H | 2-CH$_3$-4-CF$_2$CF$_3$ | |
| 1034 | C(CH$_3$)$_2$CH$_2$SC$_2$H$_5$ | H | 2-CH$_3$-4-CF$_2$CF$_2$CF$_3$ | |
| 1035 | C(CH$_3$)$_2$CH$_2$SC$_2$H$_5$ | 5-Cl | 2-CH$_3$-4-CF(CF$_3$)$_2$ | |

TABLE 13-continued ($R^2$ = $R^3$ = H, $Z^1$ = $Z^2$ = O, Het = Q4, p = 0, $B^1$ = $B^2$ = $B^3$ = $B^4$ = C)

| No | $R^1$ | Xn | Ym | Physical property m.p. ° C. |
|---|---|---|---|---|
| 1036 | C(CH$_3$)$_2$CH$_2$SC$_2$H$_5$ | 5-Br | 2-CH$_3$-4-(CF$_2$)$_3$CF$_3$ | |
| 1037 | C(CH$_3$)$_2$CH$_2$SC$_2$H$_5$ | 5-I | 2-Cl-4-CF(CF$_3$)$_2$ | |
| 1038 | CH(CH$_3$)CH$_2$NHAc | 4-Cl | 2-CH$_3$-4-OCF$_3$ | |
| 1039 | CH(CH$_3$)CH$_2$NHAc | 5-Cl | 2-CH$_3$-4-CF$_2$CF$_3$ | |
| 1040 | CH(CH$_3$)CH$_2$NHAc | 5-I | 2-CH$_3$-4-CF$_2$CF$_2$CF$_3$ | |
| 1041 | CH(CH$_3$)CH$_2$NHAc | 4-I | 2-CH$_3$-4-CF(CF$_3$)$_2$ | |
| 1042 | C(CH$_3$)$_2$CH$_2$NHAc | 4-Cl | 2-CH$_3$-4-(CF$_2$)$_3$CF$_3$ | |
| 1043 | C(CH$_3$)$_2$CH$_2$NHAc | 5-I | 2-Cl-4-CF(CF$_3$)$_2$ | |
| 1044 | CH(CH$_3$)C$_2$H$_4$OCH$_3$ | 4-Cl | 2-CH$_3$-4-CF$_2$CF$_3$ | |
| 1045 | CH(CH$_3$)C$_2$H$_4$OCH$_3$ | 4-I | 2-CH$_3$-4-CF(CH$_3$)$_2$ | |
| 1046 | C(CH$_3$)$_2$C$_2$H$_4$OCH$_3$ | 5-I | 2-CH$_3$-4-CF(CF$_3$)$_2$ | |

TABLE 14

($Z^1$ = $Z^2$ = O, Het = Q4, $B^1$ = $B^2$ = $B^3$ = $B^4$ = C)

| No | $R^1$ | $R^2$ | $R^3$ | Xn | Ym | Physical property m.p. ° C. |
|---|---|---|---|---|---|---|
| 1047 | C$_2$H$_5$ | C$_2$H$_5$ | CH$_3$ | H | 2-CH$_3$-4-OCF$_3$ | |
| 1048 | C$_2$H$_5$ | C$_2$H$_5$ | CH$_3$ | 4-Cl | 2-CH$_3$-4-CF$_2$CF$_3$ | paste |
| 1049 | C$_2$H$_5$ | C$_2$H$_5$ | CH$_3$ | 4-Cl | 2-CH$_3$-4-CF$_2$CF$_2$CF$_3$ | |
| 1050 | C$_2$H$_5$ | C$_2$H$_5$ | CH$_3$ | 4-Cl | 2-CH$_3$-4-CF(CF$_3$)$_2$ | |
| 1051 | C$_2$H$_5$ | C$_2$H$_5$ | CH$_3$ | 4-I | 2-CH$_3$-4-(CF$_2$)$_3$CF$_3$ | |
| 1052 | C$_2$H$_5$ | C$_2$H$_5$ | CH$_3$ | 4-I | 2-Cl-4-CF(CF$_3$)$_2$ | |
| 1053 | C$_2$H$_5$ | C$_2$H$_5$ | C$_2$H$_5$ | 4-I | 2-CH$_3$-4-OCF$_3$ | |
| 1054 | C$_2$H$_5$ | C$_2$H$_5$ | C$_2$H$_5$ | 4-Cl | 2-CH$_3$-4-CF$_2$CF$_3$ | |
| 1055 | C$_2$H$_5$ | C$_2$H$_5$ | C$_2$H$_5$ | 4-Cl | 2-CH$_3$-4-CF$_2$CF$_2$CF$_3$ | |
| 1056 | C$_2$H$_5$ | C$_2$H$_5$ | C$_2$H$_5$ | 4-I | 2-CH$_3$-4-CF(CF$_3$)$_2$ | |
| 1057 | C$_2$H$_5$ | C$_2$H$_5$ | C$_2$H$_5$ | 4-I | 2-CH$_3$-4-(CF$_2$)$_3$CF$_3$ | |
| 1058 | C$_2$H$_5$ | C$_2$H$_5$ | C$_2$H$_5$ | 4-I | 2-Cl-4-CF(CF$_3$)$_2$ | |

TABLE 15

($Z^1$ = $Z^2$ = O, $R^2$ = $R^3$ = H, q = 0, Het = Q5, $B^1$ = $B^2$ = $B^3$ = $B^4$ = C)

| No | $R^1$ | p | Xn | Ym | Physical property m.p. ° C. |
|---|---|---|---|---|---|
| 1059 | i-C$_3$H$_7$ | 0 | H | 2-CH$_3$-4-CF$_3$ | |
| 1060 | i-C$_3$H$_7$ | 0 | H | 2-CH$_3$-4-OCF$_3$ | |
| 1061 | i-C$_3$H$_7$ | 0 | H | 2-CH$_3$-4-OCF$_2$CHF$_2$ | |
| 1062 | i-C$_3$H$_7$ | 0 | H | 2-CH$_3$-4-CH$_2$CF$_2$CHF$_2$ | |
| 1063 | i-C$_3$H$_7$ | 0 | H | 2-CH$_3$-4-CF$_2$CF$_3$ | |
| 1064 | i-C$_3$H$_7$ | 0 | H | 2-CH$_3$-4-CF(CF$_3$)$_2$ | |
| 1065 | i-C$_3$H$_7$ | 0 | H | 2-CH$_3$-4-SCH$_2$CF$_2$CHF$_2$ | |
| 1066 | i-C$_3$H$_7$ | 0 | H | 2-CH$_3$-4-SO$_2$CH$_2$CF$_2$CHF$_2$ | |
| 1067 | i-C$_3$H$_7$ | 0 | H | 2-Cl-4-CF(CF$_3$)$_2$ | |
| 1068 | i-C$_3$H$_7$ | 0 | H | 2-Cl-4-CF$_2$CF$_3$ | |
| 1069 | i-C$_3$H$_7$ | 0 | H | 2-C$_2$H$_5$-4-CF(CF$_3$)$_2$ | |
| 1070 | i-C$_3$H$_7$ | 0 | H | 2-F-4-CF$_2$CF$_3$ | |
| 1071 | i-C$_3$H$_7$ | 0 | 5-Cl | 2-CH$_3$-4-CF$_2$CF$_3$ | |
| 1072 | i-C$_3$H$_7$ | 0 | 5-Cl | 2-CH$_3$-4-CF(CF$_3$)$_2$ | |
| 1073 | i-C$_3$H$_7$ | 0 | 5-I | 2-CH$_3$-4-CF$_2$CF$_3$ | |
| 1074 | i-C$_3$H$_7$ | 0 | 5-I | 2-CH$_3$-4-CF(CF$_3$)$_2$ | |
| 1075 | i-C$_3$H$_7$ | 0 | 5-CH$_3$ | 2-CH$_3$-4-CF$_2$CF$_3$ | |
| 1076 | i-C$_3$H$_7$ | 0 | 5-CH$_3$ | 2-CH$_3$-4-CF(CF$_3$)$_2$ | |
| 1077 | i-C$_3$H$_7$ | 0 | 5-CF$_3$ | 2-CH$_3$-4-CF(CF$_3$)$_2$ | |
| 1078 | CH(CH$_3$)CH$_2$SCH$_3$ | 0 | H | 2-CH$_3$-4-CF$_2$CF$_3$ | |
| 1079 | CH(CH$_3$)CH$_2$SCH$_3$ | 0 | H | 2-CH$_3$-4-CF(CF$_3$)$_2$ | |

TABLE 15-continued ($Z^1 = Z^2 = O$, $R^2 = R^3 = H$, q = 0, Het = Q5, $B^1 = B^2 = B^3 = B^4 = C$)

| No | $R^1$ | p | Xn | Ym | Physical property m.p. ° C. |
|---|---|---|---|---|---|
| 1080 | $CH(CH_3)CH_2SC_2H_5$ | 0 | H | $2\text{-}CH_3\text{-}4\text{-}CF_2CF_3$ | |
| 1081 | $CH(CH_3)CH_2SC_2H_5$ | 0 | H | $2\text{-}CH_3\text{-}4\text{-}CF(CF_3)_2$ | |
| 1082 | $C(CH_3)_2CH_2SC_2H_5$ | 0 | H | $2\text{-}CH_3\text{-}4\text{-}CF_2CF_3$ | |
| 1083 | $C(CH_3)_2CH_2SC_2H_5$ | 0 | H | $2\text{-}CH_3\text{-}4\text{-}CF(CF_3)_2$ | |
| 1084 | $CH(CH_3)CH_2NHAc$ | 0 | H | $2\text{-}CH_3\text{-}4\text{-}CF_2CF_3$ | |
| 1085 | $CH(CH_3)CH_2NHAc$ | 0 | H | $2\text{-}CH_3\text{-}4\text{-}CF(CF_3)_2$ | |
| 1086 | $C(CH_3)_2CH_2NHAc$ | 0 | H | $2\text{-}CH_3\text{-}4\text{-}CF_2CF_3$ | |
| 1087 | $C(CH_3)_2CH_2NHAc$ | 0 | H | $2\text{-}CH_3\text{-}4\text{-}CF(CF_3)_2$ | |
| 1088 | $CH(CH_3)C_2H_4OCH_3$ | 0 | H | $2\text{-}CH_3\text{-}4\text{-}CF_2CF_3$ | |
| 1089 | $CH(CH_3)C_2H_4OCH_3$ | 0 | H | $2\text{-}CH_3\text{-}4\text{-}CF(CF_3)_2$ | |

TABLE 16

($Z^1 = Z^2 = O$, $R^2 = R^3 = H$, q = 0, Het = Q6, $B^1 = B^2 = B^3 = B^4 = C$)

| No | $R^1$ | p | Xn | Ym | Physical property m.p. ° C. |
|---|---|---|---|---|---|
| 1090 | $i\text{-}C_3H_7$ | 0 | H | $2\text{-}CH_3\text{-}4\text{-}CF_3$ | |
| 1091 | $i\text{-}C_3H_7$ | 0 | H | $2\text{-}CH_3\text{-}4\text{-}OCF_3$ | |
| 1092 | $i\text{-}C_3H_7$ | 0 | H | $2\text{-}CH_3\text{-}4\text{-}OCF_2CHF_2$ | |
| 1093 | $i\text{-}C_3H_7$ | 0 | H | $2\text{-}CH_3\text{-}4\text{-}OCH_2CF_2CHF_2$ | |
| 1094 | $i\text{-}C_3H_7$ | 0 | H | $2\text{-}CH_3\text{-}4\text{-}CF_2CF_3$ | |
| 1095 | $i\text{-}C_3H_7$ | 0 | H | $2\text{-}CH_3\text{-}4\text{-}CF(CF_3)_2$ | 191–193 |
| 1096 | $i\text{-}C_3H_7$ | 0 | H | $2\text{-}CH_3\text{-}4\text{-}SCH_2CF_2CHF_2$ | |
| 1097 | $i\text{-}C_3H_7$ | 0 | H | $2\text{-}CH_3\text{-}4\text{-}SO_2CH_2CF_2CHF_2$ | |
| 1098 | $i\text{-}C_3H_7$ | 0 | H | $2\text{-}Cl\text{-}4\text{-}CF(CF_2)_2$ | |
| 1099 | $i\text{-}C_3H_7$ | 0 | H | $2\text{-}Cl\text{-}4\text{-}CF_2CF_3$ | |
| 1100 | $i\text{-}C_3H_7$ | 0 | H | $2\text{-}C_2H_5\text{-}4\text{-}CF(CF_3)_2$ | |
| 1101 | $i\text{-}C_3H_7$ | 0 | H | $2\text{-}F\text{-}4\text{-}CF_2CF_3$ | |
| 1102 | $i\text{-}C_3H_7$ | 0 | 3-Cl | $2\text{-}CH_3\text{-}4\text{-}CF_2CF_3$ | |
| 1103 | $i\text{-}C_3H_7$ | 0 | 6-Cl | $2\text{-}CH_3\text{-}4\text{-}CF(CF_3)_2$ | |
| 1104 | $i\text{-}C_3H_7$ | 0 | 3-I | $2\text{-}CH_3\text{-}4\text{-}CF_2CF_3$ | |
| 1105 | $i\text{-}C_3H_7$ | 0 | 6-I | $2\text{-}CH_3\text{-}4\text{-}CF(CF_3)_2$ | |
| 1106 | $i\text{-}C_3H_7$ | 0 | $3\text{-}CH_3$ | $2\text{-}CH_3\text{-}4\text{-}CF_2CF_3$ | |
| 1107 | $i\text{-}C_3H_7$ | 0 | $6\text{-}CH_3$ | $2\text{-}CH_3\text{-}4\text{-}CF(CF_3)_2$ | |
| 1108 | $i\text{-}C_3H_7$ | 0 | $3\text{-}CF_3$ | $2\text{-}CH_3\text{-}4\text{-}CF(CF_3)_2$ | |
| 1109 | $CH(CH_3)CH_2SOCH_3$ | 0 | H | $2\text{-}CH_3\text{-}4\text{-}CF_2CF_3$ | |
| 1110 | $CH(CH_3)CH_2SCH_3$ | 0 | H | $2\text{-}CH_3\text{-}4\text{-}CF(CF_3)_2$ | 85–95 |
| 1111 | $CH(CH_3)CH_2SOC_2H_5$ | 0 | H | $2\text{-}CH_3\text{-}4\text{-}CF_2CF_3$ | |
| 1112 | $CH(CH_3)CH_2SC_2H_5$ | 0 | H | $2\text{-}CH_3\text{-}4\text{-}CF(CF_3)_2$ | |
| 1113 | $C(CH_3)_2CH_2SC_2H_5$ | 0 | H | $2\text{-}CH_3\text{-}4\text{-}CF_2CF_3$ | |
| 1114 | $C(CH_3)_2CH_2SOC_2H_5$ | 0 | H | $2\text{-}CH_3\text{-}4\text{-}CF(CF_3)_2$ | |
| 1115 | $CH(CH_3)CH_2NHAc$ | 0 | H | $2\text{-}CH_3\text{-}4\text{-}CF_2CF_3$ | |
| 1116 | $CH(CH_3)CH_2NHAc$ | 0 | H | $2\text{-}CH_3\text{-}4\text{-}CF(CF_3)_2$ | |
| 1117 | $C(CH_3)_2CH_2NHAC$ | 0 | H | $2\text{-}CH_3\text{-}4\text{-}CF_2CF_3$ | |
| 1118 | $C(CH_3)_2CH_2NHAc$ | 0 | H | $2\text{-}CH_3\text{-}4\text{-}CF(CF_3)_2$ | |
| 1119 | $CH(CH_3)C_2H_4OCH_3$ | 0 | H | $2\text{-}CH_3\text{-}4\text{-}CF_2CF_3$ | |
| 1120 | $CH(CH_3)C_2H_4OCH_3$ | 0 | H | $2\text{-}CH_3\text{-}4\text{-}CF(CF_3)_2$ | |
| 1121 | $CH(CH_3)C_2H_4OCH_3$ | 0 | H | $2\text{-}C_2H_5\text{-}4\text{-}CF(CF_3)_2$ | |

TABLE 17

($Z^1 = Z^2 = O$, $R^2 = R^3 = H$, q = 0, Het = Q7, $B^1 = B^2 = B^3 = B^4 = C$)

| No | $R^1$ | p | Xn | Ym | Physical property m.p. ° C. |
|---|---|---|---|---|---|
| 1122 | $i\text{-}C_3H_7$ | 0 | H | $2\text{-}CH_3\text{-}4\text{-}CF_3$ | |
| 1123 | $i\text{-}C_3H_7$ | 0 | H | $2\text{-}CH_3\text{-}4\text{-}OCF_3$ | |

TABLE 17-continued ($Z^1 = Z^2 = O$, $R^2 = R^3 = H$, q = 0, Het = Q7, $B^1 = B^2 = B^3 = B^4 = C$)

| No | $R^1$ | p | Xn | Ym | Physical property m.p. ° C. |
|---|---|---|---|---|---|
| 1124 | i-$C_3H_7$ | 0 | H | 2-$CH_3$-4-$OCF_2CHF_2$ | |
| 1125 | i-$C_3H_7$ | 0 | H | 2-$CH_3$-4-$OCH_2CF_2CHF_2$ | |
| 1126 | i-$C_3H_7$ | 0 | H | 2-$CH_3$-4-$CF_2CF_3$ | |
| 1127 | i-$C_3H_7$ | 0 | H | 2-$CH_3$-4-$CF(CF_3)_2$ | 204–206 |
| 1128 | i-$C_3H_7$ | 0 | H | 2-$CH_3$-4-$SCH_2CF_2CHF_2$ | |
| 1129 | i-$C_3H_7$ | 0 | H | 2-$CH_3$-4-$SO_2CH_2CF_2CHF_2$ | |
| 1130 | i-$C_3H_7$ | 0 | H | 2-Cl-4-$CF(CF_2)_2$ | |
| 1131 | i-$C_3H_7$ | 0 | H | 2-Cl-4-$CF_2CF_3$ | |
| 1132 | i-$C_3H_7$ | 0 | H | 2-$C_2H_5$-4-$CF(CF_3)_2$ | |
| 1133 | i-$C_3H_7$ | 0 | H | 2-F-4-$CF_2CF_3$ | |
| 1134 | i-$C_3H_7$ | 0 | 5-Cl | 2-$CH_3$-4-$CF_2CF_3$ | |
| 1135 | i-$C_3H_7$ | 0 | 6-Cl | 2-$CH_3$-4-$CF(CF_3)_2$ | |
| 1136 | i-$C_3H_7$ | 0 | 5-I | 2-$CH_3$-4-$CF_2CF_3$ | |
| 1137 | i-$C_3H_7$ | 0 | 6-I | 2-$CH_3$-4-$CF(CF_3)_2$ | |
| 1138 | i-$C_3H_7$ | 0 | 5-$CH_3$ | 2-$CH_3$-4-$CF_2CF_3$ | |
| 1139 | i-$C_3H_7$ | 0 | 6-$CH_3$ | 2-$CH_3$-4-$CF(CF_3)_2$ | |
| 1140 | i-$C_3H_7$ | 0 | 5-$CF_3$ | 2-$CH_3$-4-$CF(CF_3)_2$ | |
| 1141 | $CH(CH_3)CH_2SOCH_3$ | 0 | H | 2-$CH_3$-4-$CF_2CF_3$ | |
| 1142 | $CH(CH_3)CH_2SCH_3$ | 0 | H | 2-$CH_3$-4-$CF(CF_3)_2$ | |
| 1143 | $CH(CH_3)CH_2SOC_2H_5$ | 0 | H | 2-$CH_3$-4-$CF_2CF_3$ | |
| 1144 | $CH(CH_3)CH_2SC_2H_5$ | 0 | H | 2-$CH_3$-4-$CF(CF_3)_2$ | |
| 1145 | $C(CH_3)_2CH_2SC_2H_5$ | 0 | H | 2-$CH_3$-4-$CF_2CF_3$ | |
| 1146 | $C(CH_3)_2CH_2SOC_2H_5$ | 0 | H | 2-$CH_3$-4-$CF(CF_3)_2$ | |
| 1147 | $CH(CH_3)CH_2NHAc$ | 0 | H | 2-$CH_3$-4-$CF_2CF_3$ | |
| 1148 | $CH(CH_3)CH_2NHAc$ | 0 | H | 2-$CH_3$-4-$CF(CF_3)_2$ | |
| 1149 | $C(CH_3)_2CH_2NHAc$ | 0 | H | 2-$CH_3$-4-$CF_2CF_3$ | |
| 1150 | $C(CH_3)_2CH_2NHAc$ | 0 | H | 2-$CH_3$-4-$CF(CF_3)_2$ | |
| 1151 | $CH(CH_3)C_2H_4OCH_3$ | 0 | H | 2-$CH_3$-4-$CF_2CF_3$ | |
| 1152 | $CH(CH_3)C_2H_4OCH_3$ | 0 | H | 2-$CH_3$-4-$CF(CF_3)_2$ | |

TABLE 18

($Z^1 = Z^2 = O$, $R^2 = R^3 = H$, q = O, Het = Q8, $B^1 = B^2 = B^3 = B^4 = C$)

| No | $R^1$ | p | Xn | Ym | Physical property m.p. ° C. |
|---|---|---|---|---|---|
| 1153 | i-$C_3H_7$ | 0 | H | 2-$CH_3$-4-$CF_3$ | |
| 1154 | i-$C_3H_7$ | 0 | H | 2-$CH_3$-4-$OCF_3$ | |
| 1155 | i-$C_3H_7$ | 0 | H | 2-$CH_3$-4-$OCF_2CHF_2$ | |
| 1156 | i-$C_3H_7$ | 0 | H | 2-$CH_3$-4-$OCH_2CF_2CHF_2$ | |
| 1157 | i-$C_3H_7$ | 0 | H | 2-$CH_3$-4-$CF_2CF_3$ | |
| 1158 | i-$C_3H_7$ | 0 | H | 2-$CH_3$-4-$CF(CF_3)_2$ | 192–194 |
| 1159 | i-$C_3H_7$ | 0 | H | 2-$CH_3$-4-$SCH_2CF_2CHF_2$ | |
| 1160 | i-$C_3H_7$ | 0 | H | 2-$CH_3$-4-$SO_2CH_2CF_2CHF_2$ | |
| 1161 | i-$C_3H_7$ | 0 | H | 2-Cl-4-$CF(CF_2)_2$ | |
| 1162 | i-$C_3H_7$ | 0 | H | 2-Cl-4-$CF_2CF_3$ | |
| 1163 | i-$C_3H_7$ | 0 | H | 2-$C_2H_5$-4-$CF(CF_3)_2$ | |
| 1164 | i-$C_3H_7$ | 0 | H | 2-F-4-$CF_2CF_3$ | |
| 1165 | i-$C_3H_7$ | 0 | 6-Cl | 2-$CH_3$-4-$CF_2CF_3$ | |
| 1166 | i-$C_3H_7$ | 0 | 6-Cl | 2-$CH_3$-4-$CF(CF_3)_2$ | |
| 1167 | i-$C_3H_7$ | 0 | 6-I | 2-$CH_3$-4-$CF_2CF_3$ | |
| 1168 | i-$C_3H_7$ | 0 | 6-I | 2-$CH_3$-4-$CF(CF_3)_2$ | |
| 1169 | i-$C_3H_7$ | 0 | 2-$CH_3$ | 2-$CH_3$-4-$CF_2CF_3$ | |
| 1170 | i-$C_3H_7$ | 0 | 2-$SCH_3$ | 2-$CH_3$-4-$CF(CF_3)_2$ | 204–206 |
| 1171 | i-$C_3H_7$ | 0 | 6-$CF_3$ | 2-$CH_3$-4-$CF(CF_3)_2$ | |
| 1172 | $CH(CH_3)CH_2SOCH_3$ | 0 | H | 2-$CH_3$-4-$CF_2CF_3$ | |
| 1173 | $CH(CH_3)CH_2SCH_3$ | 0 | 2-$SCH_3$ | 2-$CH_3$-4-$CF(CF_3)_2$ | 168–170 |
| 1174 | $CH(CH_3)CH_2SOC_2H_5$ | 0 | H | 2-$CH_3$-4-$CF_2CF_3$ | |
| 1175 | $CH(CH_3)CH_2SC_2H_5$ | 0 | H | 2-$CH_3$-4-$CF(CF_3)_2$ | |
| 1176 | $C(CH_3)_2CH_2SC_2H_5$ | 0 | H | 2-$CH_3$-4-$CF_2CF_3$ | |
| 1177 | $C(CH_3)_2CH_2SOC_2H_5$ | 0 | H | 2-$CH_3$-4-$CF(CF_3)_2$ | |
| 1178 | $CH(CH_3)CH_2NHAc$ | 0 | H | 2-$CH_3$-4-$CF_2CF_3$ | |
| 1179 | $CH(CH_3)CH_2NHAc$ | 0 | H | 2-$CH_3$-4-$CF(CF_3)_2$ | |
| 1180 | $C(CH_3)_2CH_2NHAc$ | 0 | H | 2-$CH_3$-4-$CF_2CF_3$ | |
| 1181 | $C(CH_3)_2CH_2NHAc$ | 0 | H | 2-$CH_3$-4-$CF(CF_3)_2$ | |

TABLE 18-continued ($Z^1 = Z^2 = O$, $R^2 = R^3 = H$, $q = 0$, Het = Q8, $B^1 = B^2 = B^3 = B^4 = C$)

| No | $R^1$ | p | Xn | Ym | Physical property m.p. ° C. |
|---|---|---|---|---|---|
| 1182 | $CH(CH_3)C_2H_4OCH_3$ | 0 | H | $2\text{-}CH_3\text{-}4\text{-}CF_2CF_3$ | |
| 1183 | $CH(CH_3)C_2H_4OCH_3$ | 0 | H | $2\text{-}CH_3\text{-}4\text{-}CF(CF_3)_2$ | |

TABLE 19

($Z^1 = Z^2 = O$, $R^2 = R^3 = H$, $q = 0$, Het = Q9, $B^1 = B^2 = B^3 = B^4 = C$)

| No | $R^1$ | p | Xn | Ym | Physical property m.p. ° C. |
|---|---|---|---|---|---|
| 1184 | $i\text{-}C_3H_7$ | 0 | H | $2\text{-}CH_3\text{-}4\text{-}CF_3$ | |
| 1185 | $i\text{-}C_3H_7$ | 0 | H | $2\text{-}CH_3\text{-}4\text{-}OCF_3$ | |
| 1186 | $i\text{-}C_3H_7$ | 0 | H | $2\text{-}CH_3\text{-}4\text{-}OCF_2CHF_2$ | |
| 1187 | $i\text{-}C_3H_7$ | 0 | H | $2\text{-}CH_3\text{-}4\text{-}OCH_2CF_2CHF_2$ | |
| 1188 | $i\text{-}C_3H_7$ | 0 | H | $2\text{-}CH_3\text{-}4\text{-}CF_2CF_3$ | |
| 1189 | $i\text{-}C_3H_7$ | 0 | H | $2\text{-}CH_3\text{-}4\text{-}CF(CF_3)_2$ | 162–164 |
| 1190 | $i\text{-}C_3H_7$ | 0 | H | $2\text{-}CH_3\text{-}4\text{-}SCH_2CF_2CHF_2$ | |
| 1191 | $i\text{-}C_3H_7$ | 0 | H | $2\text{-}CH_3\text{-}4\text{-}SO_2CH_2CF_2CHF_2$ | |
| 1192 | $i\text{-}C_3H_7$ | 0 | H | $2\text{-}Cl\text{-}4\text{-}CF(CF_2)_2$ | |
| 1193 | $i\text{-}C_3H_7$ | 0 | H | $2\text{-}Cl\text{-}4\text{-}CF_2CF_3$ | |
| 1194 | $i\text{-}C_3H_7$ | 0 | H | $2\text{-}C_2H_5\text{-}4\text{-}CF(CF_3)_2$ | |
| 1195 | $i\text{-}C_3H_7$ | 0 | H | $2\text{-}F\text{-}4\text{-}CF_2CF_3$ | |
| 1196 | $i\text{-}C_3H_7$ | 0 | 6-Cl | $2\text{-}CH_3\text{-}4\text{-}CF_2CF_3$ | |
| 1197 | $i\text{-}C_3H_7$ | 0 | 6-Cl | $2\text{-}CH_3\text{-}4\text{-}CF(CF_3)_2$ | |
| 1198 | $i\text{-}C_3H_7$ | 0 | 6-I | $2\text{-}CH_3\text{-}4\text{-}CF_2CF_3$ | |
| 1199 | $i\text{-}C_3H_7$ | 0 | 6-I | $2\text{-}CH_3\text{-}4\text{-}CF(CF_3)_2$ | |
| 1200 | $i\text{-}C_3H_7$ | 0 | $2\text{-}CH_3$ | $2\text{-}CH_3\text{-}4\text{-}CF_2CF_3$ | |
| 1201 | $i\text{-}C_3H_7$ | 0 | $2\text{-}SCH_3$ | $2\text{-}CH_3\text{-}4\text{-}CF(CF_3)_2$ | |
| 1202 | $i\text{-}C_3H_7$ | 0 | $6\text{-}CF_3$ | $2\text{-}CH_3\text{-}4\text{-}CF(CF_3)_2$ | |
| 1203 | $CH(CH_3)CH_2SOCH_3$ | 0 | H | $2\text{-}CH_3\text{-}4\text{-}CF_2CF_3$ | |
| 1204 | $CH(CH_3)CH_2SCH_3$ | 0 | $2\text{-}SCH_3$ | $2\text{-}CH_3\text{-}4\text{-}CF(CF_3)_2$ | 129–131 |
| 1205 | $CH(CH_3)CH_2SOC_2H_5$ | 0 | H | $2\text{-}CH_3\text{-}4\text{-}CF_2CF_3$ | |
| 1206 | $CH(CH_3)CH_2SC_2H_5$ | 0 | H | $2\text{-}CH_3\text{-}4\text{-}CF(CF_3)_2$ | |
| 1207 | $C(CH_3)_2CH_2SC_2H_5$ | 0 | H | $2\text{-}CH_3\text{-}4\text{-}CF_2CF_3$ | |
| 1208 | $C(CH_3)_2CH_2SOC_2H_5$ | 0 | H | $2\text{-}CH_3\text{-}4\text{-}CF(CF_3)_2$ | |
| 1209 | $CH(CH_3)CH_2NHAc$ | 0 | H | $2\text{-}CH_3\text{-}4\text{-}CF_2CF_3$ | |
| 1210 | $CH(CH_3)CH_2NHAc$ | 0 | H | $2\text{-}CH_3\text{-}4\text{-}CF(CF_3)_2$ | |
| 1211 | $C(CH_3)_2CH_2NHAc$ | 0 | H | $2\text{-}CH_3\text{-}4\text{-}CF_2CF_3$ | |
| 1212 | $C(CH_3)_2CH_2NHAc$ | 0 | H | $2\text{-}CH_3\text{-}4\text{-}CF(CF_3)_2$ | |
| 1213 | $CH(CH_3)C_2H_4OCH_3$ | 0 | H | $2\text{-}CH_3\text{-}4\text{-}CF_2CF_3$ | |
| 1214 | $CH(CH_3)C_2H_4OCH_3$ | 0 | H | $2\text{-}CH_3\text{-}4\text{-}CF(CF_3)_2$ | |

TABLE 20

($Z^1 = Z^2 = O$, $R^2 = R^3 = H$, $q = 0$, Het = Q10, $B^1 = B^2 = B^3 = B^4 = C$)

| No | $R^1$ | p | Xn | Ym | Physical property m.p. ° C. |
|---|---|---|---|---|---|
| 1215 | $i\text{-}C_3H_7$ | 0 | H | $2\text{-}CH_3\text{-}4\text{-}CF_3$ | |
| 1216 | $i\text{-}C_3H_7$ | 0 | H | $2\text{-}CH_3\text{-}4\text{-}OCF_3$ | |
| 1217 | $i\text{-}C_3H_7$ | 0 | H | $2\text{-}CH_3\text{-}4\text{-}OCF_2CHF_2$ | |
| 1218 | $i\text{-}C_3H_7$ | 0 | H | $2\text{-}CH_3\text{-}4\text{-}OCH_2CF_2CHF_2$ | |
| 1219 | $i\text{-}C_3H_7$ | 0 | H | $2\text{-}CH_3\text{-}4\text{-}CF_2CF_3$ | |
| 1220 | $i\text{-}C_3H_7$ | 0 | H | $2\text{-}CH_3\text{-}4\text{-}CF(CF_3)_2$ | 153–155 |
| 1221 | $i\text{-}C_3H_7$ | 1 | H | $2\text{-}CH_3\text{-}4\text{-}CF(CF_3)_2$ | paste |
| 1222 | $i\text{-}C_3H_7$ | 0 | H | $2\text{-}CH_3\text{-}4\text{-}SO_2CH_2CF_2CHF_2$ | |
| 1223 | $i\text{-}C_3H_7$ | 0 | H | $2\text{-}Cl\text{-}4\text{-}CF(CF_2)_2$ | |
| 1224 | $i\text{-}C_3H_7$ | 0 | H | $2\text{-}Cl\text{-}4\text{-}CF_2CF_3$ | |
| 1225 | $i\text{-}C_3H_7$ | 0 | H | $2\text{-}C_2H_5\text{-}4\text{-}CF(CF_3)_2$ | |

TABLE 20-continued ($Z^1 = Z^2 = O$, $R^2 = R^3 = H$, $q = 0$, Het = Q10, $B^1 = B^2 = B^3 = B^4 = C$)

| No | $R^1$ | p | Xn | Ym | Physical property m.p. ° C. |
|---|---|---|---|---|---|
| 1226 | i-$C_3H_7$ | 0 | H | 2-F-4-$CF_2CF_3$ | |
| 1227 | i-$C_3H_7$ | 0 | 6-Cl | 2-$CH_3$-4-$CF_2CF_3$ | |
| 1228 | i-$C_3H_7$ | 0 | 6-Cl | 2-$CH_3$-4-$CF(CF_3)_2$ | |
| 1229 | i-$C_3H_7$ | 0 | 6-I | 2-$CH_3$-4-$CF_2CF_3$ | |
| 1230 | i-$C_3H_7$ | 0 | 6-I | 2-$CH_3$-4-$CF(CF_3)_2$ | |
| 1231 | i-$C_3H_7$ | 0 | 2-$CH_3$ | 2-$CH_3$-4-$CF_2CF_3$ | |
| 1232 | i-$C_3H_7$ | 0 | 2-$CH_3$ | 2-$CH_3$-4-$CF(CF_3)_2$ | |
| 1233 | i-$C_3H_7$ | 0 | 6-$CF_3$ | 2-$CH_3$-4-$CF(CF_3)_2$ | |
| 1234 | $CH(CH_3)CH_2SCH_3$ | 0 | H | 2-$CH_3$-4-$CF_2CF_3$ | |
| 1235 | $CH(CH_3)CH_2SOCH_3$ | 0 | H | 2-$CH_3$-4-$CF_2CF_3$ | |
| 1236 | $CH(CH_3)CH_2SCH_3$ | 0 | H | 2-$CH_3$-4-$CF(CF_3)_2$ | |
| 1237 | $CH(CH_3)CH_2SOC_2H_5$ | 0 | R | 2-$CH_3$-4-$CF_2CF_3$ | |
| 1238 | $CH(CH_3)CH_2SC_2H_5$ | 0 | H | 2-$CH_3$-4-$CF(CF_3)_2$ | |
| 1239 | $C(CH_3)_2CH_2SC_2H_5$ | 0 | H | 2-$CH_3$-4-$CF_2CF_3$ | |
| 1240 | $C(CH_3)_2CH_2SOC_2H_5$ | 0 | H | 2-$CH_3$-4-$CF(CF_3)_2$ | |
| 1241 | $CH(CH_3)CH_2NHAc$ | 0 | H | 2-$CH_3$-4-$CF_2CF_3$ | |
| 1242 | $CH(CH_3)CH_2NHAc$ | 0 | H | 2-$CH_3$-4-$CF(CF_3)_2$ | |
| 1243 | $C(CH_3)_2CH_2NHAc$ | 0 | H | 2-$CH_3$-4-$CF_2CF_3$ | |
| 1244 | $C(CH_3)_2CH_2NHAc$ | 0 | H | 2-$CH_3$-4-$CF(CF_3)_2$ | |
| 1245 | $CH(CH_3)C_2H_4OCH_3$ | 0 | H | 2-$CH_3$-4-$CF_2CF_3$ | |
| 1246 | $CH(CH_3)C_2H_4OCH_3$ | 0 | H | 2-$CH_3$-4-$CF(CF_3)_2$ | |

TABLE 21

($Z^1 = Z^2 = O$, $R^2 = R^3 = H$, Het = Q11, $B^1 = B^2 = B^3 = B^4 = C$)

| No | $R^1$ | W | Xn | Ym | Physical property m.p. ° C. |
|---|---|---|---|---|---|
| 1247 | i-$C_3H_7$ | O | H | 2-$CH_3$-4-$CF_2CF_3$ | 145–146 |
| 1248 | i-$C_3H_7$ | O | 4,5-$(CH_3)_2$ | 4-$OCF_3$ | 148 |
| 1249 | t-$C_4H_9$ | O | H | 2-$CH_3$-4-$CF_2CF_3$ | 139–141 |
| 1250 | i-$C_3H_7$ | S | H | 2-$CH_3$-4-$OCH_2CF_2CHF_2$ | |
| 1251 | i-$C_3H_7$ | S | H | 2-$CH_3$-4-$CF_2CF_3$ | 164–165 |
| 1252 | i-$C_3H_7$ | S | H | 2-$CH_3$-4-$CF(CF_3)_2$ | |
| 1253 | i-$C_3H_7$ | S | 4-I | 2-$CH_3$-4-$CF(CF_3)_2$ | |
| 1254 | i-$C_3H_7$ | S | H | 2-$CH_3$-4-$SO_2CH_2CF_2CHF_2$ | |
| 1255 | i-$C_3H_7$ | S | 4-I | 2-$CH_3$-4-$CF_2CF_3$ | 202–204 |
| 1256 | t-$C_4H_9$ | S | H | 2-$CH_3$-4-$CF_2CF_3$ | 178–180 |
| 1257 | i-$C_3H_7$ | S | H | 2-$C_2H_5$-4-$CF(CF_3)_2$ | |
| 1258 | i-$C_3H_7$ | $NCH_3$ | 4-Cl | 2-$CH_3$-4-$CF(CF_3)_2$ | |
| 1259 | i-$C_3H_7$ | $NCH_3$ | 4-I | 2-$CH_3$-4-$CF(CF_3)_2$ | |
| 1250 | i-$C_3H_7$ | $NCH_3$ | H | 2-$CH_3$-4-$CF_2CF_3$ | |
| 1251 | i-$C_3H_7$ | $NCH_3$ | H | 2-$CH_3$-4-$CF(CF_3)_2$ | |
| 1252 | i-$C_3H_7$ | NPh | H | 2-$CH_3$-4-$CF_2CF_3$ | |
| 1253 | i-$C_3H_7$ | NPh | 4-Cl | 2-$CH_3$-4-$CF(CF_3)_2$ | |
| 1254 | i-$C_3H_7$ | $NCH_3$ | 4-CH=CF—CH=CH-5 | 2-$CH_3$-4-$CF(CF_3)_2$ | 189–191 |
| 1255 | $CH(CH_3)CH_2SCH_3$ | $NCH_3$ | 4-CH=CF—CH=CH-5 | 2-$CH_3$-4-$CF(CF_3)_2$ | 171–173 |
| 1256 | $CH(CH_3)C_2H_4OCH_3$ | O | H | 2-$CH_3$-4-$CF(CF_3)_2$ | |
| 1257 | $CH(CH_3)CH_2SCH_3$ | S | H | 2-$CH_3$-4-$CF_2CF_3$ | |
| 1258 | $CH(CH_3)CH_2SOCH_3$ | S | H | 2-$CH_3$-4-$CF_2CF_3$ | |
| 1259 | $CH(CH_3)CH_2SOC_2H_5$ | S | H | 2-$CH_3$-4-$CF(CF_3)_2$ | |
| 1260 | $CH(CH_3)CH_2SC_2H_5$ | S | H | 2-$CH_3$-4-$CF_2CF_3$ | |
| 1261 | $C(CH_3)_2CH_2SC_2H_5$ | S | H | 2-$CH_3$-4-$CF(CF_3)_2$ | |
| 1262 | $C(CH_3)_2CH_2SOC_2H_5$ | S | H | 2-$CH_3$-4-$CF_2CF_3$ | |
| 1263 | $CH(CH_3)CH_2NHAc$ | S | H | 2-$CH_3$-4-$CF(CF_3)_2$ | |
| 1264 | $C(CH_3)_2CH_2NHAc$ | S | H | 2-$CH_3$-4-$CF_2CF_3$ | |
| 1265 | $CH(CH_3)C_2H_4OCH_3$ | S | H | 2-$CH_3$-4-$CF(CF_3)_2$ | |

TABLE 22

($Z^1 = Z^2 = O$, $R^3 = H$, Het = Q11, $B^1 = B^2 = B^3 = B^4 = C$)

| No. | $R^1$ | $R^2$ | W | Xn | Ym | Physical property m.p. ° C. |
|---|---|---|---|---|---|---|
| 1266 | $C_2H_5$ | $C_2H_5$ | O | H | 2-$CH_3$-4-$CF_2CF_3$ | 92–93 |
| 1267 | $C_2H_5$ | $C_2H_5$ | O | H | 2-$CH_3$-4-$OCF_3$ | 81–82 |
| 1268 | $C_2H_5$ | $C_2H_5$ | S | H | 2-$CH_3$-4-$CF_2CF_3$ | 160–162 |
| 1269 | [2-$CH_3$-4-$CF(CF_3)_2$]Ph | H | $NCH_3$ | 4-CH=CF—CH=CH-5 | 2-$CH_3$-4-$CF(CF_3)_2$ | 256–258 |

TABLE 23

($Z^1 = Z^2 = O$, $R^2 = R^3 = H$, Het = Q12, $B^1 = B^2 = B^3 = B^4 = C$)

| No | $R^1$ | W | Xn | Ym | Physical property m.p. ° C. |
|---|---|---|---|---|---|
| 1270 | i-$C_3H_7$ | O | H | 2-$CH_3$-4-$CF_3$ | |
| 1271 | i-$C_3H_7$ | O | H | 4-$OCF_3$ | 170 |
| 1272 | i-$C_3H_7$ | O | H | 2-$CH_3$-4-$OCF_2CHF_2$ | |
| 1273 | i-$C_3H_7$ | S | H | 2-$CH_3$-4-$OCH_2CF_2CHF_2$ | |
| 1274 | i-$C_3H_7$ | S | 2-Cl | 2-$CH_3$-4-$CF_2CF_3$ | |
| 1275 | i-$C_3H_7$ | S | H | 2-$CH_3$-4-$CF(CF_3)_2$ | 140–145 |
| 1276 | i-$C_3H_7$ | S | 2-I | 2-$CH_3$-4-$CF(CF_3)_2$ | |
| 1277 | i-$C_3H_7$ | S | H | 2-$CH_3$-4-$SO_2CH_2CF_2CHF_2$ | |
| 1278 | i-$C_3H_7$ | S | H | 2-Cl-4-$CF(CF_2)_2$ | |
| 1279 | i-$C_3H_7$ | S | H | 2-$CH_3$-5-$CF_2CF_3$ | 125–130 |
| 1280 | i-$C_3H_7$ | S | H | 2-$CH_3$-3-$CF_2CF_3$ | paste |
| 1281 | i-$C_3H_7$ | S | H | 2-F-4-$CF_2CF_3$ | |
| 1282 | i-$C_3H_7$ | $NCH_3$ | 2-I | 2-$CH_3$-4-$CF_2CF_3$ | |
| 1283 | i-$C_3H_7$ | $NCH_3$ | 2-I | 2-$CH_3$-4-$CF(CF_3)_2$ | |
| 1284 | i-$C_3H_7$ | $NCH_3$ | H | 2-$CH_3$-4-$CF_2CF_3$ | |
| 1285 | i-$C_3H_7$ | $NCH_3$ | H | 2-$CH_3$-4-$CF(CF_3)_2$ | |
| 1286 | i-$C_3H_7$ | NPh | H | 2-$CH_3$-4-$CF_2CF_3$ | |
| 1287 | i-$C_3H_7$ | NPh | 2-I | 2-$CH_3$-4-$CF(CF_3)_2$ | |
| 1288 | i-$C_3H_7$ | NPh | H | 2-Cl-4-$CF_2CF_3$ | |
| 1289 | $CH(CH_3)CH_2SCH_3$ | S | H | 2-$CH_3$-4-$CF_2CF_3$ | |
| 1290 | $CH(CH_3)CH_2SOCH_3$ | S | H | 2-$CH_3$-4-$CF_2CF_3$ | |
| 1291 | $CH(CH_3)CH_2SCH_3$ | S | H | 2-$CH_3$-4-$CF(CF_3)_2$ | |
| 1292 | $CH(CH_3)CH_2SOC_2H_5$ | S | H | 2-$CH_3$-4-$CF_2CF_3$ | |
| 1293 | $CH(CH_3)CH_2SC_2H_5$ | S | H | 2-$CH_3$-4-$CF(CF_3)_2$ | |
| 1294 | $C(CH_3)_2CH_2SC_2H_5$ | S | H | 2-$CH_3$-4-$CF_2CF_3$ | |
| 1295 | $C(CH_3)_2CH_2SOC_2H_5$ | S | H | 2-$CH_3$-4-$CF(CF_3)_2$ | |
| 1296 | $CH(CH_3)CH_2NHAc$ | S | H | 2-$CH_3$-4-$CF_2CF_3$ | |
| 1297 | $CH(CH_3)CH_2NHAc$ | S | H | 2-$CH_3$-4-$CF(CF_3)_2$ | |
| 1298 | $C(CH_3)_2CH_2NHAc$ | S | H | 2-$CH_3$-4-$CF_2CF_3$ | |
| 1299 | $C(CH_3)_2CH_2NHAc$ | S | H | 2-$CH_3$-4-$CF(CF_3)_2$ | |
| 1300 | $CH(CH_3)C_2H_4OCH_3$ | S | H | 2-$CH_3$-4-$CF_2CF_3$ | |
| 1301 | $CH(CH_3)C_2H_4OCH_3$ | S | H | 2-$CH_3$-4-$CF(CF_3)_2$ | |

TABLE 24

($Z^1 = Z^2 = O$, $R^3 = H$, Het = Q13, $B^1 = B^2 = B^3 = B^4 = C$)

| No | $R^1$ | $R^2$ | W | Xn | Ym | Physical property m.p. ° C. |
|---|---|---|---|---|---|---|
| 1302 | i-$C_3H_7$ | H | O | H | 2-$CH_3$-4-$CF_3$ | |
| 1303 | i-$C_3H_7$ | H | O | 4,5-$(CH_3)_2$ | 4-$OCF_3$ | 134 |
| 1304 | i-$C_3H_7$ | H | O | H | 2-$CH_3$-4-$OCF_2CHF_2$ | |
| 1305 | i-$C_3H_7$ | H | S | H | 2-$CH_3$-4-$OCH_2CF_2CHF_2$ | |
| 1306 | i-$C_3H_7$ | H | S | H | 2-$CH_3$-4-$OCF_3$ | 139–141 |
| 1307 | i-$C_3H_7$ | H | S | H | 2-$CH_3$-4-$CF_2CF_3$ | 159–161 |
| 1308 | i-$C_3H_7$ | H | S | 4-I | 2-$CH_3$-4-$CF(CF_3)_2$ | |
| 1309 | i-$C_3H_7$ | H | S | H | 2-$CH_3$-4-$CF(CF_3)_2$ | |
| 1310 | i-$C_3H_7$ | H | S | H | 2-Cl-4-$CF(CF_2)_2$ | |

TABLE 24-continued ($Z^1 = Z^2 = O, R^3 = H$, Het = Q13, $B^1 = B^2 = B^3 = B^4 = C$)

| No | $R^1$ | $R^2$ | W | Xn | Ym | Physical property m.p. ° C. |
|---|---|---|---|---|---|---|
| 1311 | $C_2H_5$ | $C_2H_5$ | S | H | 2-$CH_3$-4-$CF_2CF_3$ | 120–122 |
| 1312 | $C_2H_5$ | $C_2H_5$ | S | H | 2-$C_2H_5$-4-$CF(CF_3)_2$ | |
| 1313 | $C_2H_5$ | $C_2H_5$ | S | H | 2-$CH_3$-4-$OCF_3$ | 153–155 |
| 1314 | i-$C_3H_7$ | H | $NCH_3$ | 4-I | 2-$CH_3$-4-$CF_2CF_3$ | |
| 1315 | i-$C_3H_7$ | H | NPh | 4-I | 2-$CH_3$-4-$CF(CF_3)_2$ | |
| 1316 | i-$C_3H_7$ | H | NPh | H | 2-$CH_3$-4-$CF_2CF_3$ | |
| 1317 | i-$C_3H_7$ | H | NPh | H | 2-$CH_3$-4-$CF(CF_3)_2$ | |
| 1318 | i-$C_3H_7$ | H | $NCH_3$ | H | 2-$CH_3$-4-$CF_2CF_3$ | |
| 1319 | i-$C_3H_7$ | H | $NCH_3$ | 4-I | 2-$CH_3$-4-$CF(CF_3)_2$ | |
| 1320 | i-$C_3H_7$ | H | $NCH_3$ | 4-CH=CF—CH=CH-5 | 2-$CH_3$-4-$CF(CF_3)_2$ | 195–205 |
| 1321 | $CH(CH_3)CH_2SCH_3$ | H | S | H | 2-$CH_3$-4-$CF_2CF_3$ | |
| 1322 | $CH(CH_3)CH_2SOCH_3$ | H | S | H | 2-$CH_3$-4-$CF_2CF_3$ | |
| 1323 | $CH(CH_3)CH_2SCH_3$ | H | S | H | 2-$CH_3$-4-$CF(CF_3)_2$ | |
| 1324 | $CH(CH_3)CH_2SOC_2H_5$ | H | S | H | 2-$CH_3$-4-$CF_2CF_3$ | |
| 1325 | $CH(CH_3)CH_2SC_2H_5$ | H | S | H | 2-$CH_3$-4-$CF(CF_3)_2$ | |
| 1326 | $C(CH_3)_2CH_2SC_2H_5$ | H | S | H | 2-$CH_3$-4-$CF_2CF_3$ | |
| 1327 | $C(CH_3)_2CH_2SOC_2H_5$ | H | S | H | 2-$CH_3$-4-$CF(CF_3)_2$ | |
| 1328 | $CH(CH_3)CH_2NHAc$ | H | S | H | 2-$CH_3$-4-$CF_2CF_3$ | |
| 1329 | $CH(CH_3)CH_2NHAc$ | H | S | H | 2-$CH_3$-4-$CF(CF_3)_2$ | |
| 1330 | $C(CH_3)_2CH_2NHAc$ | H | S | H | 2-$CH_3$-4-$CF_2CF_3$ | |
| 1331 | $C(CH_3)_2CH_2NHAc$ | H | S | H | 2-$CH_3$-4-$CF(CF_3)_2$ | |
| 1332 | $CH(CH_3)C_2H_4OCH_3$ | H | S | H | 2-$CH_3$-4-$CF_2CF_3$ | |
| 1333 | $CH(CH_3)C_2H_4OCH_3$ | H | S | H | 2-$CH_3$-4-$CF(CF_3)_2$ | |

TABLE 25

($Z^1 = Z^2 = O, R^2 = R^3 = H$, Het = Q14, $B^1 = B^2 = B^3 = B^4 = C$)

| No | $R^1$ | W | Xn | Ym | Physical property m.p. ° C. |
|---|---|---|---|---|---|
| 1334 | i-$C_3H_7$ | O | H | 2-$CH_3$-4-$CF_3$ | |
| 1335 | i-$C_3H_7$ | O | 3-$CH_3$ | 4-$OCF_3$ | 137–138 |
| 1336 | i-$C_3H_7$ | O | H | 2-$CH_3$-4-$OCF_2CHF_2$ | |
| 1337 | i-$C_3H_7$ | S | H | 2-$CH_3$-4-$OCH_2CF_2CHF_2$ | |
| 1338 | i-$C_3H_7$ | S | 3-Cl | 2-$CH_3$-4-$CF_2CF_3$ | |
| 1339 | i-$C_3H_7$ | S | H | 2-$CH_3$-4-$CF(CF_3)_2$ | |
| 1340 | i-$C_3H_7$ | S | 3-I | 2-$CH_3$-4-$CF(CF_3)_2$ | |
| 1341 | i-$C_3H_7$ | S | H | 2-$CH_3$-4-$SO_2CH_2CF_2CHF_2$ | |
| 1342 | i-$C_3H_7$ | S | H | 2-Cl-4-$CF(CF_2)_2$ | |
| 1343 | i-$C_3H_7$ | S | H | 2-Cl-4-$CF_2CF_3$ | |
| 1344 | i-$C_3H_7$ | S | H | 2-$C_2H_5$-4-$CF(CF_3)_2$ | |
| 1345 | i-$C_3H_7$ | S | H | 2-F-4-$CF_2CF_3$ | |
| 1346 | i-$C_3H_7$ | $NCH_3$ | 3-I | 2-$CH_3$-4-$CF_2CF_3$ | |
| 1347 | i-$C_3H_7$ | $NCH_3$ | 3-I | 2-$CH_3$-4-$CF(CF_3)_2$ | |
| 1348 | i-$C_3H_7$ | $NCH_3$ | H | 2-$CH_3$-4-$CF_2CF_3$ | |
| 1349 | i-$C_3H_7$ | $NCH_3$ | H | 2-$CH_3$-4-$CF(CF_3)_2$ | |
| 1350 | i-$C_3H_7$ | NPh | H | 2-$CH_3$-4-$CF_2CF_3$ | |
| 1351 | i-$C_3H_7$ | NPh | 3-I | 2-$CH_3$-4-$CF(CF_3)_2$ | |
| 1352 | i-$C_3H_7$ | NPh | H | 2-Cl-4-$CF_2CF_3$ | |
| 1352 | $CH(CH_3)CH_2SCH_3$ | S | H | 2-$CH_3$-4-$CF_2CF_3$ | |
| 1353 | $CH(CH_3)CH_2SOCH_3$ | S | H | 2-$CH_3$-4-$CF_2CF_3$ | |
| 1354 | $CH(CH_3)CH_2SCH_3$ | S | H | 2-$CH_3$-4-$CF(CF_3)_2$ | |
| 1355 | $CH(CH_3)CH_2SOC_2H_5$ | S | H | 2-$CH_3$-4-$CF_2CF_3$ | |
| 1356 | $CH(CH_3)CH_2SC_2H_5$ | S | H | 2-$CH_3$-4-$CF(CF_3)_2$ | |
| 1357 | $C(CH_3)_2CH_2SC_2H_5$ | S | H | 2-$CH_3$-4-$CF_2CF_3$ | |
| 1358 | $C(CH_3)_2CH_2SOC_2H_5$ | S | H | 2-$CH_3$-4-$CF(CF_3)_2$ | |
| 1359 | $CH(CH_3)CH_2NHAc$ | S | H | 2-$CH_3$-4-$CF_2CF_3$ | |
| 1360 | $CH(CH_3)CH_2NHAc$ | S | H | 2-$CH_3$-4-$CF(CF_3)_2$ | |
| 1361 | $C(CH_3)_2CH_2NHAc$ | S | H | 2-$CH_3$-4-$CF_2CF_3$ | |
| 1362 | $C(CH_3)_2CH_2NHAc$ | S | H | 2-$CH_3$-4-$CF(CF_3)_2$ | |
| 1363 | $CH(CH_3)C_2H_4OCH_3$ | S | H | 2-$CH_3$-4-$CF_2CF_3$ | |
| 1364 | $CH(CH_3)C_2H_4OCH_3$ | S | H | 2-$CH_3$-4-$CF(CF_3)_2$ | |

TABLE 26

($Z^1 = Z^2 = O, R^2 = R^3 = H$, Het = Q15, $B^1 = B^2 = B^3 = B^4 = C$)

| No | R$^1$ | W | Xn | Ym | Physical property m.p. ° C. |
|---|---|---|---|---|---|
| 1365 | i-C$_3$H$_7$ | O | H | 2-CH$_3$-4-CF$_3$ | |
| 1366 | i-C$_3$H$_7$ | O | 5-CH$_3$ | 4-OCF$_3$ | |
| 1367 | i-C$_3$H$_7$ | O | H | 2-CH$_3$-4-OCF$_2$CHF$_2$ | |
| 1368 | i-C$_3$H$_7$ | S | H | 2-CH$_3$-4-OCH$_2$CF$_2$CHF$_2$ | |
| 1369 | i-C$_3$H$_7$ | S | 5-Cl | 2-CH$_3$-4-CF$_2$CF$_3$ | |
| 1370 | i-C$_3$H$_7$ | S | H | 2-CH$_3$-4-CF(CF$_3$)$_2$ | |
| 1371 | i-C$_3$H$_7$ | S | 5-I | 2-CH$_3$-4-CF(CF$_3$)$_2$ | |
| 1372 | i-C$_3$H$_7$ | S | H | 2-CH$_3$-4-SO$_2$CH$_2$CF$_2$CHF$_2$ | |
| 1373 | i-C$_3$H$_7$ | S | H | 2-Cl-4-CF(CF$_2$)$_2$ | |
| 1374 | i-C$_3$H$_7$ | S | H | 2-Cl-4-CF$_2$CF$_3$ | |
| 1375 | i-C$_3$H$_7$ | S | H | 2-C$_2$H$_5$-4-CF(CF$_3$)$_2$ | |
| 1376 | i-C$_3$H$_7$ | S | H | 2-F-4-CF$_2$CF$_3$ | |
| 1377 | i-C$_3$H$_7$ | NCH$_3$ | 5-I | 2-CH$_3$-4-CF$_2$CF$_3$ | |
| 1378 | i-C$_3$H$_7$ | NCH$_3$ | 5-I | 2-CH$_3$-4-CF(CF$_3$)$_2$ | |
| 1379 | i-C$_3$H$_7$ | NCH$_3$ | H | 2-CH$_3$-4-CF$_2$CF$_3$ | |
| 1380 | i-C$_3$H$_7$ | NCH$_3$ | 5-Br | 2-CH$_3$-4-CF(CF$_3$)$_2$ | 134–136 |
| 1381 | i-C$_3$H$_7$ | NPh | H | 2-CH$_3$-4-CF$_2$CF$_3$ | |
| 1382 | i-C$_3$H$_7$ | NPh | 5-Br | 2-CH$_3$-4-CF(CF$_3$)$_2$ | 164–166 |
| 1383 | i-C$_3$H$_7$ | NPh | H | 2-Cl-4-CF$_2$CF$_3$ | |
| 1384 | CH(CH$_3$)CH$_2$SCH$_3$ | O | H | 2-CH$_3$-4-CF$_2$CF$_3$ | |
| 1385 | CH(CH$_3$)CH$_2$SOCH$_3$ | O | H | 2-CH$_3$-4-CF$_2$CF$_3$ | |
| 1386 | CH(CH$_3$)CH$_2$SCH$_3$ | O | H | 2-CH$_3$-4-CF(CF$_3$)$_2$ | |
| 1387 | CH(CH$_3$)CH$_2$SOC$_2$H$_5$ | O | H | 2-CH$_3$-4-CF$_2$CF$_3$ | |
| 1388 | CH(CH$_3$)CH$_2$SC$_2$H$_5$ | O | H | 2-CH$_3$-4-CF(CF$_3$)$_2$ | |
| 1389 | C(CH$_3$)$_2$CH$_2$SC$_2$H$_5$ | O | H | 2-CH$_3$-4-CF$_2$CF$_3$ | |
| 1390 | C(CH$_3$)$_2$CH$_2$SOC$_2$H$_5$ | S | H | 2-CH$_3$-4-CF(CF$_3$)$_2$ | |
| 1391 | CH(CH$_3$)CH$_2$NHAc | S | H | 2-CH$_3$-4-CF$_2$CF$_3$ | |
| 1392 | CH(CH$_3$)CH$_2$NHAc | S | H | 2-CH$_3$-4-CF(CF$_3$)$_2$ | |
| 1393 | C(CH$_3$)$_2$CH$_2$NHAc | S | H | 2-CH$_3$-4-CF$_2$CF$_3$ | |
| 1394 | C(CH$_3$)$_2$CH$_2$NHAc | S | H | 2-CH$_3$-4-CF(CF$_3$)$_2$ | |
| 1395 | CH(CH$_3$)C$_2$H$_4$OCH$_3$ | S | H | 2-CH$_3$-4-CF$_2$CF$_3$ | |
| 1396 | CH(CH$_3$)C$_2$H$_4$OCH$_3$ | S | H | 2-CH$_3$-4-CF(CF$_3$)$_2$ | |

TABLE 27

($Z^1 = Z^2 = O, R^2 = R^3 = H$, Het = Q16, $B^1 = B^2 = B^3 = B^4 = C$)

| No | R$^1$ | W | Xn | Ym | Physical property m.p. ° C. |
|---|---|---|---|---|---|
| 1397 | i-C$_3$H$_7$ | O | H | 2-CH$_3$-4-CF$_3$ | |
| 1398 | i-C$_3$H$_7$ | O | 5-CH$_3$ | 4-OCF$_3$ | |
| 1399 | i-C$_3$H$_7$ | O | H | 2-CH$_3$-4-OCF$_2$CHF$_2$ | |
| 1400 | i-C$_3$H$_7$ | S | H | 2-CH$_3$-4-OCH$_2$CF$_2$CHF$_2$ | |
| 1401 | i-C$_3$H$_7$ | S | 5-Cl | 2-CH$_3$-4-CF$_2$CF$_3$ | |
| 1402 | i-C$_3$H$_7$ | S | H | 2-CH$_3$-4-CF(CF$_3$)$_2$ | |
| 1403 | i-C$_3$H$_7$ | S | 5-I | 2-CH$_3$-4-CF(CF$_3$)$_2$ | |
| 1404 | i-C$_3$H$_7$ | S | H | 2-CH$_3$-4-SO$_2$CH$_2$CF$_2$CHF$_2$ | |
| 1405 | i-C$_3$H$_7$ | S | H | 2-Cl-4-CF(CF$_2$)$_2$ | |
| 1406 | i-C$_3$H$_7$ | S | H | 2-Cl-4-CF$_2$CF$_3$ | |
| 1407 | i-C$_3$H$_7$ | S | H | 2-C$_2$H$_5$-4-CF(CF$_3$)$_2$ | |
| 1408 | i-C$_3$H$_7$ | S | H | 2-F-4-CF$_2$CF$_3$ | |
| 1409 | i-C$_3$H$_7$ | NCH$_3$ | 5-I | 2-CH$_3$-4-CF$_2$CF$_3$ | |
| 1410 | i-C$_3$H$_7$ | NCH$_3$ | 5-I | 2-CH$_3$-4-CF(CF$_3$)$_2$ | |
| 1411 | i-C$_3$H$_7$ | NCH$_3$ | H | 2-CH$_3$-4-CF$_2$CF$_3$ | |
| 1412 | i-C$_3$H$_7$ | NCH$_3$ | 5-Br | 2-CH$_3$-4-CF(CF$_3$)$_2$ | 165–175 |
| 1413 | i-C$_3$H$_7$ | NPh | H | 2-CH$_3$-4-CF$_2$CF$_3$ | |
| 1414 | i-C$_3$H$_7$ | NPh | 5-Br | 2-CH$_3$-4-CF(CF$_3$)$_2$ | 167–169 |
| 1415 | i-C$_3$H$_7$ | NPh | H | 2-Cl-4-CF$_2$CF$_3$ | |
| 1416 | CH(CH$_3$)CH$_2$SCH$_3$ | O | H | 2-CH$_3$-4-CF$_2$CF$_3$ | |
| 1417 | CH(CH$_3$)CH$_2$SOCH$_3$ | O | H | 2-CH$_3$-4-CF$_2$CF$_3$ | |
| 1418 | CH(CH$_3$)CH$_2$SCH$_3$ | O | H | 2-CH$_3$-4-CF(CF$_3$)$_2$ | |
| 1419 | CH(CH$_3$)CH$_2$SOC$_2$H$_5$ | O | H | 2-CH$_3$-4-CF$_2$CF$_3$ | |
| 1420 | CH(CH$_3$)CH$_2$SC$_2$H$_5$ | O | H | 2-CH$_3$-4-CF(CF$_3$)$_2$ | |
| 1421 | C(CH$_3$)$_2$CH$_2$SC$_2$H$_5$ | O | H | 2-CH$_3$-4-CF$_2$CF$_3$ | |
| 1422 | C(CH$_3$)$_2$CH$_2$SOC$_2$H$_5$ | S | H | 2-CH$_3$-4-CF(CF$_3$)$_2$ | |

TABLE 27-continued ($Z^1 = Z^2 = O, R^2 = R^3 = H$, Het = Q16, $B^1 = B^2 = B^3 = B^4 = C$)

| No | $R^1$ | W | Xn | Ym | Physical property m.p. ° C. |
|---|---|---|---|---|---|
| 1422 | $CH(CH_3)CH_2NHAc$ | S | H | $2\text{-}CH_3\text{-}4\text{-}CF_2CF_3$ | |
| 1423 | $CH(CH_3)CH_2NHAc$ | S | H | $2\text{-}CH_3\text{-}4\text{-}CF(CF_3)_2$ | |
| 1424 | $C(CH_3)_2CH_2NHAc$ | S | H | $2\text{-}CH_3\text{-}4\text{-}CF_2CF_3$ | |
| 1425 | $C(CH_3)_2CH_2NHAc$ | S | H | $2\text{-}CH_3\text{-}4\text{-}CF(CF_3)_2$ | |
| 1426 | $CH(CH_3)C_2H_4OCH_3$ | S | H | $2\text{-}CH_3\text{-}4\text{-}CF_2CF_3$ | |
| 1427 | $CH(CH_3)C_2H_4OCH_3$ | S | H | $2\text{-}CH_3\text{-}4\text{-}CF(CF_3)_2$ | |

TABLE 28

($Z^1 = Z^2 = O, R^2 = R^3 = H$, Het = Q17, $B^1 = B^2 = B^3 = B^4 = C$)

| No | $R^1$ | W | Xn | Ym | Physical property m.p. ° C. |
|---|---|---|---|---|---|
| 1428 | $i\text{-}C_3H_7$ | O | H | $2\text{-}CH_3\text{-}4\text{-}CF_3$ | |
| 1429 | $i\text{-}C_3H_7$ | O | $3\text{-}CH_3$ | $4\text{-}OCF_3$ | 171–174 |
| 1430 | $i\text{-}C_3H_7$ | O | H | $2\text{-}CH_3\text{-}4\text{-}OCF_2CHF_2$ | |
| 1431 | $i\text{-}C_3H_7$ | S | H | $2\text{-}CH_3\text{-}4\text{-}OCH_2CF_2CHF_2$ | |
| 1432 | $i\text{-}C_3H_7$ | S | 3-Cl | $2\text{-}CH_3\text{-}4\text{-}CF_2CF_3$ | |
| 1433 | $i\text{-}C_3H_7$ | S | H | $2\text{-}CH_3\text{-}4\text{-}CF(CF_3)_2$ | |
| 1434 | $i\text{-}C_3H_7$ | S | 3-I | $2\text{-}CH_3\text{-}4\text{-}CF(CF_3)_2$ | |
| 1435 | $i\text{-}C_3H_7$ | S | H | $2\text{-}CH_3\text{-}4\text{-}SO_2CH_2CF_2CHF_2$ | |
| 1436 | $i\text{-}C_3H_7$ | S | H | $2\text{-}Cl\text{-}4\text{-}CF(CF_2)_2$ | |
| 1437 | $i\text{-}C_3H_7$ | S | H | $2\text{-}Cl\text{-}4\text{-}CF_2CF_3$ | |
| 1438 | $i\text{-}C_3H_7$ | S | H | $2\text{-}C_2H_5\text{-}4\text{-}CF(CF_3)_2$ | |
| 1439 | $i\text{-}C_3H_7$ | S | H | $2\text{-}F\text{-}4\text{-}CF_2CF_3$ | |
| 1440 | $i\text{-}C_3H_7$ | $NCH_3$ | 3-I | $2\text{-}CH_3\text{-}4\text{-}CF_2CF_3$ | |
| 1441 | $i\text{-}C_3H_7$ | $NCH_3$ | 3-I | $2\text{-}CH_3\text{-}4\text{-}CF(CF_3)_2$ | |
| 1442 | $i\text{-}C_3H_7$ | $NCH_3$ | H | $2\text{-}CH_3\text{-}4\text{-}CF_2CF_3$ | |
| 1443 | $i\text{-}C_3H_7$ | $NCH_3$ | 3-Br | $2\text{-}CH_3\text{-}4\text{-}CF(CF_3)_2$ | |
| 1444 | $i\text{-}C_3H_7$ | NPh | H | $2\text{-}CH_3\text{-}4\text{-}CF_2CF_3$ | |
| 1445 | $i\text{-}C_3H_7$ | NPh | 3-Br | $2\text{-}CH_3\text{-}4\text{-}CF(CF_3)_2$ | |
| 1446 | $i\text{-}C_3H_7$ | NPh | H | $2\text{-}Cl\text{-}4\text{-}CF_2CF_3$ | |
| 1447 | $CH(CH_3)CH_2SCH_3$ | O | H | $2\text{-}CH_3\text{-}4\text{-}CF_2CF_3$ | |
| 1448 | $CH(CH_3)CH_2SOCH_3$ | O | H | $2\text{-}CH_3\text{-}4\text{-}CF_2CF_3$ | |
| 1449 | $CH(CH_3)CH_2SCH_3$ | O | H | $2\text{-}CH_3\text{-}4\text{-}CF(CF_3)_2$ | |
| 1450 | $CH(CH_3)CH_2SOC_2H_5$ | O | H | $2\text{-}CH_3\text{-}4\text{-}CF_2CF_3$ | |
| 1451 | $CH(CH_3)CH_2SC_2H_5$ | O | H | $2\text{-}CH_3\text{-}4\text{-}CF(CF_3)_2$ | |
| 1452 | $C(CH_3)_2CH_2SC_2H_5$ | O | H | $2\text{-}CH_3\text{-}4\text{-}CF_2CF_3$ | |
| 1453 | $C(CH_3)_2CH_2SOC_2H_5$ | S | H | $2\text{-}CH_3\text{-}4\text{-}CF(CF_3)_2$ | |
| 1454 | $CH(CH_3)CH_2NHAc$ | S | H | $2\text{-}CH_3\text{-}4\text{-}CF_2CF_3$ | |
| 1455 | $CH(CH_3)CH_2NHAc$ | S | H | $2\text{-}CH_3\text{-}4\text{-}CF(CF_3)_2$ | |
| 1456 | $C(CH_3)_2CH_2NHAc$ | S | H | $2\text{-}CH_3\text{-}4\text{-}CF_2CF_3$ | |
| 1457 | $C(CH_3)_2CH_2NHAc$ | S | H | $2\text{-}CH_3\text{-}4\text{-}CF(CF_3)_2$ | |
| 1458 | $CH(CH_3)C_2H_4OCH_3$ | S | H | $2\text{-}CH_3\text{-}4\text{-}CF_2CF_3$ | |
| 1459 | $CH(CH_3)C_2H_4OCH_3$ | S | H | $2\text{-}CH_3\text{-}4\text{-}CF(CF_3)_2$ | |

TABLE 29

($Z^1 = Z^2 = O, R^2 = R^3 = H$, Het = Q18, $B^1 = B^2 = B^3 = B^4 = C$)

| No | $R^1$ | W | Xn | Ym | Physical property m.p. ° C. |
|---|---|---|---|---|---|
| 1460 | $i\text{-}C_3H_7$ | O | H | $2\text{-}CH_3\text{-}4\text{-}CF_3$ | |
| 1461 | $i\text{-}C_3H_7$ | O | H | $4\text{-}OCF_3$ | |
| 1462 | $i\text{-}C_3H_7$ | O | H | $2\text{-}CH_3\text{-}4\text{-}OCF_2CHF_2$ | |
| 1463 | $i\text{-}C_3H_7$ | S | H | $2\text{-}CH_3\text{-}4\text{-}OCH_2CF_2CHF_2$ | |
| 1464 | $i\text{-}C_3H_7$ | S | 2-Cl | $2\text{-}CH_3\text{-}4\text{-}CF_2CF_3$ | |
| 1465 | $i\text{-}C_3H_7$ | S | H | $2\text{-}CH_3\text{-}4\text{-}CF(CF_3)_2$ | |

TABLE 29-continued ($Z^1 = Z^2 = O$, $R^2 = R^3 = H$, Het = Q18, $B^1 = B^2 = B^3 = B^4 = C$)

| No | $R^1$ | W | Xn | Ym | Physical property m.p. °C. |
|---|---|---|---|---|---|
| 1466 | i-$C_3H_7$ | S | 2-I | 2-$CH_3$-4-$CF(CF_3)_2$ | |
| 1467 | i-$C_3H_7$ | S | H | 2-$CH_3$-4-$SO_2CH_2CF_2CHF_2$ | |
| 1468 | i-$C_3H_7$ | S | H | 2-Cl-4-$CF(CF_2)_2$ | |
| 1469 | i-$C_3H_7$ | S | H | 2-Cl-4-$CF_2CF_3$ | |
| 1470 | i-$C_3H_7$ | S | H | 2-$C_2H_5$-4-$CF(CF_3)_2$ | |
| 1471 | i-$C_3H_7$ | S | H | 2-F-4-$CF_2CF_3$ | |
| 1472 | i-$C_3H_7$ | $NCHF_2$ | 2-I | 2-$CH_3$-4-$CF_2CF_3$ | |
| 1473 | i-$C_3H_7$ | $NCHF_2$ | H | 2-$CH_3$-4-$CF(CF_3)_2$ | 85–95 |
| 1474 | i-$C_3H_7$ | $NCH_3$ | H | 2-$CH_3$-4-$CF_2CF_3$ | |
| 1475 | i-$C_3H_7$ | $NCH_3$ | 2-Br | 2-$CH_3$-4-$CF(CF_3)_2$ | |
| 1476 | i-$C_3H_7$ | NPh | H | 2-$CH_3$-4-$CF_2CF_3$ | |
| 1477 | i-$C_3H_7$ | NPh | 2-Br | 2-$CH_3$-4-$CF(CF_3)_2$ | |
| 1478 | i-$C_3H_7$ | NPh | H | 2-Cl-4-$CF_2CF_3$ | |
| 1479 | $CH(CH_3)CH_2SCH_3$ | O | H | 2-$CH_3$-4-$CF_2CF_3$ | |
| 1480 | $CH(CH_3)CH_2SOCH_3$ | O | H | 2-$CH_3$-4-$CF_2CF_3$ | |
| 1481 | $CH(CH_3)CH_2SCH_3$ | O | H | 2-$CH_3$-4-$CF(CF_3)_2$ | |
| 1482 | $CH(CH_3)CH_2SOC_2H_5$ | O | H | 2-$CH_3$-4-$CF_2CF_3$ | |
| 1483 | $CH(CH_3)CH_2SC_2H_5$ | O | H | 2-$CH_3$-4-$CF(CF_3)_2$ | |
| 1484 | $C(CH_3)_2CH_2SC_2H_5$ | O | H | 2-$CH_3$-4-$CF_2CF_3$ | |
| 1485 | $C(CH_3)_2CH_2SOC_2H_5$ | S | H | 2-$CH_3$-4-$CF(CF_3)_2$ | |
| 1486 | $CH(CH_3)CH_2NHAc$ | S | H | 2-$CH_3$-4-$CF_2CF_3$ | |
| 1487 | $CH(CH_3)CH_2NHAc$ | S | H | 2-$CH_3$-4-$CF(CF_3)_2$ | |
| 1488 | $C(CH_3)_2CH_2NHAc$ | S | H | 2-$CH_3$-4-$CF_2CF_3$ | |
| 1489 | $C(CH_3)_2CH_2NHAc$ | S | H | 2-$CH_3$-4-$CF(CF_3)_2$ | |
| 1490 | $CH(CH_3)C_2H_4OCH_3$ | S | H | 2-$CH_3$-4-$CF_2CF_3$ | |
| 1491 | $CH(CH_3)C_2H_4OCH_3$ | S | H | 2-$CH_3$-4-$CF(CF_3)_2$ | |

TABLE 30

($Z^1 = Z^2 = O$, $R^2 = R^3 = H$, Het = Q19, $B^1 = B^2 = B^3 = B^4 = C$)

| No | $R^1$ | W | Xn | Ym | Physical property m.p. °C. |
|---|---|---|---|---|---|
| 1492 | i-$C_3H_7$ | O | H | 2-$CH_3$-4-$CF_3$ | |
| 1493 | i-$C_3H_7$ | O | H | 4-$OCF_3$ | |
| 1494 | i-$C_3H_7$ | O | H | 2-$CH_3$-4-$OCF_2CHF_2$ | |
| 1495 | i-$C_3H_7$ | S | H | 2-$CH_3$-4-$OCH_2CF_2CHF_2$ | |
| 1496 | i-$C_3H_7$ | S | 2-Cl | 2-$CH_3$-4-$CF_2CF_3$ | |
| 1497 | i-$C_3H_7$ | S | H | 2-$CH_3$-4-$CF(CF_3)_2$ | |
| 1498 | i-$C_3H_7$ | S | 2-I | 2-$CH_3$-4-$CF(CF_3)_2$ | |
| 1499 | i-$C_3H_7$ | S | H | 2-$CH_3$-4-$SO_2CH_2CF_2CHF_2$ | |
| 1500 | i-$C_3H_7$ | S | H | 2-Cl-4-$CF(CF_2)_2$ | |
| 1501 | i-$C_3H_7$ | S | H | 2-Cl-4-$CF_2CF_3$ | |
| 1502 | i-$C_3H_7$ | S | H | 2-$C_2H_5$-4-$CF(CF_3)_2$ | |
| 1503 | i-$C_3H_7$ | S | H | 2-F-4-$CF_2CF_3$ | |
| 1504 | i-$C_3H_7$ | $NCHF_2$ | 2-I | 2-$CH_3$-4-$CF_2CF_3$ | |
| 1505 | i-$C_3H_7$ | $NCHF_2$ | H | 2-$CH_3$-4-$CF(CF_3)_2$ | 70–90 |
| 1506 | i-$C_3H_7$ | $NCH_3$ | H | 2-$CH_3$-4-$CF_2CF_3$ | |
| 1507 | i-$C_3H_7$ | $NCH_3$ | 2-Br | 2-$CH_3$-4-$CF(CF_3)_2$ | |
| 1508 | i-$C_3H_7$ | NPh | H | 2-$CH_3$-4-$CF_2CF_3$ | |
| 1509 | i-$C_3H_7$ | NPh | 2-Br | 2-$CH_3$-4-$CF(CF_3)_2$ | |
| 1510 | i-$C_3H_7$ | NPh | H | 2-Cl-4-$CF_2CF_3$ | |
| 1511 | $CH(CH_3)CH_2SCH_3$ | O | H | 2-$CH_3$-4-$CF_2CF_3$ | |
| 1512 | $CH(CH_3)CH_2SOCH_3$ | O | H | 2-$CH_3$-4-$CF_2CF_3$ | |
| 1513 | $CH(CH_3)CH_2SCH_3$ | O | H | 2-$CH_3$-4-$CF(CF_3)_2$ | |
| 1514 | $CH(CH_3)CH_2SOC_2H_5$ | O | H | 2-$CH_3$-4-$CF_2CF_3$ | |
| 1515 | $CH(CH_3)CH_2SC_2H_5$ | O | H | 2-$CH_3$-4-$CF(CF_3)_2$ | |
| 1516 | $C(CH_3)_2CH_2SC_2H_5$ | O | H | 2-$CH_3$-4-$CF_2CF_3$ | |
| 1517 | $C(CH_3)_2CH_2SOC_2H_5$ | S | H | 2-$CH_3$-4-$CF(CF_3)_2$ | |
| 1518 | $CH(CH_3)CH_2NHAc$ | S | H | 2-$CH_3$-4-$CF_2CF_3$ | |
| 1519 | $CH(CH_3)CH_2NHAc$ | S | H | 2-$CH_3$-4-$CF(CF_3)_2$ | |
| 1520 | $C(CH_3)_2CH_2NHAc$ | S | H | 2-$CH_3$-4-$CF_2CF_3$ | |
| 1521 | $C(CH_3)_2CH_2NHAc$ | S | H | 2-$CH_3$-4-$CF(CF_3)_2$ | |
| 1522 | $CH(CH_3)C_2H_4OCH_3$ | S | H | 2-$CH_3$-4-$CF_2CF_3$ | |
| 1523 | $CH(CH_3)C_2H_4OCH_3$ | S | H | 2-$CH_3$-4-$CF(CF_3)_2$ | |

TABLE 31

($Z^1 = Z^2 = O$, $R^2 = R^3 = H$, $B^1 = B^2 = B^3 = B^4 = C$)

| No | $R^1$ | W | Het | Ym | Physical property m.p. ° C. |
|---|---|---|---|---|---|
| 1524 | i-$C_3H_7$ | O | Q20 | 2-$CH_3$-4-$CF_2CF_3$ | |
| 1525 | i-$C_3H_7$ | O | Q20 | 2-$CH_3$-4-$CF(CF_3)_2$ | |
| 1526 | i-$C_3H_7$ | S | Q20 | 2-$CH_3$-4-$CF_2CF_3$ | |
| 1527 | i-$C_3H_7$ | S | Q20 | 2-$CH_3$-4-$CF(CF_3)_2$ | |
| 1528 | i-$C_3H_7$ | $NCH_3$ | Q20 | 2-$CH_3$-4-$CF_2CF_3$ | |
| 1529 | i-$C_3H_7$ | $NCH_3$ | Q20 | 2-$CH_3$-4-$CF(CF_3)_2$ | |
| 1530 | i-$C_3H_7$ | NPh | Q20 | 2-$CH_3$-4-$CF_2CF_3$ | |
| 1531 | i-$C_3H_7$ | NPh | Q20 | 2-$CH_3$-4-$CF(CF_3)_2$ | |
| 1532 | i-$C_3H_7$ | O | Q21 | 2-$CH_3$-4-$CF_2CF_3$ | |
| 1533 | i-$C_3H_7$ | O | Q21 | 2-$CH_3$-4-$CF(CF_3)_2$ | |
| 1534 | i-$C_3H_7$ | S | Q21 | 2-$CH_3$-4-$CF_2CF_3$ | |
| 1535 | i-$C_3H_7$ | S | Q21 | 2-$CH_3$-4-$CF(CF_3)_2$ | |
| 1536 | i-$C_3H_7$ | $NCH_3$ | Q21 | 2-$CH_3$-4-$CF_2CF_3$ | |
| 1537 | i-$C_3H_7$ | $NCH_3$ | Q21 | 2-$CH_3$-4-$CF(CF_3)_2$ | |
| 1538 | i-$C_3H_7$ | NPh | Q21 | 2-$CH_3$-4-$CF_2CF_3$ | |
| 1539 | i-$C_3H_7$ | NPh | Q21 | 2-$CH_3$-4-$CF(CF_3)_2$ | |
| 1540 | i-$C_3H_7$ | O | Q22 | 2-$CH_3$-4-$CF_2CF_3$ | |
| 1541 | i-$C_3H_7$ | O | Q22 | 2-$CH_3$-4-$CF(CF_3)_2$ | |
| 1542 | i-$C_3H_7$ | S | Q22 | 2-$CH_3$-4-$CF_2CF_3$ | |
| 1543 | i-$C_3H_7$ | S | Q22 | 2-$CH_3$-4-$CF(CF_3)_2$ | |
| 1544 | i-$C_3H_7$ | $NCH_3$ | Q22 | 2-$CH_3$-4-$CF_2CF_3$ | |
| 1545 | i-$C_3H_7$ | $NCH_3$ | Q22 | 2-$CH_3$-4-$CF(CF_3)_2$ | |
| 1546 | i-$C_3H_7$ | NPh | Q22 | 2-$CH_3$-4-$CF_2CF_3$ | |
| 1547 | i-$C_3H_7$ | NPh | Q22 | 2-$CH_3$-4-$CF(CF_3)_2$ | |

TABLE 32

($Z^1 = Z^2 = O$, $R^2 = R^3 = H$, Het = Q2, p = 0, $B^1 = B^4 = C$)

| No | $R^1$ | Xn | $B^2$ | $B^3$ | Ym | Physical property m.p. ° C. |
|---|---|---|---|---|---|---|
| 1548 | i-$C_3H_7$ | H | N | C | 2-$CH_3$-4-$OCH(CF_3)_2$ | 259–260 |
| 1549 | $C(CH_3)_2CH_2SCH_3$ | H | N | C | 2-$CH_3$-4-$OCH(CF_3)_2$ | 202–203 |
| 1550 | $C(CH_3)_2CH_2SCH_3$ | 5-Cl | N | C | 2-$CH_3$-4-$CF(CF_3)_2$ | |
| 1551 | i-$C_3H_7$ | H | N | N | 2-$CH_3$-4-$CF(CF_3)_2$ | |
| 1552 | i-$C_3H_7$ | 5-Cl | C | N | 2-$CH_3$-4-$CF_2CF_3$ | |
| 1553 | i-$C_3H_7$ | 5-I | C | N | 4-$OCH(CF_3)_2$ | |
| 1554 | $CH(CH_3)CH_2SCH_3$ | H | N | N | 4-$OCHF_2$ | |
| 1555 | $C(CH_3)_2CH_2SOCH_3$ | H | N | C | 2-$CH_3$-4-$OCF_3$ | |
| 1556 | $CH(CH_3)CH(CH_3)SCH_3$ | H | N | C | 2-$CH_3$-4-$CF_2CF_3$ | |

TABLE 33

($Z^1 = Z^2 = O$, $R^2 = R^3 = H$, Het = Q3, p = 0, $B^1 = B^4 = C$)

| No | $R^1$ | Xn | $B^2$ | $B^3$ | Ym | Physical property m.p. ° C. |
|---|---|---|---|---|---|---|
| 1557 | i-$C_3H_7$ | H | N | C | 2-$CH_3$-4-$OCH(CF_3)_2$ | |
| 1558 | $C(CH_3)_2CH_2SCH_3$ | H | N | C | 2-$CH_3$-4-$OCH(CF_3)_2$ | |
| 1559 | $C(CH_3)_2CH_2SCH_3$ | 2-Cl | N | C | 2-$CH_3$-4-$CF(CF_3)_2$ | |
| 1560 | i-$C_3H_7$ | H | N | N | 2-$CH_3$-4-$CF(CF_3)_2$ | |
| 1561 | i-$C_3H_7$ | 2-Cl | C | N | 2-$CH_3$-4-$CF_2CF_3$ | |
| 1562 | i-$C_3H_7$ | 2-I | C | N | 4-$OCH(CF_3)_2$ | |
| 1563 | $CH(CH_3)CH_2SCH_3$ | H | N | N | 4-$OCHF_2$ | |
| 1564 | $C(CH_3)_2CH_2SOCH_3$ | H | N | C | 2-$CH_3$-4-$OCF_3$ | |
| 1565 | $CH(CH_3)CH(CH_3)SCH_3$ | H | N | C | 2-$CH_3$-4-$CF_2CF_3$ | |

In the Tables 1 to 33, "Ac" means acetyl group, "Ph" means phenyl group and "c-" means alicyclic hydrocarbon group.

The agricultural and horticultural insecticides containing the heterocyclic dicarboxylic acid diamide derivative of formula (I) of the present invention as an active ingredient are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophes orana fasciata*), smaller tea tortrix (*Adoxophyes sp.*), Manchurian fruit moth (*Grapholita inopinata*), oriental fruit moth (*Grapholita molesta*) soybean pod border (*Leguminovora glycinivorella*), mulberry leafroller (*Olethreutes mori*), tea leafroller (*Caloptilia thevivora*), Caloptilia sp. (*Caloptilia zachrysa*), apple leafminer (*Phyllonorvcter ringoniella*), pear barkminer (*Spulerrina astaurota*), common white (*Piers rapae crucivora*), tobacco budworm (Heliothis sp.), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*) rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticepts*), brown rice planthopper (*Nilaparvata lugens*), whitebacked rice planthopper (*Sogatella furcifera*), citrus psylla (*Diaphorina citri*), grape whitefly (*Aleurolibus taonabae*), sweetpotato whitefly (*Bemisia tabaci*), greenhouse whitefly (*Trialeurodes vaporariorum*), turnup aphid (*Lipaphis erysimi*), green peach aphid (*Myzus persicae*), Indian wax scale (*Ceroplastes ceriferus*), cottony citrus scale (*Pulvinaria aurantii*) camphor scale (*Pseudaonidia duplex*), san Jose scale (*Comstockaspis perniciosa*), arrowhead scale (*Unapsis yanonensis*) etc.; TYLENCHIDA including soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*) pine shoot beetle (*Tomicus piniperda*), Colorado potato beetle (*Leptinotarsa decemlineata*), Mexican bean beetle (*Epilachna varivestis*), corn rootworm (Diabrotica sp.), etc.; DIPTERA including (*Dacus(Zeugodacus) cucurbitae*), oriental fruit fly (*Dacus (Bactrocera) dorsalis*) rice leafminer (*Agnomyza oryzae*), onion maggot (*Delia antiqua*), seedcorn maggot (*Delia platura*), soybean pod gall midge (*Asphondylia sp.*), muscid fly (*Musca domestica*), house mosquito (*Culex pipiens pipiens*), etc.; and TYLENCHIDA including coffee root-lesion nematode (*Pratylenchus coffeae*), potato cyst nematode (*Globodera rostochiensis*), root-knot nematode (*Meloidogyne sp.*), citrus nematode (*Tylenchulus semipenetrans*), Aphelenchus sp. (*Aphelenchus avenae*), chrysanthemum foliar (*Aphelenchoides ritzemabosi*), etc.

The agricultural and horticultural insecticide containing the heterocyclic dicarboxylic acid diamide derivative represented by formula (I) of the present invention has a marked controlling effect on the above-exemplified insect pests, sanitary pests and/or nematodes, which are injurious to paddy field crops, upland crops, fruit trees, vegetables and other crops, flowers and ornament plants, and the like. Therefore, the desired effect of the agrohorticultural insecticide of the present invention can be exhibited by applying the insecticide to the paddy field water, stalks and leaves or soil of paddy field, upland field, fruit trees, vegetables, other crops or flowers and ornament plants at a season at which the insect pests, sanitary pests or nematodes are expected to appear, before their appearance or at the time when their appearance is confirmed.

In general, the agricultural and horticultural insecticide of the present invention is used after being prepared into conveniently usable forms according to ordinary manner for preparation of agrochemicals.

That is, the heterocyclic dicarboxylic acid diamide derivative of formula (I) and an appropriate carrier are blended optionally together with an adjuvant in a proper proportion and prepared into a suitable preparation form such as suspension, emulsifiable concentrate, soluble concentrate, wettable powder, granules, dust or tablets through dissolution, separation, suspension, mixing, impregnation, adsorption or sticking.

The inert carrier used in the present invention may be either solid or liquid. As the solid carrier, soybean flour, cereal flour, wood flour, bark flour, saw dust, powdered tobacco stalks, powdered walnut shells, bran, powdered cellulose, extraction residues of vegetables, powdered synthetic polymers or resins, clay (e.g. kaolin, bentonite and acid clay), talc (e.g. talc and pyrophyllite), silica materials (e.g. diatomaceous earth, siliceous sand, mica, white carbon, i.e. synthetic high-dispersion silicic acid, also called finely divided hydrated silica or hydrated silicic acid, some of the commercially available products contain calcium silicate as the major component), activated carbon, powdered sulfur, pumice, calcined diatomaceous earth, ground brick, fly ash, sand, calcium carbonate, calcium phosphate and other inorganic or mineral powders, chemical fertilizers such as ammonium sulfate, ammonium phosphate, ammonium nitrate, urea, ammonium chloride and the like, and compost. These carriers may be used either alone or as a mixture of two or more carriers.

The liquid carrier is that which itself has a solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, cellosolve, dipropyl ether and tetrahydrofuran; aliphatic hydrocarbons such as kerosene and mineral oil; aromatic hydrocarbons such as benzene, toluene, xylene, solvent naphtha and alkylnaphthalene; halogenated hydrocarbons such as dichlorethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination of two or more adjuvants in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty,acid esters, polyoxyethylene resinates, polyoxyethylene sorbitan monolaurate, polyoxyethylene sorbitan monooleate, alkylarylsulfonates, naphthalene-sulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicone oil may also be used as a defoaming agent.

The content of the active ingredient may be varied according to the need. In dusts or granules, the suitable content thereof is from 0.01 to 50% by weight. In emulsifiable concentrate and flowable wettable powder, too, the suitable content is from 0.01 to 50% by weight.

The agricultural and horticultural insecticide of the present invention is used to control a variety of insect pests in the following manner. That is, it is applied to a crop on which the insect pests are expected to appear or a site where appearance of the insect pests is undesirable, as it is or after being properly diluted with or suspended in water or the like, in an amount effective for control of the insect pests.

The applying dosage of the agrihorticultural insecticide of the present invention is varied depending upon various factors such as a purpose, insect pests to be controlled, a growth state of a plant, tendency of insect pests appearance, weather, environmental conditions, a preparation form, an application method, an application site and an application time. It may be properly chosen in a range of 0.1 g to 10 kg (in terms of active ingredient compound) per 10 are depending upon purposes.

The agricultural and horticultural insecticide of the present invention may be used in admixture with other agricultural and horticultural disease or pest controllers in order to expand both spectrum of controllable diseases and insect pest species and the period of time when effective applications are possible or to reduce the dosage.

EXAMPLES

Typical examples of the present invention are described below, but they should not be construed as limiting the scope of the invention.

Example 1

(1-1). Production of N-[4-(heptafluoro-2-propyl)-2-methylphenyl]pyridine-3,4-dicarboximide In 10 ml of THF were dissolved 1.50 g of pyridine-3,4-dicarboxylic acid anhydride and 2.75 g of 4-(heptafluoro-2-propyl)-2-methylaniline, and the reaction was carried out at room temperature for 3 hours. After completion of the reaction, the solvent was distilled off under reduced pressure and 20 ml of trifluoroacetic anhydride was added to the resulting residue, and the reaction was carried out with refluxing for 3 hours. After completion of the reaction, the solvent was distilled off under reduced pressure to obtain crude N-[4-(heptafluoro-2-propyl)-2-methylphenyl] pyridine-3,4-dicarboximide quantitatively.

(1-2). Production of 3-[4-(heptafluoro-2-propyl)-2-methylphenyl]aminocarbonyl-4-pyridinecarboxylic acid-2-propylamide (Compound No. 230) and 4-[4-(heptafluoro-2-propyl)-2-methylphenyl]aminocarbonyl-3-pyridinecarboxylic acid-2-propylamide (Compound No. 512)

In 10 ml of dioxane was dissolved 4.1 g of N-[4-(heptafluoro-2-propyl)-2-methylphenyl]pyridine-3,4-dicarboximide, followed by adding thereto 0.8 g of isopropylamine, and the reaction was carried out at room temperature for 8 hours. After completion of the reaction, the solvent was distilled off under reduced pressure and the resulting residue was purified by a silica gel column chromatography using a 2:1 mixed solvent of hexane and ethyl acetate as an eluent, to obtain 2.1 g of (compound No. 230) and 1.8 g of (compound No. 512) as white crystals.

| Physical property: | | |
|---|---|---|
| compound No. 230 | m.p. 234–236° C. | Yield 45%. |
| compound No. 512 | m.p. 206–208° C. | Yield 39%. |

Example 2

(2-1). Production of 5-bromo-3-[4-(heptafluoro-2-propyl)-2-methylphenyl]aminocarbonyl-1-phenyl-4-pyrazolecarboxylic acid 2-propylamide (Compound No. 1382) and 5-bromo-4-[4-(heptafluoro-2-propyl)-2-methylphenyl]-aminocarbonyl-1-phenyl-3-pyrazolecarboxylic acid 2-propylamide (Compound No. 1414)

In 10 ml of thionyl chloride was dissolved 500 mg of 5-bromo-1-phenyl-3,4-pyrazoledicarboxylic acid, and the reaction was carried out at reflux temperature for 2 hours. After completion of the reaction, the thionyl chloride was distilled off under reduced pressure to obtain a crude acid chloride. This compound was dissolved in 2 ml of THF and the resulting solution was added dropwise at 0° C. to a solution prepared by dissolving 420 mg of heptafluoro-2-propyl-2-methylaniline and 410 mg of triethylamine in 10 ml of THF. After completion of the dropwise addition, 470 mg of isopropylamine was added thereto at 0° C. and the reaction was carried out at room temperature for 2 hours. After completion of the reaction, the triethylamine hydrochloride was filtered off and the mother liquor was concentrated. The resulting residue was purified by a silica gel column chromatography using ethyl acetatein-hexane as an eluent, to obtain 360 mg of 5-bromo-3-[4-(heptafluoro-2-propyl)-2-methylphenyl]aminocarbonyl-1-phenyl-4-pyrazole-carboxylic acid 2-propylamide (compound No. 1382) and 360 mg of 5-bromo-4-[4-(heptafluoro-2-propyl)-2-methylphenyl]-aminocarbonyl-1-phenyl-3-pyrazole-carboxylic acid 2-propylamide (compound No. 1414) as white crystals.

Physical property:
compound No. 1382 m.p. 164–166. Yield 36%.
compound No. 1414 m.p. 167–169. Yield 36%.

Example 3

(3-1). Production of 2-chloro-4-[4-(heptafluoro-2-propyl)-2-methylphenyl]aminocarbonyl-3-pyridinecarboxylic acid In 20 ml of anhydrous THF was dissolved 2.78 g of diisopropylamine, and 18 ml of a solution of n-butyllithium in hexane (1.53 M) was added dropwise thereto at −78° C. under an argon atmosphere. The resulting mixture was stirred at −78° C. for 1 hour, and then a solution of 5.17 g of 2-chloro-4-pyridinecarboxylic acid 4-(heptafluoro-2-propyl)-2-methylanilide in 100 ml of THF was added dropwise thereto at −78° C. After completion of the dropwise addition, the stirring was continued at −78° C. for 2 hours and carbon dioxide gas was bubbled thereinto for 1 hour. Then, the resulting mixture was warmed to room temperature and 200 ml of 1N hydrochloric acid was added thereto, followed by extraction with ethyl acetate. The organic layer was dried over anhydrous magnesium sulfate and then distilled under reduced pressure to remove the solvent, whereby 4.70 g (yield: 82%) of the crude desired compound was obtained as an amorphous solid. This compound was used in a subsequent reaction without purification.

(3-2). Production of 2-chloro-4-[4-(heptafluoro-2-propyl)-2-methylphenyl]aminocarbonyl-3-pyridinecarboxylic acid 2-propylamide (Compound No. 524)

In 10 ml of t-butyl methyl ether was dissolved 500 mg of 2-chloro-4-[4-(heptafluoro-2-propyl)-2-methylphenyl]aminocarbonyl-3-pyridinecarboxylic acid, followed by adding thereto 340 mg of ok trifluoroacetic anhydride, and the resulting mixture was stirred at room temperature for 2 hours. After the disappearance of the starting material was confirmed by TLC, 330 mg of isopropylamine was added to the mixture, followed by stirring at room temperature for another 2 hours. After completion of the reaction, ethyl acetate was added and the reaction solution was washed successively with water, a saturated aqueous sodium hydrogencarbonate solution and a saturated aqueous sodium chloride solution, and dried over anhydrous magnesium sulfate. The solvent was distilled off under reduced pressure and the resulting residue was purified by a silica gel column chromatography using ethyl acetate/n-hexane as an eluent, to obtain 460 mg of the desired compound as white crystals.

Physical property: m.p. 275–277° C. Yield 84%.

Example 4

(4-1). Production of N-[4-(heptafluoro-2-propyl)-2-methylphenyl]pyridine-2,3-dicarboximide-1-oxide In 25 ml of chloroform was dissolved 3.1 g of N-[4-(heptafluoro-2-propyl)-2-methylphenyl]pyridine-2,3-dicarboximide, and 5.0 g of m-chloroperbenzoic acid was added thereto at room temperature. After the resulting mixture was stirred at room temperature for 3 hours, a saturated aqueous sodium hydrogencarbonate solution was added to the reaction solution, followed by extraction with ethyl acetate. The organic layer was washed successively with water, a saturated aqueous sodium hydrogencarbonate solution and a saturated aqueous sodium chloride solution, and dried over anhydrous magnesium sulfate. The solvent was distilled off under reduced pressure and the resulting residue was purified by a silica gel column chromatography using ethyl acetate/n-hexane as an eluent, to obtain 820 mg (yield: 84%) of the desired compound.

(4-2). Production of 3-[4-(heptafluoro-2-propyl)-2-methylphenyl]aminocarbonyl-2-(2-propyl)aminocarbonylpyridine-N-oxide (Compound No. 804)

In 10 ml of THF was dissolved 400 mg of N-[4-(heptafluoro-2-propyl)-2-methylphenyl]pyridine-2,3-dicarboximide-1-oxide, followed by adding thereto 200 mg of isopropylamine, and the resulting mixture was stirred at room temperature for 5 hours. After completion of the reaction, the solvent was distilled off under reduced pressure and the resulting residue was purified by a silica gel column chromatography using ethyl acetate/n-hexane as an eluent, to obtain 290 mg of the desired compound as white crystals.

Physical property: m.p. 108–110° C. Yield 63%.

Typical formulation examples and test examples of the present invention are described below but they should not be construed as limiting the scope of the invention.

In the formulation examples, parts are all by weight.

Formulation Example 1

| | |
|---|---|
| Each compound listed in Tables 1 to 33 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Tables 1 to 33 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Tables 1 to 33 | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Tables 1 to 33 | 20 parts |
| Kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal Effect on Diamondback Moth (*Plutella xylostella*)

Adult diamondback moths were released and allowed to oviposit on a Chinese cabbage seedling. Two days after the release, the seedling having eggs deposited thereon was immersed for about 30 seconds in a liquid chemical prepared by diluting a preparation containing each of the compounds listed in Tables 1 to 33 as an active ingredient to adjust the concentration to 500 ppm. After air-drying, the seedling was allowed to stand in a room thermostated at 25° C. Six days after the immersion in the liquid chemical, the hatched insects were counted and the mortality was calculated according to the following equation. The test was carried out with three replications of 10 insects.

$$\text{Corrected mortality (\%)} = \frac{\begin{bmatrix}\text{Number of}\\\text{hatched insects}\\\text{in untreated}\\\text{group}\end{bmatrix} - \begin{bmatrix}\text{Number of}\\\text{hatched insects}\\\text{in treated}\\\text{group}\end{bmatrix}}{\begin{bmatrix}\text{Number of}\\\text{hatched insects}\\\text{in untreated}\\\text{group}\end{bmatrix}} \times 100$$

Physical property:

compound No. 1382 m.p. 164–166. Yield 36%.
compound No. 1414 m.p. 167–169. Yield 36%.

Test Example 2

Insecticidal Effect on Smaller Tea Tortrix (Adoxophyes sp.)

A tea leaf was immersed for about 30 seconds in a liquid chemical prepared by diluting a preparation containing each of the compounds listed in Tables 1 to 33 as an active ingredient to adjust the concentration to 500 ppm. After air-drying, the leaf was placed in a plastic Petri dish with a diameter of 9 cm and inoculated with larvae of smaller tea tortrix, and the Petri dish was allowed to stand in a room thermostated at 25° C. and having a humidity of 70%. Eight days after the inoculation, the dead and alive were counted and the mortality was calculated according to the following equation. The test was carried out with three replications of 10 insects.

$$\text{Corrected mortality(\%)} = \frac{\begin{bmatrix}\text{Number of sur-}\\\text{viving insects}\\\text{in untreated}\\\text{group}\end{bmatrix} - \begin{bmatrix}\text{Number of sur-}\\\text{viving insects}\\\text{in treated}\\\text{group}\end{bmatrix}}{\begin{bmatrix}\text{Number of sur-}\\\text{viving insects}\\\text{in untreated}\\\text{group}\end{bmatrix}} \times 100$$

As a result, the following compounds were found to have a corrected mortality of 90% or more: compound Nos. 13, 18, 55, 57, 127, 136, 230, 464, 484, 512, 524, 737, 794, 795, 805, 821, 989, 1009, 1048, 1095, 1127, 1189, 1204, 1220, 1247, 1249, 1251, 1255, 1303, 1313, 1473, 1505, 1548 and 1549.

As described above, the agricultural and horticultural insecticides containing the heterocyclic dicarboxylic acid diamide derivative of the general formula (I) of the present invention as an active ingredient have an excellent controlling effect on insect pests such as diamondback moth, common cutworm, etc.

What is claimed is:
1. A heterocyclic dicarboxylic acid diamide derivative represented by the formula (I):

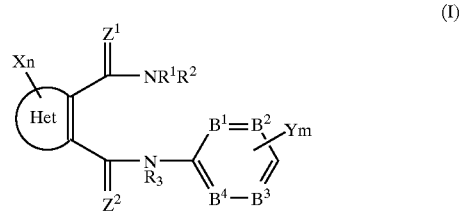

{wherein $R^1$, $R^2$ and $R^3$, which may be the same or different, are hydrogen atoms, $(C_3-C_6)$cycloalkyl groups, halo $(C_3-C_6)$cycloalkyl groups or $-A^1-(R^4)r$ (wherein $A^1$ is a $(C_1-C_8)$alkylene group, a $(C_3-C_6)$alkenylene group or a $(C_3-C_6)$alkynylene group, $R^4$, which may be the same or different, are hydrogen atoms; halogen atoms; cyano groups; nitro groups; halo$(C_1-C_6)$alkyl groups; $(C_3-C_6)$cycloalkyl groups; halo$(C_3-C_6)$cycloalkyl groups; $(C_1-C_6)$alkoxycarbonyl groups; di$(C_1-C_6)$alkoxyphosphoryl groups whose $(C_1-C_6)$alkoxy groups may be the same or different; di$(C_1-C_6)$alkoxythiophosphoryl groups whose $(C_1-C_6)$alkoxy groups may be the same or different; diphenylphosphino groups; diphenylphosphono groups; phenyl groups; substituted phenyl groups having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; heterocyclic groups; substituted heterocyclic groups having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups and halo$(C_1-C_6)$alkylsulfonyl groups; or $-A^2-R^5$ (wherein $A^2$ is $-O-$, $-S-$, $-SO-$, $-SO_2-$, $-N(R^6)-$ (wherein R is a hydrogen atom; a $(C_1-C_6)$alkylcarbonyl group; a halo$(C_1-C_6)$alkylcarbonyl group; a $(C_1-C_6)$alkoxycarbonyl group; a phenylcarbonyl group; a substituted phenylcarbonyl group having one or more substituents which may be the same or different and are selected from halogen atoms, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo $(C_1-C_6)$alkylthio groups, $(C_1-C_6)$alkylsulfinyl groups, halo $(C_1-C_6)$alkylsulfinyl groups, $(C_1-C_6)$alkylsulfonyl groups and halo$(C_1-C_6)$alkylsulfonyl groups; a phenyl$(C_1-C_4)$ alkoxycarbonyl group; a substituted phenyl$(C_1-C_4)$ alkoxycarbonyl group having on the ring one or more substituents which may be the same or different and are selected from halogen atoms, $(C_1-C_6)$alkyl groups, halo $(C_1-C_6)$alkyl groups, $(C_1-C_6)$alkoxy groups, halo$(C_1-C_6)$ alkoxy groups, $(C_1-C_6)$alkylthio groups, halo$(C_1-C_6)$ alkylthio groups, $(C_1-C_6)$alkylsulfinyl groups, halo$(C_1-C_6)$ alkylsulfinyl groups, $(C_1-C_6)$alkylsulfonyl groups and halo $(C_1-C_6)$alkylsulfonyl groups; a $(C_1-C_6)$alkylsulfonyl group; or a halo$(C_1-C_6)$alkylsulfonyl group), $-C(=O)-$ or $-C(=NOR^7)-$ (wherein $R^7$ is a hydrogen atom; a $(C_1-C_6)$ alkyl group; a halo(C₁–C₆)alkyl group; a (C₃–C₆)alkenyl group; a halo(C₃–C₆)alkenyl group; a (C₃–C₆)alkynyl group; a cyclo(C₃–C₆)alkyl group; a phenyl(C₁–C₄)alkyl group; or a substituted phenyl(C₁–C₄)alkyl group having on the ring one or more substituents which may be the same or different and are selected from halogen atoms, (C₁–C₆)alkyl groups, halo(C₁–C₆)alkyl groups, (C₁–C₆)alkoxy groups, halo(C₁–C₆)alkoxy groups, (C₁–C₆)alkylthio groups, halo (C₁–C₆)alkylthio groups, (C₁–C₆)alkylsulfinyl groups, halo (C₁–C₆)alkylsulfinyl groups, (C₁–C₆)alkylsulfonyl groups and halo(C₁–C₆)alkylsulfonyl groups), and R⁵ is a hydrogen atom; a (C₁–C₆)alkyl group; a halo(C₁–C₆)alkyl group; a (C₃–C₆)alkenyl group; a halo(C₃–C₆)alkenyl group; a (C₃–C₆)alkynyl group; a halo(C₃–C₆)alkynyl group; a (C₃–C₆)cycloalkyl group; a halo(C₃–C₆)cycloalkyl group; a (C₁–C₆)alkoxy(C₁–C₆)alkyl group; a (C₁–C₆)alkylthio (C₁–C₆)alkyl group; a formyl group; a (C₁–C₆) alkylcarbonyl group; a halo(C₁–C₆)alkylcarbonyl group; a (C₁–C₆)alkoxycarbonyl group; a mono(C₁–C₆) alkylaminocarbonyl group; a di(C₁–C₆)alkylaminocarbonyl group whose (C₁–C₆)alkyl groups may be the same or different; a mono(C₁–C₆)alkylaminothiocarbonyl group; a di(C₁–C₆)alkylaminothiocarbonyl group whose (C₁–C₆) alkyl groups may be the same or different; a di(C₁–C₆) alkoxyphosphoryl group whose (C₁–C₆)alkoxy groups may be the same or different; a di(C₁–C₆)alkoxythiophosphoryl group whose (C₁–C₆)alkoxy groups may be the same or different; a phenyl group; a substituted phenyl group having one or more substituents which may be the same or different and are selected from halogen atoms, (C₁–C₅)alkyl groups, halo(C₁–C₆)alkyl groups, (C₁–C₆)alkoxy groups, halo (C₁–C₆)alkoxy groups, (C₁–C₆)alkylthio groups, halo (C₁–C₆)alkylthio groups, (C₁–C₆)alkylsulfinyl groups, halo (C₁–C₆)alkylsulfinyl groups, (C₁–C₆)alkylsulfonyl groups and halo(C₁–C₆)alkylsulfonyl groups; a phenyl(C₁–C₄)alkyl group; a substituted phenyl(C₁–C₄)alkyl group having on the ring one or more substituents which may be the same or different and are selected from halogen atoms, (C₁–C₆)alkyl groups, halo(C₁–C₆)alkyl groups, (C₁–C₆)alkoxy groups, halo(C₁–C₆)alkoxy groups, (C₁–C₆)alkylthio groups, halo (C₁–C₆)alkylthio groups, (C₁–C₆)alkylsulfinyl groups, halo (C₁–C₆)alkylsulfinyl groups, (C₁–C₆)alkylsulfonyl groups and halo(C₁–C₆)alkylsulfonyl groups; a heterocyclic group; or a substituted heterocyclic group having one or more substituents which may be the same or different and are selected from halogen atoms, (C₁–C₆)alkyl groups, halo (C₁–C₆)alkyl groups, (C₁–C₆)alkoxy groups, halo(C₁–C₆) alkoxy groups, (C₁–C₆)alkylthio groups, halo(C₁–C₆) alkylthio groups, (C₁–C₆)alkylsulfinyl groups, halo(C₁–C₆) alkylsulfinyl groups, (C₁–C₆)alkylsulfonyl groups and halo (C₁–C₆)alkylsulfonyl groups), and r is an integer of 1 to 4), provided that R¹ and R² are not hydrogen atoms at the same time, R¹ and R² together with the N to which they are attached may form a 4 to 7 membered ring by combining to each other, in which the ring may contain the same or different 1 to 3 hetero atoms selected from the group consisting of oxygen atom, sulfur atom and nitrogen atom, Het is a heterocyclic group represented by any of the following formulas Q1 to Q4:

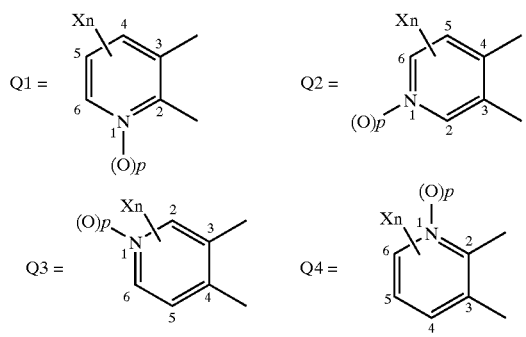

(wherein X, which may be the same or different, are halogen atoms; cyano groups; nitro groups; (C₃–C₆) cycloalkyl groups; halo(C₃–C₆)cycloalkyl groups; tri (C₁–C₆)alkylsilyl groups whose (C₁–C₆)alkyl groups may be the same or different; phenyl groups; substituted phenyl groups having one or more substituents which may be the same or different and are selected from halogen atoms, (C₁–C₆)alkyl groups, halo(C₁–C₆) alkyl groups, (C₁–C₆)alkoxy groups, halo(C₁–C₆) alkoxy groups, (C₁–C₆)alkylthio groups, halo(C₁–C₆) alkylthio groups, (C₁–C₆)alkylsulfinyl groups, halo (C₁–C₆)alkylsulfinyl groups, (C₁–C₆)alkylsulfonyl groups and halo(C₁–C₆)alkylsulfonyl groups; heterocyclic groups; substituted heterocyclic groups having one or more substituents which may be the same or different and are selected from halogen atoms, (C₁–C₆) alkyl groups, halo(C₁–C₆)alkyl groups, (C₁–C₆)alkoxy groups, halo(C₁–C₆)alkoxy groups, (C₁–C₆)alkylthio groups, halo(C₁–C₆)alkylthio groups, (C₁–C₆) alkylsulfinyl groups, halo(C₁–C₆)alkylsulfinyl groups, (C₁–C₆)alkylsulfonyl groups and halo(C₁–C₆) alkylsulfonyl groups; or —A³—R⁸ —[wherein A³ is —O—, —S—, —SO—, —SO₂—, —N(R⁶)— (wherein R⁶ is as defined above), —C(=O)—, —C(=NOR⁷)— (wherein R⁷ is as defined above), a (C₁–C₆)alkylene group, a halo(C₁–C₆)alkylene group, a (C₂–C₆)alkenylene group, a halo(C₂–C₆)alkenylene group, a (C₂–C₆)alkynylene group or a halo(C₃–C₆) alkynylene group, and R⁸ is as follows:

(1) when A³ is —O—, —S—, —SO—, —SO₂— or —N(R⁶)— (wherein R⁶ is as defined above), then R⁸ is a halo(C₃–C₆)cycloalkyl group; a halo(C₃–C₆) cycloalkenyl group; a phenyl group; a substituted phenyl group having one or more substituents which may be the same or different and are selected from halogen atoms, (C₁–C₆)alkyl groups, halo(C₁–C₆) alkyl groups, (C₁–C₆)alkoxy groups, halo(C₁–C₆) alkoxy groups, (C₁–C₆)alkylthio groups, halo (C₁–C₆)alkylthio groups, (C₁–C₆)alkylsulfinyl groups, halo(C₁–C₆)alkylsulfinyl groups, (C₁–C₆) alkylsulfonyl groups and halo(C₁–C₆)alkylsulfonyl groups; a heterocyclic group; a substituted heterocyclic group having one or more substituents which may be the same or different and are selected from halogen atoms, (C₁–C₆)alkyl groups, halo(C₁–C₆) alkyl groups, (C₁–C₆)alkoxy groups, halo(C₁–C₆) alkoxy groups, (C₁–C₆)alkylthio groups, halo (C₁–C₆)alkylthio groups, (C₁–C₆)alkylsulfinyl groups, halo(C₁–C₆)alkylsulfinyl groups, (C₁–C₆) alkylsulfonyl groups and halo(C₁–C₆)alkylsulfonyl groups; or —A⁴—R⁹ (wherein A⁴ is a (C₁–C₆) alkylene group, a halo(C₁–C₆)alkylene group, a ($C_3$–$C_6$)alkenylene group, a halo($C_3$–$C_6$)alkenylene group, a ($C_3$–$C_6$)alkynylene group or a halo($C_3$–$C_6$) alkynylene group, and $R^9$ is a hydrogen atom; a halogen atom; a ($C_3$–$C_6$)cycloalkyl group; a halo ($C_3$–$C_6$)cycloalkyl group; a ($C_1$–$C_6$)alkoxycarbonyl group; a phenyl group; a substituted phenyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$) alkylthio groups, ($C_1$–$C_6$)alkylsulfinyl groups, halo ($C_1$–$C_6$)alkylsulfinyl groups, ($C_1$–$C_6$)alkylsulfonyl groups and halo($C_1$–$C_6$)alkylsulfonyl groups; or —$A^5$—$R^{10}$ (wherein $A^5$ is —O—, —S—, —SO—, —$SO_2$— or —C(=O), and $R^{10}$ is a ($C_1$–$C_6$)alkyl group; a halo($C_1$–$C_6$)alkyl group; a ($C_3$–$C_6$)alkenyl group; a halo($C_3$–$C_6$)alkenyl group; a ($C_3$–$C_6$) cycloalkyl group; a halo($C_3$–$C_6$)cycloalkyl group; a phenyl group; a substituted phenyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$-$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups and halo($C_1$–$C_6$)alkylsulfonyl groups; a heterocyclic group; or a substituted heterocyclic group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups and halo($C_1$–$C_6$)alkylsulfonyl groups)), (2) when $A^3$ is —C(=O)— or —C(=$NOR^7$)— (wherein $R^7$ is as defined above), then $R^8$ is a hydrogen atom; a ($C_1$–$C_6$)alkyl group; a halo ($C_1$–$C_6$)alkyl group; a ($C_2C_6$)alkenyl group; a halo ($C_2C_6$)alkenyl group; a ($C_3$–$C_6$)cycloalkyl group; a halo($C_3$–$C_6$)cycloalkyl group; a ($C_1$–$C_6$)alkoxy group; a ($C_1$–$C_6$)alkylthio group; a mono($C_1$–$C_6$) alkylamino group; a di($C_1$–$C_6$)alkylamino group whose ($C_1$–$C_6$)alkyl groups may be the same or different; a phenyl group; a substituted phenyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$) alkylthio groups, ($C_1$–$C_6$)alkylsulfinyl groups, halo ($C_1$–$C_6$)alkylsulfinyl groups, ($C_1$–$C_6$)alkylsulfonyl groups and halo($C_1$–$C_6$)alkylsulfonyl groups; a phenylamino group; a substituted phenylamino group having on the ring one or more substituents which may be the same or different and are selected from halogen atoms, ($C_1$–$C_6$)alkyl groups, halo($C_1$–$C_6$) alkyl groups, ($C_1$–$C_6$)alkoxy groups, halo($C_1$–$C_6$) alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$) alkylsulfonyl groups and halo($C_1$–$C_6$)alkylsulfonyl groups; a heterocyclic group; or a substituted heterocyclic group having one or more substituents which may be the same or different and are selected from halogen atoms, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$) alkylsulfonyl groups and halo($C_1$–$C_6$)alkylsulfonyl groups, and (3) when $A^3$ is a ($C_1$–$C_6$)alkylene group, a halo($C_1$–$C_6$) alkylene group, a ($C_2$–$C_6$)alkenylene group, a halo ($C_2$–$C_6$)alkenylene group, a ($C_2$–$C_6$)alkynylene group or a halo($C_3$–$C_6$)alkynylene group, then $R^8$ is a hydrogen atom; a halogen atom; a ($C_3$–$C_6$) cycloalkyl group; a halo($C_3$–$C_6$)cycloalkyl group; a ($C_1$–$C_6$)alkoxycarbonyl group; a tri($C_1$–$C_6$) alkylsilyl group whose ($C_1$–$C_6$)alkyl groups may be the same or different; a phenyl group; a substituted phenyl group having one or more substituents which may be the same or different and are selected from halogen atoms, ($C_1$–$C_6$)alkyl groups, halo($C_1$–$C_6$) alkyl groups, ($C_1$–$C_6$)alkoxy groups, halo($C_1$–$C_6$) alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$) alkylsulfonyl groups and halo($C_1$–$C_6$)alkylsulfonyl groups; a heterocyclic group; a substituted heterocyclic group having one or more substituents which may be the same or different and are selected from halogen atoms, ($C_1$–$C_6$)alkyl groups, halo($C_1$–$C_6$) alkyl groups, ($C_1$–$C_6$)alkoxy groups, halo($C_1$–$C_6$) alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$) alkylsulfonyl groups and halo($C_1$–$C_6$)alkylsulfonyl groups; or —A—$R^{11}$ (wherein $A^6$ is —O—, —S—, —SO— or —$SO_2$—, and $R^{11}$ is a ($C_3$–$C_6$)cycloalkyl group; a halo($C_3$–$C_6$)cycloalkyl group; a phenyl group; a substituted phenyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$) alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups and halo($C_1$–$C_6$)alkylsulfonyl groups; a heterocyclic group; a substituted heterocyclic group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$) alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups and halo($C_1$–$C_6$)alkylsulfonyl groups; or —$A^7$—$R^{12}$ (wherein $A^7$ is a ($C_1$–$C_6$)alkylene group, a halo ($C_1$–$C_6$)alkylene group, a ($C_2$–$C_6$)alkenylene group, a halo($C_2$–$C_6$)alkenylene group, a ($C_2$–$C_6$) alkynylene group or a halo($C_3$–$C_6$)alkynylene group, and $R^{12}$ is a hydrogen atom; a halogen atom; a ($C_3$–$C_6$)cycloalkyl group; a halo($C_3$–$C_6$)cycloalkyl group; a ($C_1$–$C_6$)alkoxy group; a halo($C_1$–$C_6$)alkoxy group; a ($C_1$–$C_6$)alkylthio group; a halo($C_1$–$C_6$) alkylthio group; a ($C_1$–$C_6$)alkylsulfinyl group; a halo ($C_1$–$C_6$)alkylsulfinyl group; a ($C_1$–$C_6$)alkylsulfonyl group; a halo($C_1$–$C_6$)alkylsulfonyl group; a phenyl group; a substituted phenyl group having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups; a phenoxy group; a substituted phenoxy group having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_8)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_5)$alkylsulfonyl groups and halo$(C_1$–$C_6)$alkylsulfonyl groups; a phenylthio group; a substituted phenylthio group having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups; a heterocyclic group; or a substituted heterocyclic group having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups)), and n is an integer of 0 to 3, X may form a condensed ring selected from the group consisting of indole ring, benzo[b]furan ring, benzo[b]thiophene ring, quinoline ring, isoquinoline ring, naphthyridine ring, quinoxaline ring and cinnoline ring, by combining together with the adjacent atoms in the heterocyclic ring, and said condensed ring may have one or more substituents, which may be the same or different, and are selected from halogen atoms; $(C_1$–$C_6)$alkyl groups; halo$(C_1$–$C_6)$alkyl groups; $(C_1$–$C_6)$alkoxy groups; halo$(C_1$–$C_6)$alkoxy groups; $(C_1$–$C_6)$alkylthio groups; halo$(C_1$–$C_6)$alkylthio groups; $(C_1$–$C_6)$alkylsulfinyl groups; halo$(C_1$–$C_6)$alkylsulfinyl groups; $(C_1$–$C_6)$alkylsulfonyl groups; halo$(C_1$–$C_6)$alkylsulfonyl groups; phenyl group; substituted phenyl groups having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups; heterocyclic groups; and substituted heterocyclic groups having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups, W is O, S or N—$R^{13}$ (wherein $R^{13}$ is a $(C_1$–$C_6)$alkyl group; a halo$(C_1$–$C_6)$alkyl group; a $(C_3$–$C_6)$alkenyl group; a halo$(C_3$–$C_6)$alkenyl group; a $(C_3$–$C_6)$alkynyl group; a halo$(C_3$–$C_6)$alkynyl group; a $(C_1$–$C_6)$alkoxy group; a phenyl group; a substituted phenyl group having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups; a phenyl$(C_1$–$C_6)$alkyl group; or a substituted phenyl$(C_1$–$C_6)$alkyl group having on the ring one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups), and p and q, which may be the same or different, are integers of 0 to 1), $B^1$, $B^2$, $B^3$ and $B^4$, which may be the same or different, are carbon atoms, Y, which may be the same or different, are halogen atoms; cyano groups; nitro groups; halo$(C_3$–$C_6)$cycloalkyl groups; phenyl groups; substituted phenyl groups having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups; heterocyclic groups; substituted heterocyclic groups having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups; or —$A^3$—$R^3$ (wherein $A^3$ and $R^8$ are as defined above), and m is an integer of 1 to 5, Y may form a condensed ring by combining together with the adjacent carbon atoms in the aromatic ring, and said condensed ring may have one or more substituents, which may be the same or different, and are selected from halogen atoms; $(C_1$–$C_6)$alkyl groups; halo$(C_1$–$C_6)$alkyl groups; $(C_1$–$C_6)$alkoxy groups; halo$(C_1$–$C_6)$alkoxy groups; $(C_1$–$C_6)$alkylthio groups; halo$(C_1$–$C_6)$alkylthio groups; $(C_1$–$C_6)$alkylsulfinyl groups; halo$(C_1$–$C_6)$alkylsulfinyl groups; $(C_1$–$C_6)$alkylsulfonyl groups; halo$(C_1$–$C_6)$alkylsulfonyl groups; phenyl group; substituted phenyl groups having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo$(C_1$–$C_6)$alkylthio groups, $(C_1$–$C_6)$alkylsulfinyl groups, halo$(C_1$–$C_6)$alkylsulfinyl groups, $(C_1$–$C_6)$alkylsulfonyl groups and halo$(C_1$–$C_6)$alkylsulfonyl groups; heterocyclic groups; and substituted heterocyclic groups having one or more substituents which may be the same or different and are selected from halogen atoms, $(C_1$–$C_6)$alkyl groups, halo$(C_1$–$C_6)$alkyl groups, $(C_1$–$C_6)$alkoxy groups, halo$(C_1$–$C_6)$alkoxy groups, $(C_1$–$C_6)$alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups and halo($C_1$–$C_6$) alkylsulfonyl groups, and each of $Z^1$ and $Z^2$ is an oxygen atom or a sulfur atom, provided that:
(1) when Het is Q2, and $B^1$, $B^2$, $B^3$ and $B^4$ are carbon atoms at the same time, then Ym is other than 3-chloro-2-methyl group, 3-chloro-2,6-diethyl group, 5chloro-2-methyl group, 2,6-diethyl group, 4-chloro-2-fluoro group and 2-ethyl-6-methyl group, and (2) when Het is Q4 and $B^1$, $B^2$, $B^3$ and $B^4$ are carbon atoms at the same time, then Ym is other than 2,5-dichloro group, 2,4-difluoro group, 2,6-difluoro group, 3-chloro-2-methyl group, 5-chloro-2-methyl group, 5-fluoro-2-methyl group, 2,6-dimethyl group, 2,6-diethyl group, 2-ethyl-6-methyl group, 2-methoxy-5-nitro group, 2-methoxy-5methyl group, 2,6-diethoxy group, 3-bromo-2-methyl group, 3-fluoro-2-methyl group, 3-iodo-2-methyl group, 3-cyano-2-methyl group, 3-difluoromethoxy-2-methyl group, 5-chloro-2-ethyl group, 2,5-dimethyl group, 2,3-dichloro group, 3-chloro2,6-diethyl group, 4-trifluoromethyl group, 3-methoxycarbonyl-2-methyl group, 3-trifluoromethyl-2-methyl group, 3,5-dichloro-2, 6diethyl group, 3,4-dichloro group, 3-(methoxycarbonylmethyloxy)-2-methyl group, 2-methyl-3-nitro group and 4-trifluoromethoxy group.

2. A heterocyclic dicarboxylic acid diamide derivative according to claim 1, wherein Het is Q1, Q2, Q3 or Q4, $R^1$ is a ($C_3$–$C_6$)cycloalkyl group, a halo($C_3$–$C_6$)cycloalkyl group or —$A^1$—($R^4$)r (wherein $A^1$ is a ($C_1$–$C_8$)alkylene group, $R^4$, which may be the same or different, are hydrogen atoms; halogen atoms; cyano groups; nitro groups; ($C_1$–$C_6$) alkoxycarbonyl groups; di($C_1$–$C_6$)alkoxyphosphoryl groups whose ($C_1$–$C_6$) alkoxy groups may be the same or different; di($C_1$–$C_6$)alkoxythiophosphoryl groups whose ($C_1$–$C_6$) alkoxy groups may be the same or different; phenyl groups; substituted phenyl groups having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$) alkylsulfonyl groups; pyridyl groups; substituted pyridyl groups having one or more substituents which may be the same or different and are selected from halogen atoms, ($C_1$–$C_6$)alkyl groups, halo($C_1$–$C_6$)alkyl groups, ($C_1$–$C_6$) alkoxy groups, halo($C_1$–$C_6$)alkoxy groups, ($C_1$–$C_6$) alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups and halo($C_1$–$C_6$)alkylsulfonyl groups; or —$A^2$—$R^5$ (wherein $A^2$ is —O—, —S—, —SO—, —$SO_2$—, —N($R^6$)— (wherein $R^6$ is a hydrogen atom, a ($C_1$–$C_6$)alkylcarbonyl group, a halo($C_1$–$C_6$) alkylcarbonyl group or a ($C_1$–$C_6$)alkoxycarbonyl group), or —C(=N$OR^7$)— (wherein $R^7$ is a hydrogen atom, a ($C_1$–$C_6$) alkyl group or a halo($C_1$–$C_6$)alkyl group), and $R^5$ is a hydrogen atom; a ($C_1$–$C_6$)alkyl group; a halo($C_1$–$C_6$)alkyl group; a ($C_1$–$C_6$)cycloalkyl group; a halo($C_1$–$C_6$)cycloalkyl group; a phenyl group; a substituted phenyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$)alkylsulfonyl groups; a pyridyl group; or a substituted pyridyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$) alkylsulfonyl groups), and r is an integer of 1 to 4), $R^2$ and $R^3$, which may be the same or different, are hydrogen atoms or ($C_1$–$C_6$)alkyl groups, X and Y, which may be the same or different, are halogen atoms; cyano groups; nitro groups; phenyl groups; substituted phenyl groups having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$)alkylsulfonyl groups; pyridyl groups; substituted pyridyl groups having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$) alkylsulfonyl groups; or —$A^3$—$R^8$ [wherein $A^3$ is —O—, —S—, —SO—, —$SO_2$—, a ($C_1$–$C_6$)alkylene group, a halo ($C_1$–$C_6$)alkylene group, a ($C_2$–$C_6$)alkenylene group, a halo ($C_2$–$C_6$)alkenylene group, a ($C_2$–$C_6$)alkynylene group or a halo($C_3$–$C_6$)alkynylene group, and $R^8$ is as follows:

(1) when $A^3$ is —O—, —S—, —SO— or —$SO_2$—, then $R^8$ is a phenyl group; a substituted phenyl group having one or more substituents which may be the same or different and are selected from halogen atoms, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups and halo($C_1$–$C_6$) alkylsulfonyl groups; a pyridyl group; a substituted pyridyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups and halo($C_1$–$C_6$)alkylsulfonyl groups; or —$A^4$—$R^9$ (wherein $A^4$ is a ($C_1$–$C_6$)alkylene group, a halo($C_1$–$C_6$) alkylene group, a ($C_3$–$C_6$)alkenylene group, a halo ($C_3$–$C_6$)alkenylene group, a ($C_3$–$C_6$)alkynylene group or a halo($C_3$–$C_6$)alkynylene group, and $R^9$ is a hydrogen atom, a halogen atom or —$A^5$—$R^{10}$ (wherein $A^5$ is —O—, —S—, —SO— or —$SO_2$—, and $R^{10}$ is a ($C_1$–$C_6$)alkyl group, a halo($C_1$–$C_6$)alkyl group, a ($C_3$–$C_6$)alkenyl group, a halo($C_3$–$C_6$)alkenyl group, a ($C_3$–$C_6$)cycloalkyl group or a halo($C_3$–$C_6$)cycloalkyl group)), and (2) when $A^3$ is a ($C_1$–$C_6$)alkylene group, a halo($C_1$–$C_6$) alkylene group, a ($C_2$–$C_6$)alkenylene group, a halo ($C_2$–$C_6$)alkenylene group, a ($C_2$–$C_6$)alkynylene group or a halo($C_3$–$C_6$)alkynylene group, then $R^8$ is a hydrogen atom; a halogen atom; a ($C_3$–$C_6$)cycloalkyl group; a halo($C_3$–$C_6$)cycloalkyl group; a tri($C_1$–$C_6$)alkylsilyl group whose ($C_1$–$C_6$)alkyl groups may be the same or different; a phenyl group; a substituted phenyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$) alkylsulfonyl groups; a pyridyl group; a substituted pyridyl group having one or more substituents which may be the same or different and are selected from halogen atoms, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$) alkylsulfinyl groups, ($C_1$–$C_6$)alkylsulfonyl groups and halo($C_1$–$C_6$)alkylsulfonyl groups; or —$A^6$—$R^{11}$ (wherein $A^6$ is —O—, —S—, —SO— or —$SO_2$—, and $R^{11}$ is —$A^7$—$R^{12}$ (wherein $A^7$ is a ($C_1$–$C_6$) alkylene group, a halo($C_1$–$C_6$)alkylene group, a ($C_2$–$C_6$)alkenylene group, a halo($C_2$–$C_6$)alkenylene group, a ($C_2$–$C_6$)alkynylene group or a halo($C_3$–$C_6$) alkynylene group, and $R^{12}$ is a hydrogen atom, a halogen atom, a ($C_1$–$C_6$)alkoxy group, a halo($C_1$–$C_6$) alkoxy group, a ($C_1$–$C_6$)alkylthio group, a halo($C_1$–$C_6$) alkylthio group, a ($C_1$–$C_6$)alkylsulfinyl group, a halo ($C_1$–$C_6$)alkylsulfinyl group, a ($C_1$–$C_6$)alkylsulfonyl group or a halo($C_1$–$C_6$)alkylsulfonyl group))], both $B^1$ and $B^4$ are carbon atoms, $B^2$ and $B^3$, which may be the same or different, are carbon atoms or nitrogen atoms, and each of $Z^1$ and $Z^2$ is an oxygen atom.

3. A heterocyclic dicarboxylic acid diamide derivative according to claim 2, wherein X, which may be the same or different, are halogen atoms, nitro groups, halo($C_1$–$C_6$)alkyl groups, halo($C_1$–$C_6$)alkoxy groups or halo($C_1$–$C_6$)alkylthio groups, and n is an integer of 0 to 3.

4. A heterocyclic dicarboxylic acid diamide derivative according to claim 3, wherein Y, which may be the same or different, are halogen atoms, ($C_1$–$C_6$)alkyl groups, halo ($C_1$–$C_6$)-alkyl groups, ($C_1$–$C_6$)alkoxy groups, halo($C_1$–$C_6$) alkoxy groups, ($C_1$–$C_6$)alkylthio groups, halo($C_1$–$C_6$) alkylthio groups, halo($C_1$–$C_6$)alkoxyhalo($C_1$–$C_6$)alkoxy groups, halo($C_1$–$C_6$)-alkoxyhalo($C_1$–$C_6$)alkylthio groups, halo($C_1$–$C_6$)alkylsulfinyl groups or halo($C_1$–$C_6$) alkylsulfonyl groups, and m is an integer of 1 to 5.

5. A heterocyclic dicarboxylic acid diamide derivative according to claim 4, wherein $R^1$ is a ($C_1$–$C_6$)alkyl group, a ($C_1$–$C_6$)alkoxy($C_1$–$C_8$)alkyl group, a ($C_1$–$C_6$)alkylthio ($C_1$–$C_8$)-alkyl group, a ($C_1$–$C_6$)alkylsulfinyl($C_1$–$C_8$)alkyl group or a ($C_1$–$C_6$)alkylsulfonyl($C_1$–$C_8$)alkyl group, and $R^2$ and $R^3$, which may be the same or different, are hydrogen atoms or methyl groups.

6. An agricultural and horticultural insecticide characterized by containing a heterocyclic dicarboxylic acid diamide derivative according to claim 1 as an active ingredient.

7. A method for applying an agricultural and horticultural insecticide, characterized by treating a crop to be protected or soil with an effective amount of an agricultural and horticultural insecticide according to claim 6 in order to protect useful crops against insect pests.

* * * * *